US012790626B2

(12) United States Patent
Donohue et al.

(10) Patent No.: US 12,790,626 B2
(45) Date of Patent: Nov. 10, 2026

(54) RECOMBINANT MICROORGANISMS THAT CATABOLIZE ACETOVANILLONE AND METHODS OF USING SAME

(71) Applicant: Wisconsin Alumni Research Foundation, Madison, WI (US)

(72) Inventors: Timothy Donohue, Middleton, WI (US); Benjamin Hall, Waukesha, WI (US); Daniel Noguera, Madison, WI (US); Jeanette Neri, Bull Valley, IL (US)

(73) Assignee: Wisconsin Alumni Research Foundation, Madison, WI (US)

( * ) Notice: Subject to any disclaimer, the term of this patent is extended or adjusted under 35 U.S.C. 154(b) by 252 days.

(21) Appl. No.: 18/796,449

(22) Filed: Aug. 7, 2024

(65) Prior Publication Data

US 2026/0043053 A1 Feb. 12, 2026

(51) Int. Cl.

| | |
|---|---|
| ***C12P 7/22*** | (2006.01) |
| ***C12N 9/12*** | (2006.01) |
| ***C12P 7/24*** | (2006.01) |

(52) U.S. Cl.

CPC .............. *C12P 7/22* (2013.01); *C12N 9/1205* (2013.01); *C12P 7/24* (2013.01); *C12Y 207/01071* (2013.01)

(58) Field of Classification Search

CPC ....................... C12N 9/1205; C12Y 207/01071

See application file for complete search history.

(56) References Cited

U.S. PATENT DOCUMENTS

2008/0295196 A1* 11/2008 Abad ................. C12N 15/8274 800/320.2

OTHER PUBLICATIONS

Hall et al. "Mark, a Novosphingobium aromaticivorans kinase required for catabolismof multiple aromatic monomers" J. Biol. Chem. (2025) 301(10) 110606, 15 pages (Year: 2025).*

* cited by examiner

*Primary Examiner* — Thane Underdahl

(74) *Attorney, Agent, or Firm* — Daniel A. Blasiole; DeWitt LLP

(57) ABSTRACT

Recombinant microorganisms that catabolize lignin aromatics, such as acetovanillone, and methods of using same to catabolize the lignin aromatics.

19 Claims, 29 Drawing Sheets

Specification includes a Sequence Listing.

RECOMBINANT MICROORGANISMS THAT CATABOLIZE ACETOVANILLONE AND METHODS OF USING SAME

STATEMENT REGARDING FEDERALLY SPONSORED RESEARCH

This invention was made with government support under DE-SC0018409 awarded by the US Department of Energy. The government has certain rights in the invention.

SEQUENCE LISTING

The instant application contains a Sequence Listing which has been submitted in XML format and is hereby incorporated by reference in its entirety. The XML copy, created on Jul. 19, 2024, is named USPTO-09824546-P240180US01-APP-SEQ_LIST.xml and is 12,518 bytes in size.

Electronic Tables

Tables 4-7 have been submitted as ASCII text files via EFS-Web and are incorporated by reference.

The ASCII text file of Table 4 is named "Table_4.txt," was created on Jul. 20, 2024, and is 27,234 bytes in size.

The ASCII text file of Table 5 is named "Table_5.txt," was created on Jul. 20, 2024, and is 61,097 bytes in size.

The ASCII text file of Table 6 is named "Table_6.txt," was created on Jul. 20, 2024, and is 19,260 bytes in size.

The ASCII text file of Table 7 is named "Table_7.txt," was created on Jul. 20, 2024, and is 2,344,468 bytes in size.

LENGTHY TABLES

The patent contains a lengthy table section. A copy of the table is available in electronic form from the USPTO web site (https://seqdata.uspto.gov/docdetail?docId=US12790626B2). An electronic copy of the table will also be available from the USPTO upon request and payment of the fee set forth in 37 CFR 1.19(b)(3).

FIELD OF THE INVENTION

The invention is directed to recombinant microorganisms that catabolize lignin aromatics, such as acetovanillone and other lignin aromatics, and methods of using same to catabolize the lignin aromatics. The invention is also directed to aromatic kinases involved in the catabolism of the lignin aromatics and methods of using same to phosphorylate the lignin aromatics.

BACKGROUND

As the world looks to renewable sources for chemicals, lignin is gaining much attention as a potential raw material (1-4). Lignin is a heterogeneous polymer of aromatics that helps plant cell walls maintain their structure (5), and it represents the second most abundant biopolymer on the planet (6). However, in order to utilize lignin for conversion into desirable chemicals, it must be depolymerized. Many chemical methods for lignin depolymerization exist, most of which yield mixtures of aromatic compounds, whose identities and chemical modifications to the aromatic ring depend on the parameters of the deconstruction process and the plant material (3,7).

One aromatic monomer that is recovered at high levels after oxidative lignin depolymerization is acetovanillone, a chemically modified form of vanillin that contains an acetyl side chain on the aromatic ring (3). In some cases, acetovanillone can represent the second or third most abundant aromatic monomer after oxidative lignin depolymerization (8,9). Oxidative treatment of isolated black liquor or kraft lignin also generates significant amounts of acetovanillone (10-13). In addition, acetovanillone is produced from microbial oxidation of the biomass hydrogenolysis product ethylguaiacol, which can represent up to 10% of aromatic monomers (14). Based on the abundance of acetovanillone in several biomass deconstruction streams, microbes that can catabolize acetovanillone are needed. Such microbes can be used to convert acetovanillone and other aromatics into valuable products in processes of generating chemicals from lignin.

SUMMARY OF THE INVENTION

One aspect of the invention is directed to recombinant microorganisms. In some versions, the recombinant microorganisms comprise a recombinant aromatic kinase gene. The recombinant aromatic kinase gene can encode an aromatic kinase protein. The aromatic kinase protein can be a homolog of Saro_1862 of *Novosphingobium aromaticivorans* DSM12444 comprising amino acid sequence comprising a lysine at a position corresponding to position 16 of SEQ ID NO:4.

In some versions, the amino acid sequence is at least 95% or at least 99% identical to SEQ ID NO:4 or any sequence identified in Table 7. In some versions, the amino acid sequence is at least 80% identical to SEQ ID NO:4. In some versions, the amino acid sequence is at least 95% identical to SEQ ID NO:4.

In some versions, the recombinant microorganism is a bacterium. In some versions, the recombinant microorganism is a member of Actinomycetota, Alphaproteobacteria, Aquificac, Bacillota, Bacteroidota, Betaproteobacteria, Chlorobiota, Chloroflexota, Desulfuromonadia, Epsilonproteobacteria, Gammaproteobacteria, Nitrospiria, Planctomycetota, Thermomicrobiota, or Verrucomicrobiota. In some versions, the recombinant microorganism is an Alphaproteobacterium. In some versions, the recombinant microorganism is from an order selected from the group consisting of Sphingomonadales, *Actinomyces*, Gammaproteobacteria, Betaproteobacteria, and Bacilli. In some versions, the recombinant microorganism is from family Erythrobacteraceae. In some versions, the recombinant microorganism is from genus *Novosphingobium.*

In some versions, the recombinant microorganism of claim 1, wherein the recombinant microorganism is capable of growing on acetovanillone, guaiacylpropanone, or p-OH acetophenone as a sole carbon source. In some versions, the recombinant microorganism is capable of growing on acetovanillone as a sole carbon source.

Another aspect of the invention is directed to methods of catabolizing a lignin aromatic. In some versions, the methods comprise culturing a recombinant microorganism of the invention in a medium comprising the lignin aromatic to thereby catabolize the lignin aromatic.

In some versions, the lignin aromatic comprises one or more of acetovanillone, guaiacylpropanone, and p-OH acetophenone. In some versions, the lignin aromatic comprises acetovanillone.

Another aspect of the invention is directed to recombinant aromatic kinase proteins. In some versions, the recombinant aromatic kinase proteins comprise an amino acid sequence at least 95% identical to SEQ ID NO:4, wherein the amino acid sequence comprises a lysine at a position corresponding to position 16 of SEQ ID NO:4. In some versions, the amino acid sequence is at least 99% identical to SEQ ID NO:4.

Another aspect of the invention is directed to phosphorylating a lignin aromatic. In some versions, the methods comprise contacting a lignin aromatic with a recombinant aromatic kinase protein of the invention to thereby phosphorylate the lignin aromatic. The lignin aromatic can comprise any lignin aromatic described herein as being phosphorylated by the recombinant aromatic kinase protein having a sequence of SEQ ID NO:4. Exemplary lignin aromatics include those shown as being phosphorylated by the recombinant aromatic kinase proteins of the invention in FIGS. 1, 4, 7, 8, and 13-29.

The objects and advantages of the invention will appear more fully from the following detailed description of the preferred embodiment of the invention made in conjunction with the accompanying drawings.

DETAILED DESCRIPTION OF THE INVENTION

Figure 1:
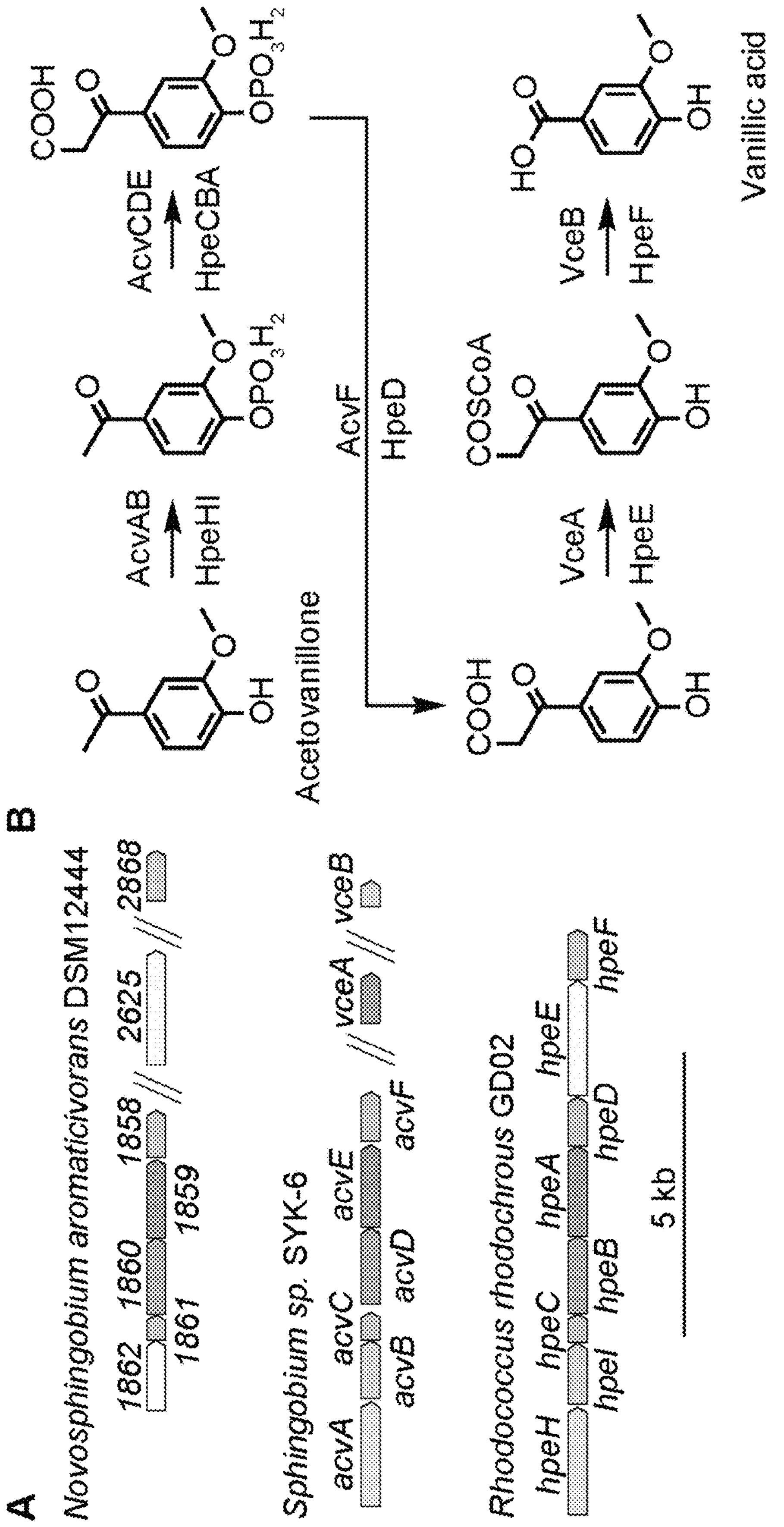
FIG. 1. *N. aromaticivorans* DSM12444 encodes homologs of all genes required for acetovanillone metabolism, except for genes encoding the heterodimeric acetovanillone kinases AcvAB/HpeHI. A, genomic arrangement of homologs relevant for acetovanillone metabolism in *N. aromaticivorans* DSM12444*, Sphingobium* sp. SYK-6 (20), and *R. rhodochrous* GD02 (21). Numbers for *N. aromaticivorans* denote Saro_NNNN locus tags. B, acetovanillone metabolic pathway as described in (20,21). Enzymes used by *Sphingobium* sp. SYK-6 are shown above each arrow, while enzymes used by *R. rhodochrous* GD02 are shown below each arrow.

The recombinant microorganisms of the invention can comprise a recombinant aromatic kinase gene encoding an aromatic kinase protein. The aromatic kinase proteins of the invention are enzymes capable of phosphorylating a lignin aromatic. In preferred versions of the invention, the aromatic kinase protein is a homolog of Saro_1862 of *Novosphingobium aromaticivorans* DSM12444 comprising amino acid sequence comprising a lysine at a position corresponding to position 16 of SEQ ID NO:4.

Saro_1862 of *Novosphingobium aromaticivorans* DSM12444 has a coding sequence of SEQ ID NO:1 and a protein sequence of SEQ ID NO:2.

The homologs of Saro_1862 of *Novosphingobium aromaticivorans* DSM12444 can comprise proteins comprising a sequence at least 80%, at least 85%, at least 90%, at least 95%, or at least 99% identical to SEQ ID NO:4, orthologs of Saro 1862 of *Novosphingobium aromaticivorans* DSM12444, and recombinant variants of the orthologs of Saro_1862 of *Novosphingobium aromaticivorans* DSM12444. Each of these homologs can be modified to comprise a lysine at a position corresponding to position 16 of SEQ ID NO:4. An exemplary coding sequence of SEQ ID NO:4 is SEQ ID NO:3. Exemplary homologs of Saro_1862 of *Novosphingobium aromaticivorans* DSM12444 comprise an amino acid sequence of SEQ ID NO:4, any amino acid sequence identified in Table 7 (e.g., by accession numbers from NCBI available on Sep. 12, 2023), or an amino acid sequence at least 80%, at least 85%, at least 90%, at least 95%, at least 96%, at least 97%, at least 98%, or at least 99% identical to SEQ ID NO:4 or any sequence identified in Table 7.

The aromatic kinase protein of the invention is preferably capable of catalyzing the phosphorylation of a lignin aromatic, such as acetovanillone, guaiacylpropanone, p-OH acetophenone, or the lignin aromatics shown in FIGS. 1, 4, 7, 8, and 13-29 or described elsewhere herein.

The recombinant microorganisms of the invention may comprise any type of microorganism. The microorganism may be prokaryotic or eukaryotic. Suitable prokaryotes include bacteria and archaea. Suitable types of bacteria include α- and γ-proteobacteria, gram-positive bacteria, gram-negative bacteria, ungrouped bacteria, phototrophs, lithotrophs, and organotrophs. Suitable eukaryotes include yeast and other fungi. The microorganism in some versions can be from an order selected from the group consisting of Sphingomonadales and Pseudomonadales. The microorganism in some versions can be from a family selected from the group consisting of Sphingomonadaceae and Pseudomonadaceae. The microorganism in some versions can be from a genus selected from the group consisting of *Sphingomonas, Sphingobium, Sphingosinicella, Sphingopyxis, Novosphingobium, Pseudomonas, Erythrobacter* (e.g., sp. SG61-1L), and *Altererythrobacter*. The microorganism in some versions can be a member of Actinomycetota, Alphaproteobacteria, Aquificae, Bacillota, Bacteroidota, Betaproteobacteria, Chlorobiota, Chloroflexota, Desulfuromonadia, Epsilonproteobacteria, Gammaproteobacteria, Nitrospiria, Planctomycetota, Thermomicrobiota, or Verrucomicrobiota. The microorganism in some versions can be an Alphaproteobacterium. The microorganism in some versions can be from an order selected from the group consisting of Sphingomonadales, *Actinomyces*, Gammaproteobacteria, Betaproteobacteria, and Bacilli. The microorganism in some versions can be from family Erythrobacteraceae. The microorganism in some versions can be from genus *Novosphingobium*. The microorganism in some versions can be an *Novosphingobium aromaticivorans*, such as *Novosphingobium aromaticivorans* DSM12444.

The recombinant genes of the invention can be configured to be expressed or overexpressed in the microorganism. If a microorganism endogenously comprises a particular gene, the gene may be modified to exchange or optimize promoters, exchange or optimize enhancers, or exchange or optimize any other genetic element to result in increased expression of the gene. Alternatively, one or more additional copies of the gene or coding sequence thereof may be introduced to the cell for enhanced expression of the gene product. If a microorganism does not endogenously comprise a particular gene, the gene or coding sequence thereof may be introduced to the microorganism for heterologous expression of the gene product. The gene or coding sequence may be incorporated into the genome of the microorganism or may be contained on an extra-chromosomal plasmid. The gene or coding sequence may be introduced to the microorganism individually or may be included on an operon. Techniques for genetic manipulation are described in further detail below. The recombinant microorganisms of the invention may be genetically altered to express or overexpress any of the specific genes or gene products explicitly described herein or homologs thereof. Various promoters capable of driving overexpression of a gene are well known in the art. See, e.g., U.S. Pat. No. 9,708,630, which is incorporated herein by reference in its entirety.

In some versions, the recombinant genes of the invention comprise a coding sequence operably linked to a heterologous genetic element. In some versions, the heterologous genetic element is a heterologous promoter.

"Homolog" as used herein with respect to a proteins and/or protein sequences refers to a protein and/or protein sequence derived, naturally or artificially, from a common ancestral protein or protein sequence. Similarly, "homolog" as used herein with respect to nucleic acids and/or nucleic acid sequences refers to nucleic acids and/or nucleic acid sequences derived, naturally or artificially, from a common ancestral nucleic acid or nucleic acid sequence. Nucleic acid or gene product (amino acid) sequences of any known gene, including the genes or gene products described herein, can be determined by searching any sequence databases known in the art using the gene name or accession number as a search term. Common sequence databases include GenBank (www.ncbi.nlm.nih.gov), ExPASy (expasy.org), KEGG (www.genome.jp), among others. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity (e.g., identity) over 50, 100, 150 or more residues (nucleotides or amino acids) is routinely used to establish homology (e.g., over the full length of the two sequences to be compared). Higher levels of sequence similarity (e.g., identity), e.g., 30%, 35% 40%, 45% 50%, 55%, 60%, 65%, 70%, 75%, 80%, 85%, 90%, 95%, or 99% or more, can also be used to establish homology. Accordingly, homologs of the genes or gene products described herein include genes or gene products having at least about 30%, 35%, 40%, 45%, 50%, 55%, 60%, 65%, 70%, 75%, 80%, 85%, 90%, 95%, or 99% identity to the genes or gene products described herein. Methods for determining sequence similarity percentages (e.g., BLASTP and BLASTN using default parameters) are described herein and are generally available. The homologous proteins should demonstrate comparable activities and, if an enzyme, participate in the same or analogous pathways. Homologs include orthologs and paralogs. "Orthologs" are genes and products thereof in different species that evolved from a common ancestral gene by speciation. Normally, orthologs retain the same or similar function in the course of evolution. Paralogs are genes and products thereof related by duplication within a genome. As used herein, "orthologs" and "paralogs" are included in the term "homologs."

For sequence comparison and homology determination, one sequence typically acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence based on the designated program parameters. A typical reference sequence of the invention is a nucleic acid or amino acid sequence corresponding to the genes or gene products described herein.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see Current Protocols in Molecular Biology, F. M. Ausubel et al., eds., Current Protocols, a joint venture between Greene Publishing Associates, Inc. and John Wiley & Sons, Inc., (supplemented through 2008)).

One example of an algorithm that is suitable for determining percent sequence identity and sequence similarity for purposes of defining homologs is the BLAST algorithm, which is described in Altschul et al., J. Mol. Biol. 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001. The above-described techniques are useful in identifying homologous sequences for use in the methods described herein.

The term "encode," such as in the phrase "the recombinant aromatic kinase gene encodes an aromatic kinase protein," is used herein in an open-ended sense, such that a gene that encodes a specified protein or amino acid sequence must code for at least the specified protein or amino acid sequence but may also code for further proteins, domains, moieties, or sequences within the same reading frame as the specified protein or amino acid sequence. Thus, in some versions, The terms "identical" or "percent identity", in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described above (or other algorithms available to persons of skill) or by visual inspection.

The phrase "substantially identical" in the context of two nucleic acids or polypeptides refers to two or more sequences or subsequences that have at least about 60%, about 65%, about 70%, about 75%, about 80%, about 85%, about 90, about 95%, about 98%, or about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, at least about 250 residues, or over the full length of the two sequences to be compared.

The terms "corresponds to" and "corresponding to" used with reference to an amino acid residue or position refer to an amino acid residue or position in a first protein sequence being positionally equivalent to an amino acid residue or position in a second reference protein sequence by virtue of the fact that the residue or position in the first protein sequence aligns to the residue or position in the reference sequence using bioinformatic techniques, for example, using the methods described herein for preparing a sequence alignment. The corresponding residue in the first protein sequence is then assigned the position number in the second reference protein sequence.

Derived: When used with reference to a nucleic acid or protein, "derived" means that the nucleic acid or polypeptide is isolated from a described source or is at least 70%, 80%, 90%, 95%, 99%, or more identical to a nucleic acid or polypeptide included in the described source.

Endogenous: As used herein with reference to a nucleic acid molecule, genetic element (e.g., gene, promoter, etc.), or polypeptide in a particular cell, "endogenous" refers to a nucleic acid molecule, genetic element, or polypeptide that is in the cell and was not introduced into the cell or transferred within the genome of the cell using recombinant engineering techniques. For example, an endogenous genetic element is a genetic element that was present in a cell in its particular locus in the genome when the cell was originally isolated from nature.

Exogenous: As used herein with reference to a nucleic acid molecule, genetic element (e.g., gene, promoter, etc.), or polypeptide in a particular cell, "exogenous" refers to any nucleic acid molecule, genetic element, or polypeptide that was introduced into the cell or transferred within the genome of the cell using recombinant engineering techniques. For example, an exogenous genetic element is a genetic element that was not present in its particular locus in the genome when the cell was originally isolated from nature.

Expression: The process by which a gene's coded information is converted into the structures and functions of a cell, such as a protein, transfer RNA, or ribosomal RNA. Expressed genes include those that are transcribed into mRNA and then translated into protein and those that are transcribed into RNA but not translated into protein (for example, transfer and ribosomal RNAs).

Introduce: When used with reference to genetic material, such as a nucleic acid, and a cell, "introduce" refers to the delivery of the genetic material to the cell in a manner such that the genetic material is capable of being expressed within the cell. Introduction of genetic material includes both transformation and transfection. Transformation encompasses techniques by which a nucleic acid molecule can be introduced into cells such as prokaryotic cells or non-animal eukaryotic cells. Transfection encompasses techniques by which a nucleic acid molecule can be introduced into cells such as animal cells. These techniques include but are not limited to introduction of a nucleic acid via conjugation, electroporation, lipofection, infection, and particle gun acceleration.

Isolated: An "isolated" biological component (such as a nucleic acid molecule, polypeptide, or cell) has been substantially separated or purified away from other biological components in which the component naturally occurs, such as other chromosomal and extrachromosomal DNA and RNA and proteins. Nucleic acid molecules and polypeptides that have been "isolated" include nucleic acid molecules and polypeptides purified by standard purification methods. The term also includes nucleic acid molecules and polypeptides prepared by recombinant expression in a cell as well as chemically synthesized nucleic acid molecules and polypeptides. In one example, "isolated" refers to a naturally occurring nucleic acid molecule that is not immediately contiguous with both of the sequences with which it is immediately contiguous (one on the 5' end and one on the 3' end) in the naturally-occurring genome of the organism from which it is derived.

Gene: Genes minimally include a promoter operably linked to a coding sequence, and can include other elements that facilitate or regulate the transcription and/or translation of the coding sequence.

Heterologous: The term "heterologous" refers to an element in an arrangement with another element that does not occur in nature. For example, a gene or protein that is heterologous to a given cell is a gene or protein that does not occur in the cell in nature. A promoter that is heterologous to a given coding sequence is a promoter that is not operably linked to the coding sequence in nature.

Nucleic acid: Encompasses both RNA and DNA molecules including, without limitation, cDNA, genomic DNA, and mRNA. Nucleic acids also include synthetic nucleic acid molecules, such as those that are chemically synthesized or recombinantly produced. The nucleic acid can be double-stranded or single-stranded. Where single-stranded, the nucleic acid molecule can be the sense strand, the antisense strand, or both. In addition, the nucleic acid can be circular or linear.

Operably linked: A first element is operably linked with a second element when the first element is placed in a functional relationship with the second element. For instance, a promoter is operably linked to a coding sequence if the promoter affects the transcription or expression of the coding sequence. A secretion signal sequence is operably linked to a protein (such as an enzyme) when the secretion signal sequence affects secretion of the protein from a cell. "Operably linked" and "operationally linked" are used interchangeably.

Overexpress: When a gene is caused to be transcribed at an elevated rate compared to the endogenous or basal transcription rate for that gene. In some examples, overexpression additionally includes an elevated rate of translation of the gene compared to the endogenous translation rate for that gene. Methods of testing for overexpression are well known in the art, for example transcribed RNA levels can be assessed using RT-PCR and protein levels can be assessed using SDS-PAGE gel analysis.

Recombinant: A recombinant nucleic acid or polypeptide is one comprising a sequence that is not naturally occurring. A recombinant gene is a gene that comprises a recombinant nucleic acid sequence, is present within a cell in which it does not naturally occur, and/or is present in a different locus (e.g., genetic locus or on an extrachromosomal plasmid) within a particular cell than in a corresponding native cell. A recombinant cell (such as a recombinant microorganism) is one that comprises a recombinant nucleic acid, a recombinant gene, or a recombinant polypeptide. An example of a recombinant gene is a gene that has a coding sequence operably linked to a heterologous promoter.

Recombinant variant: Used with reference to an ortholog, "recombinant variant" refers to a variant of the ortholog that comprises one or more modifications to amino acid sequence of the ortholog. Exemplary modifications include substitutions, deletions, and insertions. The recombinant variant preferably comprises an amino acid sequence at least 95% or at least 99% identical to the amino acid sequence of the ortholog.

Another aspect of the invention is directed to methods of catabolizing a lignin aromatic. The methods can comprise culturing the recombinant microorganism of the invention in a medium comprising the lignin aromatic to thereby catabolize the lignin aromatic.

"Lignin aromatic" as used herein refers to an aromatic present in or derived from lignin. The lignin aromatics can be a monomer, a dimer, an oligomer, or a polymer. The lignin aromatics can comprise syringyl aromatics, guaiacyl aromatics, p-hydroxyphenyl aromatics, or any combinations thereof. Syringyl, guaiacyl, and p-hydroxyphenyl aromatics differ in their degree of methoxilation of the aromatic ring. Syringyl aromatics comprise methoxy groups at the 3 and 5 positions of the aromatic ring. Guaiacyl aromatics comprise a methoxy group on only one of the 3 and 5 positions on the aromatic ring. p-Hydroxyphenyl aromatics are devoid of methoxy groups on either of the 3 and 5 positions of the aromatic ring.

Some aspects of the invention are directed to methods of catabolizing a lignin aromatic. The methods can comprise culturing a recombinant microorganism of the invention in a medium comprising the lignin aromatic to thereby catabolize the lignin aromatic.

In some versions, the lignin aromatic is derived from, isolated from, or provided in the form of depolymerized lignin. In some versions, the medium comprises depolymerized lignin. Methods of depolymerizing lignin are well known in the art. See Pandey et al. 2010 (Pandey M P, Kim C S. Lignin Depolymerization and Conversion: A Review of Thermochemical Methods. *Chemical & Engineering Technology,* 2010, Vol. 34, Issue 1, pp. 3-145) and Wang et al. 2013 (Wang H, Tucker M, Ji Y. Recent Development in Chemical Depolymerization of Lignin: A Review. *Journal of Applied Chemistry,* 2013, Volume 2013, Article ID 838645).

The depolymerized lignin can be derived from pretreated lignocellulosic biomass. Methods of pretreating lignocellulosic biomass are well known in the art. See Kumar et al. 2017 (Kumar A K and Sharma S. Recent Updates on Different Methods of Pretreatment of Lignocellulosic Feedstocks: A Review. Bioresour. Bioprocess. (2017) 4:7); Kumar et al. 2009 (Kumar, P.; Barrett, D. M.; Delwiche, M. J.; Stroeve, P., Methods for Pretreatment of lignocellulosic Biomass for Efficient Hydrolysis and Biofuel Production. Industrial & Engineering Chemistry Research 2009, 48, (8), 3713-3729); Wang et al. 2013 (Wang H, Tucker M, Ji Y. Recent Development in Chemical Depolymerization of Lignin: A Review. (2013) *Journal of Applied Chemistry.* 2013:1-9), and Karlen et al. 2020 (Karlen S D, Fasahati P, Mazaheri M, Serate J, Smith R A, Sirobhushanam S, Chen M, Tymkhin V I, Cass C L, Liu S, Padmakshan D, Xie D, Zhang Y, McGee M A, Russell J D, Coon J J, Kaeppler H F, de Leon N, Maravelias C T, Runge T M, Kaeppler S M, Sedbrook J C, Ralph J. Assessing the viability of recovering hydroxycinnamic acids from lignocellulosic biorefinery alkaline pretreatment waste streams. *ChemSusChem.* 2020 Jan. 26). Examples include chipping, grinding, milling, steam pretreatment, ammonia fiber expansion (AFEX, also referred to as ammonia fiber explosion), ammonia recycle percolation (ARP), $CO_2$ explosion, steam explosion, ozonolysis, wet oxidation, acid hydrolysis, dilute-acid hydrolysis, alkaline hydrolysis, organosolv, ionic liquids, gamma-valerolactone, enzymatic pretreatment, biological pretreatment, and pulsed electrical field treatment, among others.

The lignocellulosic biomass can be derived from any source, such as corn cobs, corn stover, cotton seed hairs, grasses, hardwood stems, leaves, newspaper, nut shells, paper, softwood stems, sorghum, switchgrass, waste papers from chemical pulps, wheat straw, wood, woody residues, mixed biomass species such as those produced by native prairie, and other sources. Sources that maintain β-5 bonds in lignin are preferred.

Another aspect of the invention is directed to recombinant aromatic kinase proteins. In some versions, the recombinant aromatic kinase proteins comprise an amino acid sequence at least 80%, at least 85%, at least 90%, at least 95%, at least 96%, at least 97%, at least 98%, at least 99% or 100% identical to SEQ ID NO:4, wherein the amino acid sequence comprises a lysine at a position corresponding to position 16 of SEQ ID NO:4.

Another aspect of the invention is directed to phosphorylating a lignin aromatic. In some versions, the methods comprise contacting a lignin aromatic with a recombinant aromatic kinase protein of the invention to thereby phosphorylate the lignin aromatic. The lignin aromatic can comprise any lignin aromatic described herein as being phosphorylated by the recombinant aromatic kinase protein having a sequence of SEQ ID NO:4. Exemplary lignin aromatics include those shown as being phosphorylated by the recombinant aromatic kinase proteins of the invention in FIGS. 1, 4, 7, 8, and 13-29.

Another aspect of the invention is directed to recombinant genes. The recombinant genes can comprise any recombinant gene of the invention and/or encode any aromatic kinase protein of the invention.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

A Newly Discovered Kinase from *Novosphingobium aromaticivorans* Involved in Catabolism of Aromatic Monomers

SUMMARY

The plant polymer lignin is an abundant renewable source of aromatics that could be used for production of various chemicals. Oxidative lignin depolymerization methods generate a variety of products that includes acetovanillone, an aromatic monomer that is a derivative of vanillin and contains an acetyl side chain on the ring. The Alphaproteobacterium *Novosphingobium aromaticivorans* strain DSM12444 can convert a variety of lignin-derived aromatic compounds into valuable products, but it cannot metabolize acetovanillone. In this work, we used adaptive laboratory evolution to identify a mutation in the previously uncharacterized gene product Saro_1862 that is both necessary and sufficient for growth of *N. aromaticivorans* in the presence of acetovanillone as a sole organic carbon source. We show that the resulting glutamate (E) to lysine (K) substitution at amino acid residue 16 allows a recombinant form of Saro_1862 to phosphorylate acetovanillone in the presence of ATP. We also find that recombinant Saro_1862 E16K phosphorylates several other aromatic compounds in vitro, and we provide genetic evidence that activity of Saro_1862 is required for metabolism of several other aromatic compounds in vivo. Structural predictions suggest that the E16K amino acid substitution in Saro_1862 enhances ATP binding in this newly discovered aromatic kinase. A search for homologs of Saro_1862 and other genes that are required for acetovanillone metabolism suggests that homologs of this newly discovered kinase could be involved in aromatic metabolism in organisms across the bacterial phylogeny.

INTRODUCTION

Among the challenges facing society is the industrial production of valuable chemicals from renewable raw materials. As the second most abundant biopolymer on Earth, lignin is a potential raw material for producing chemicals from renewable sources. While lignin oxidation is an efficient means of lignin depolymerization, it can generate modified aromatics, such as acetovanillone, that are unable to be metabolized by *Novosphingobium aromaticivorans* and other microbes that are being developed as hosts for creating valuable products from lignin. This work used adaptive laboratory evolution to identify a previously uncharacterized *N. aromaticivorans* kinase that phosphorylates acetovanillone and other aromatics. Discovery of this kinase expands our understanding of the enzymes involved in aromatic metabolism and provides new routes for engineering metabolism of acetovanillone and other lignin-derived aromatics into products by this and other microbes.

Strains of *Novosphingobium aromaticivorans* DSM12444 that convert aromatic monomers and other components of deconstructed biomass into 2-pyrone-4,6-dicarboxylic acid (PDC) (15), cis, cis-muconic acid (16), or other products (17) were developed. However, previous analysis showed that *N. aromaticivorans* DSM12444 was incapable of metabolizing acetovanillone (14). Because acetovanillone is structurally similar to vanillin and other aromatics that *N. aromaticivorans* DSM12444 can metabolize (18,19), we hypothesized that adaptive laboratory evolution could be used to yield strains able to metabolize this chemically modified product of lignin deconstruction.

In support of this hypothesis, studies in other bacteria have recently identified an acetovanillone metabolic pathway encoded by acvABCDEF and vceAB in *Sphingobium* sp. SYK-6 (20) or the homologs hpeHICBADEF in *Rhodococcus rhodochrous* GD02 (21), which converts acetovanillone to vanilloyl acetic acid, followed by further transformation to vanillic acid via a Coenzyme A (22) intermediate (FIG. 1). While the *N. aromaticivorans* DSM12444 genome encodes homologs of acvCDEFIhpeCBAD (Saro_1861-1858) and hpeEF (Saro_2625 and Saro_2868), it is not predicted to encode a protein related to the heterodimeric acetovanillone kinases AcvAB/HpeHI that catalyze the first step in metabolism of this aromatic (FIG. 1, Table 1). Thus, we hypothesized that *N. aromaticivorans* could be evolved to use alternative enzymes for one or more reactions in an acetovanillone catabolic pathway.

Here we report the use of adaptive laboratory evolution to identify mutations that allow growth of *N. aromaticivorans* in the presence of acetovanillone as a sole organic carbon source. By analyzing genome sequence changes in a set of evolved strains, we find that they each contain a mutation that generates a glutamate to lysine amino acid substitution at residue 16 of a previously uncharacterized gene product, Saro_1862. We show that this mutation is sufficient for acetovanillone metabolism when it is generated in the parent *N. aromaticivorans* strain, and that the resulting E16K amino acid change in Saro_1862 allows a recombinant form of this protein to phosphorylate acetovanillone in the presence of ATP. Purified recombinant Saro_1862 E16K also phosphorylates a variety of aromatic monomers in vitro, and we provide evidence that this newly discovered kinase is required for metabolism of selected compounds in vivo. Structural predictions suggest that the E16K substitution in Saro_1862 allows kinase activity by generating a functional ATP binding site. By searching for homologs of Saro_1862 and other genes reported to be required for acetovanillone metabolism in genome sequences of other bacteria, we find that homologs of the protein are present across the bacterial phylogeny where they could be involved in metabolism of acetovanillone and other aromatic compounds.

TABLE 1

Percent identity of acetovanillone metabolism proteins encoded by the genes shown in FIG. 1.

| | AcvA/ HpeH | AcvB/ HpeI | 1861/ AcvC/ HpeC | 1860/ AcvD/ HpeB | 1859/ AcvE/ HpeA | 1858/ AcvF/ HpeD | 2625/ HpeE | 2868/ HpeF |
|---|---|---|---|---|---|---|---|---|
| *N. aromaticivorans* vs *Sphingobium* sp. | N/A | N/A | 41% | 55% | 52% | 38% | N/A | N/A |
| *N. aromaticivorans* vs *R. rhodochrous* | N/A | N/A | 34% | 49% | 40% | 33% | 26% | 48% |
| *Sphingobium* sp. vs *R. rhodochrous* | 45% | 42% | 38% | 51% | 42% | 35% | N/A | N/A |

Results

Adaptive Laboratory Evolution Generates Acetovanillone-Metabolizing Strains of *N. aromaticivorans* DSM12444

Figure 2:
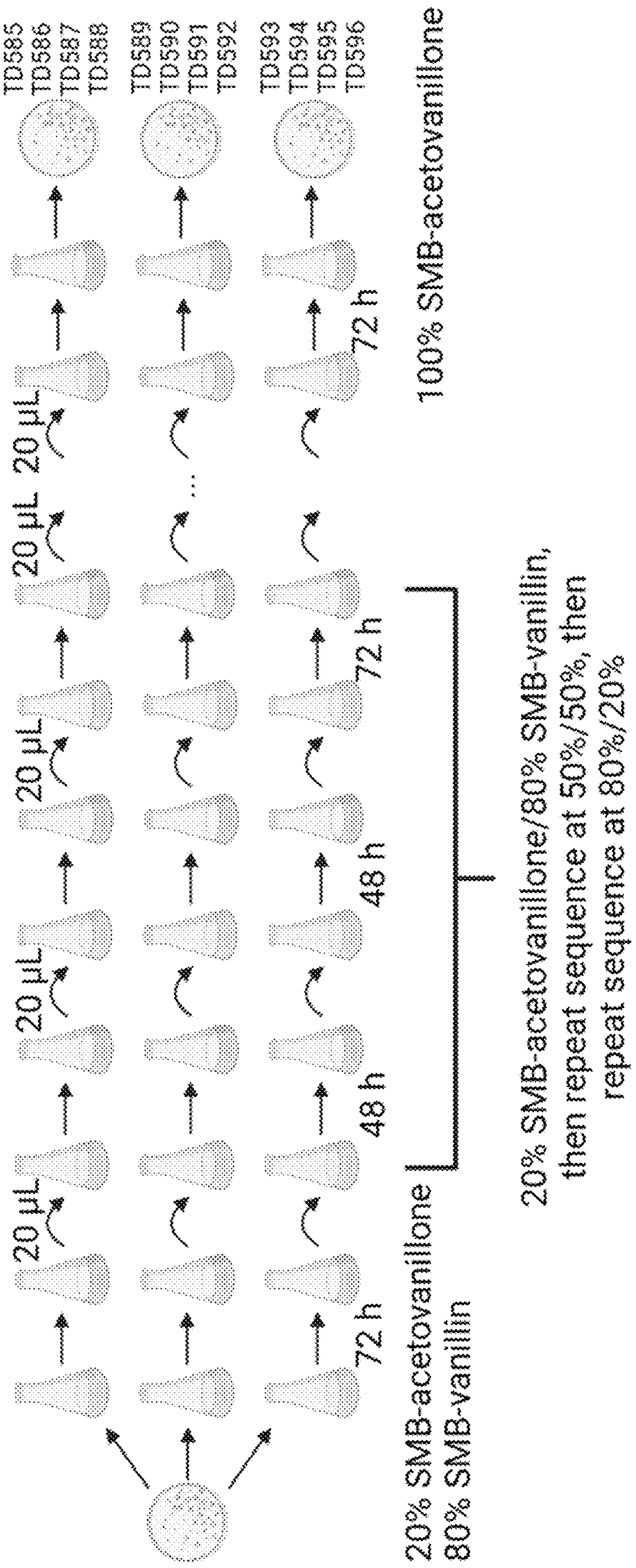
FIG. 2. Experimental procedure for adaptive laboratory evolution to isolate acetovanillone-metabolizing strains. The petri plate on the left represents the parent strain *N. aromaticivorans* 12444A1879. All flasks contained 10 mL of the specified mixture of SMB-acetovanillone and SMB-vanillin. 20 μL inoculations were used for each passage. TD numbers denote strain names of the evolved strains, isolated from single colonies of the final 100% SMB-acetovanillone cultures plated on solid SMB-acetovanillone media. Created with BioRender.com.

While *N. aromaticivorans* DSM12444 can metabolize a variety of aromatic compounds which share structural similarity with acetovanillone, including vanillin, it is not capable of catabolizing acetovanillone (14). Thus, we hypothesized that adaptive laboratory evolution was a promising strategy for identifying one or more mutations that lead to acetovanillone metabolism in *N. aromaticivorans*. To test this hypothesis, we grew the parent *N. aromaticivorans* strain 1244441879 in 3 parallel minimal media cultures with a mixture of acetovanillone and vanillin as the sole carbon sources. We initially grew cultures in media with 0.34 mM acetovanillone and 1.36 mM vanillin, passaged them three times, and gradually increased the acetovanillone:vanillin ratio throughout multiple subsequent passages until the cultures only contained acetovanillone as the sole carbon source (FIG. 2). At the end of this process, we obtained cultures that showed growth on acetovanillone as the sole carbon source after 48 h. At this point, we plated cultures on media containing acetovanillone as the sole carbon source to obtain isolated colonies, and we sequenced genomic DNA of four isolates from each of the three evolved cultures to identify mutations that arose during adaptive laboratory evolution.

Identification of a Mutation that is Both Necessary and Sufficient for Acetovanillone Metabolism by *N. aromaticivorans*

Figure 3:
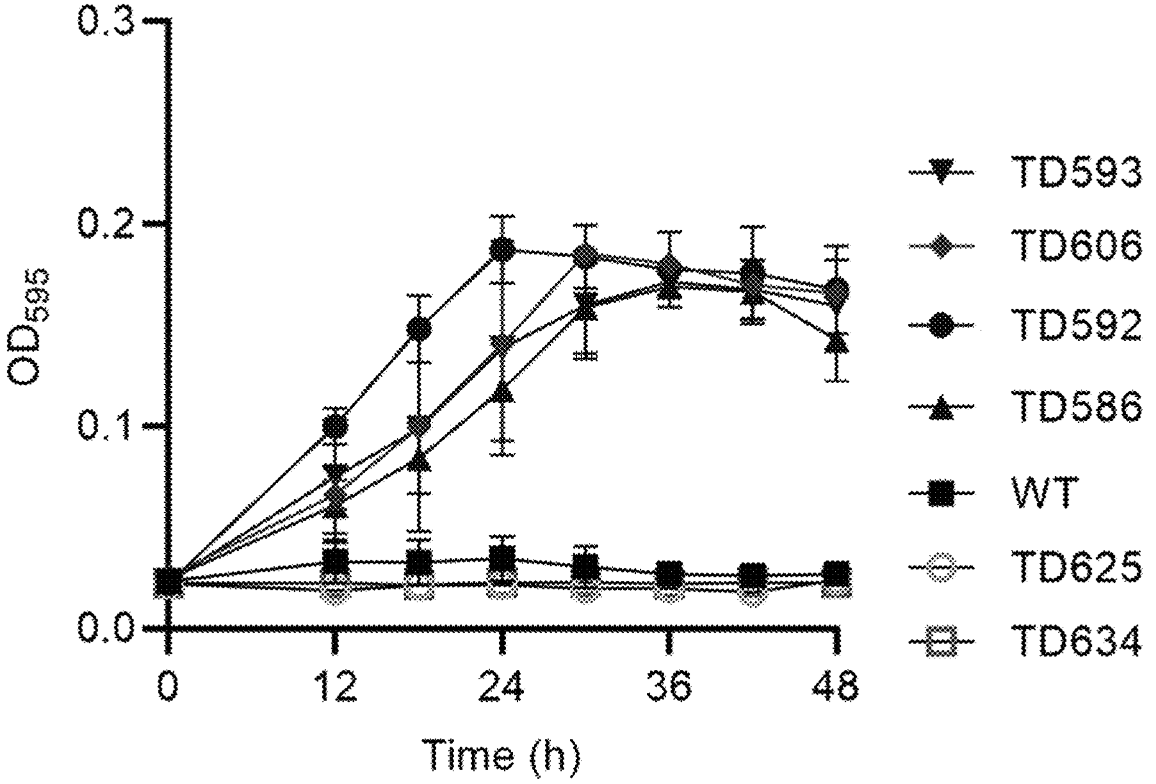
FIG. 3. Growth curves in SMB-acetovanillone (2 mM) of the parent strain (WT), three acetovanillone-evolved isolates (TD586, TD592, TD593), the parent strain with an E16K substitution in Saro_1862 (TD606), TD606 with a deletion of Saro_1861 (TD625), TD606 with a deletion of Saro_1858 (TD634). Datapoints represent mean±SD of three biological replicates.

Analysis of the sequenced genomic DNA revealed one mutation that was shared by all 12 isolated colonies that were generated during adaptive laboratory evolution for growth on acetovanillon. This single nucleotide change is predicted to alter the coding sequence of Saro_1862 and lead to a glutamate (E) to lysine (K) amino acid change at residue 16 (E16K) of this previously uncharacterized protein. To test the role of this mutation in acetovanillone metabolism in the evolved strains, we introduced the same single nucleotide mutation into the genome of the parent strain by homologous recombination to create strain TD606. We found that strain TD606 was able to grow on acetovanillone as a sole carbon source, comparable with evolved strains (FIG. 3). This shows that the E16K substitution in the predicted Saro_1862 protein is both necessary and sufficient to confer acetovanillone metabolism to the parent *N. aromaticivorans* strain.

Saro_1862 is Part of a Predicted Acetovanillone Metabolism Operon

One additional feature of the Saro_1862 mutation that was identified in each of the evolved strains is that this gene is predicted to be part of a transcription unit that encodes homologs of acvCDEFIhpeCBAD genes that were recently reported to be involved in acetovanillone metabolism in *Sphingobium* sp. SYK-6 and *R. rhodochrous* GD02, respectively (20,21). Thus, we hypothesized that these homologs of acvCDEFIhpeCBAD might play the same role in acetovanillone metabolism in *N. aromaticivorans*. To test this hypothesis, we created *N. aromaticivorans* strains lacking the homologs of acvC/hpeC (Saro_1861) and acvF/hpeD (Saro_1858) in the acetovanillone-metabolizing TD606 strain. Consistent with their predicted role in acetovanillone metabolism, we found that these mutant strains (TD625 lacking Saro_1861 and TD634 lacking Saro_1858) could no longer grow on acetovanillone as a sole carbon source (FIG. 3). This data supports the hypothesis that the *N. aromaticivorans* homologs of acvCDEF/hpeCBAD, encoded by Saro_1861-1858, function in a pathway for acetovanillone metabolism similar to that present in *Sphingobium* sp. SYK-6 and *R. rhodochrous* GD02. In these other organisms, homologs of Saro_1861-1858 catalyze later steps of acetovanillone metabolism. Based on this and other information below, we propose that the Saro_1862 protein catalyzes an early step in acetovanillone metabolism. Since homologs of Saro_1862 have yet to be analyzed, we performed a series of experiments to explain how the E16K amino acid substitution in this protein leads to acetovanillone metabolism.

Saro_1862 is a Previously Uncharacterized Acetovanillone Kinase

Two observations provided hints at the function of Saro_1862 in *N. aromaticivorans* acetovanillone metabolism. First, the predicted *N. aromaticivorans* Saro_1858-1862 transcription unit lacks genes predicted to encode subunits of the heterodimeric acetovanillone kinases AcvAB/HpeHI. In addition, Saro_1862 is annotated in NCBI to encode a protein with a Tm-1-like ATP binding domain. Thus, we hypothesized that the Saro_1862 E16K protein could be a previously unknown acetovanillone kinase that uses ATP to phosphorylate this aromatic. To test this hypothesis, we expressed and purified the *N. aromaticivorans* Saro_1862 E16K variant protein and incubated it with acetovanillone and ATP in vitro. HPLC-MS analysis of this reaction mixture showed the disappearance of acetovanillone and the accumulation of a compound with a m/z ratio corresponding to phosphorylated acetovanillone (FIG. 4 (A)). No formation of this reaction product was observed in control assays lacking enzyme or ATP (FIG. 4 (D-E)). From this, we conclude that the *N. aromaticivorans* Saro_1862 E16K protein is a previously uncharacterized acetovanillone kinase.

Figure 4:
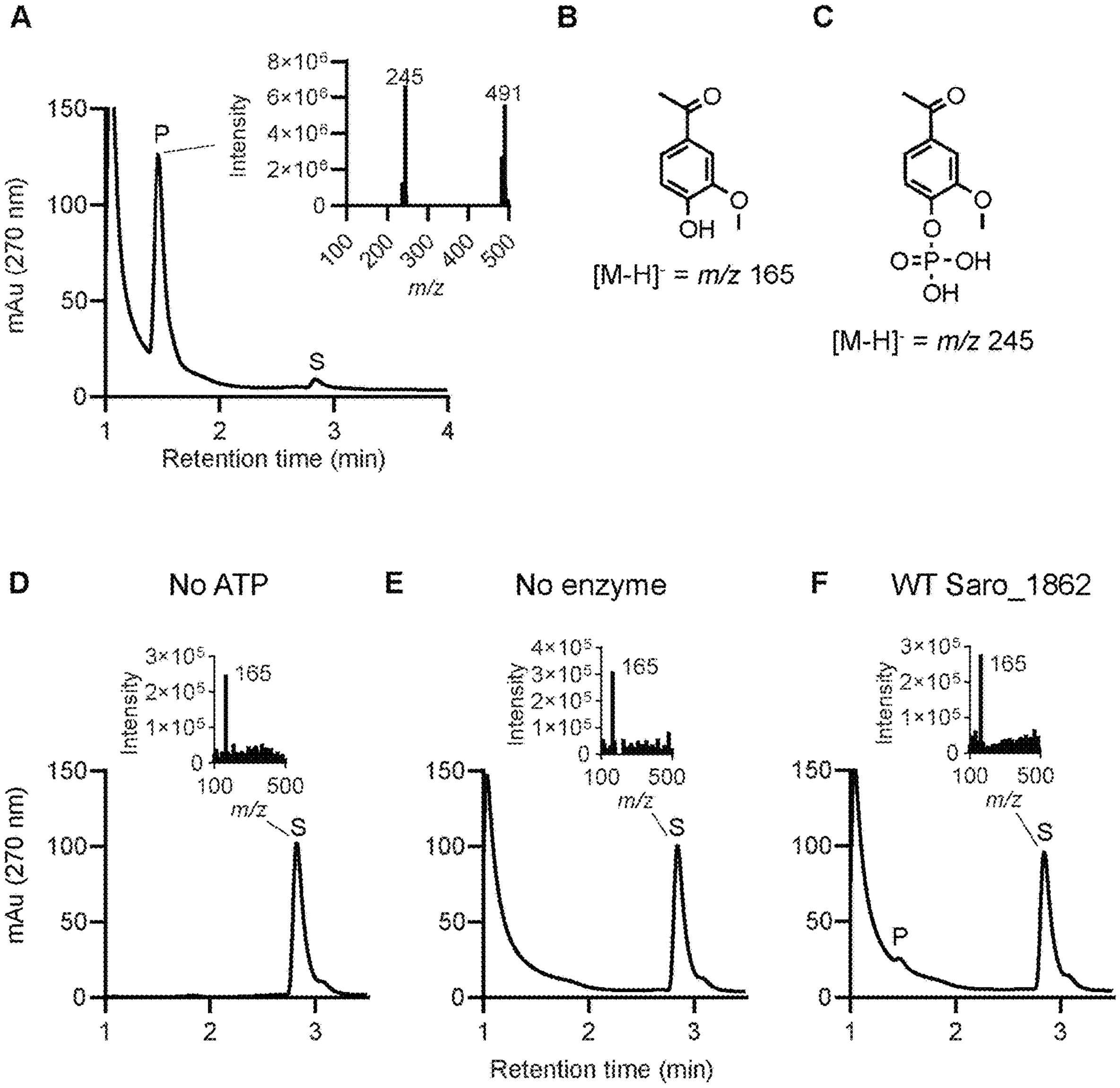
FIG. 4. The Saro_1862 E16K variant phosphorylates acetovanillone in an ATP-dependent manner. A, HPLC-MS analysis of an in vitro reaction mixture containing 200 μM acetovanillone, Saro_1862 E16K, and ATP following a 1 h incubation at 30° C. The inset shows a negative mode mass scan from 100 to 500 m/z of the peak identified by HPLC. P and S denote product and substrate, respectively, identified by retention time, absorbance, and mass scans. B, chemical structure and expected m/z of acetovanillone. C, chemical structure and expected m/z of phosphorylated acetovanillone. D, HPLC-MS analysis of the Saro_1862 E16K in vitro reaction mixture without ATP. E, HPLC-MS analysis of the Saro_1862 E16K in vitro reaction mixture without Saro_1862. F, HPLC-MS analysis of the in vitro reaction mixture using the wild-type Saro_1862 enzyme.

As a control, we expressed and purified the Saro_1862 protein from the wild type *N. aromaticivorans* DSM12444 strain and detected a greatly reduced level of acetovanillone phosphorylation under identical reaction conditions (FIG. 4 (F)). Combined, these results support the hypothesis that the E16K variant of Saro_1862, which is present in TD606 and in the evolved strains that can metabolize acetovanillone, phosphorylates acetovanillone in vivo.

To make a direct comparison of Saro_1862 E16K acetovanillone kinase activity to the reported activity of the *R. rhodochrous* GD02 heterodimeric acetovanillone kinase HpeHI, we tested the activity of the variant protein using the spectrophotometric assay that measures conversion of acetovanillone to phospho-acetovanillone described in (21). Under comparable reaction conditions, the Saro_1862 E16K protein phosphorylated acetovanillone at a rate (+SD) of 64±5 min−1 (n=3 preparations of Saro_1862 E16K, FIG. 5). In contrast, the Saro_1862 wild type protein phosphorylated acetovanillone at a rate of 0.041±0.003 min−1 (n=3 technical replicates), consistent with the greatly reduced acetovanillone phosphorylation seen in FIG. 4F. The observed rate of acetovanillone phosphorylation by the recombinant Saro_1862 E16K protein is more than an order of magnitude higher than the value of 4.1±0.4 min-1 reported for the heterodimeric HpeHI protein (21). The rate of acetovanillone phosphorylation by AcvAB was measured using different reaction conditions and crude enzyme extracts, but reported similar rate measurements to those reported for HpeHI (20). Results are shown in Table 3:

TABLE 3

Comparison of acetovanillone phosphorylation rates (±SD) with WT Saro_1862, Saro_1862-E16K, and HpeHI*

| Kinase | Rate ($min^{-1}$) | Relative |
|---|---|---|
| WT Saro_1862 | 0.04 ± 0.01 | 1 |
| Saro_1862-E16K | 64 ± 5 | ~1600 |
| HpeHI | 4.1 ± 0.4 | ~100 |

*Heterodimeric *Rhodococcus rhodocrous* acetovanillone kinase (Dexter et al. 2022 (21))

Saro_1862-E16K had ~1600 fold higher rate of acetovanillone phosphorylation than wild type Saro_1862. Saro_1862-E16K phosphorylation rate was ~16-fold higher than HpeEI from *Rhodococcus rhodocrous*.

Figure 6:
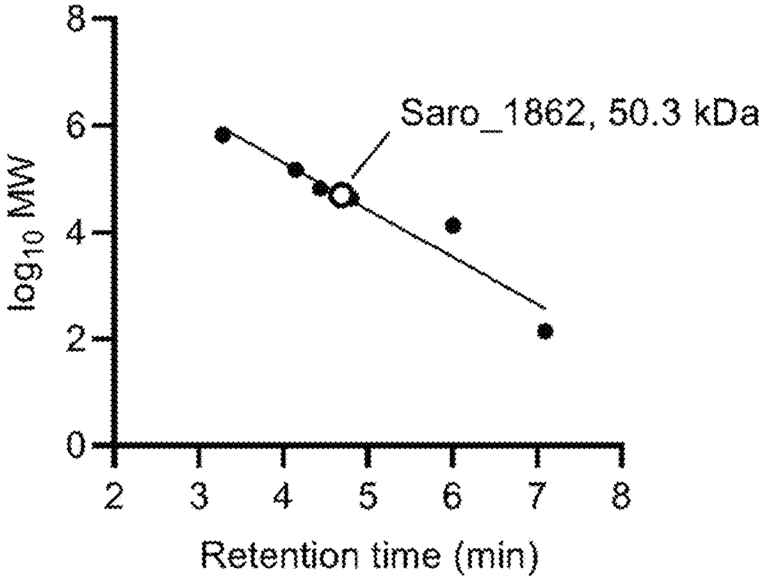
FIG. 6. Size exclusion chromatography of recombinant Saro_1862 E16K. A linear fit of molecular weight (MW) standards was used to calculate the apparent MW of Saro_1862 E16K as 50.3 kDa.

To investigate the Saro_1862 native oligomeric state, we analyzed pure Saro_1862 E16K samples alongside a protein standard mix using size exclusion chromatography. This analysis resulted in a predicted native molecular weight of 50.3 kDa (FIG. 6), close to the predicted molecular weight of the Saro_1862 E16K monomer (42.6 kDa). Thus, this result predicts that the Saro_1862 kinase is a monomer.

Figure 7:
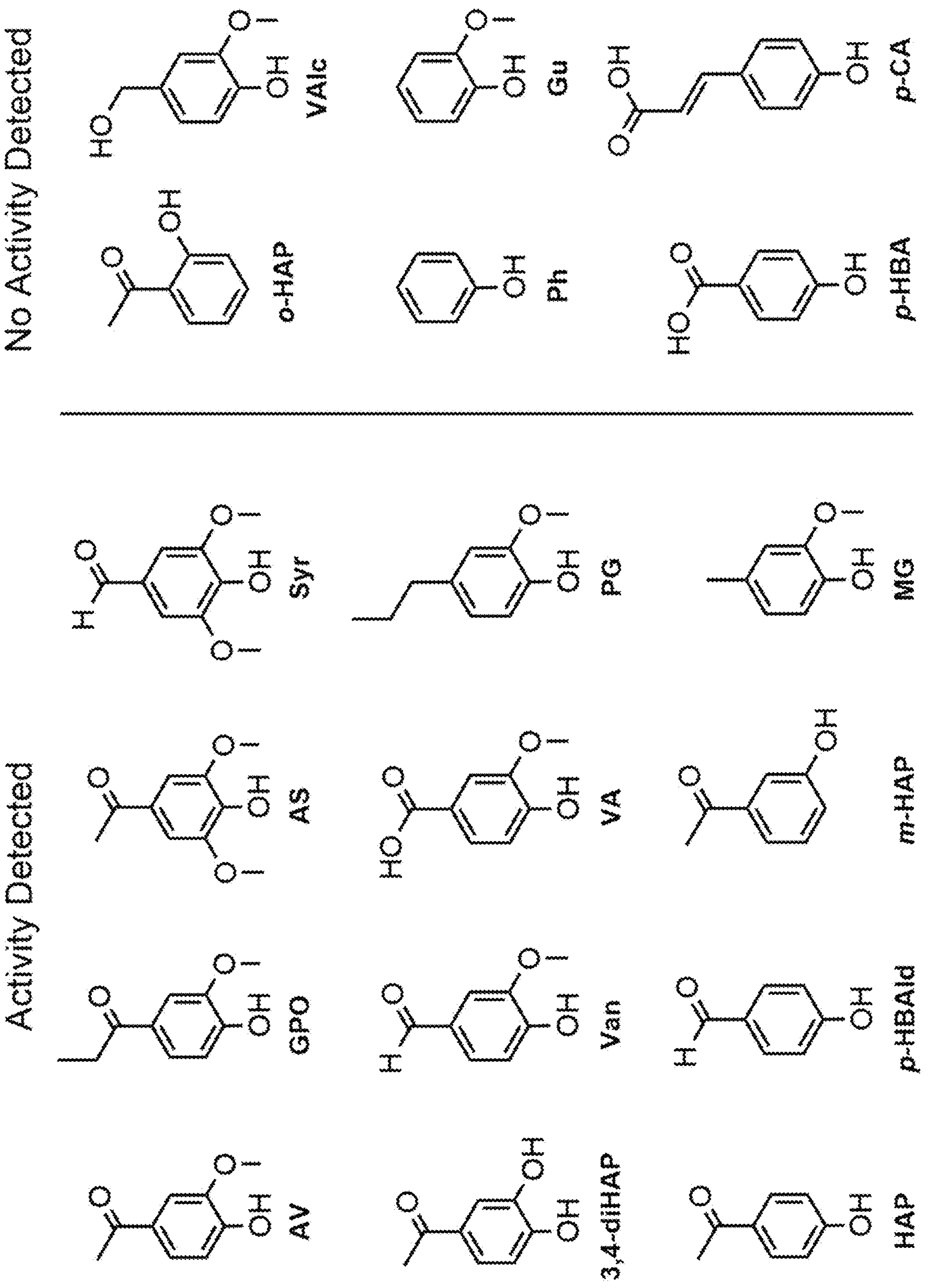
FIG. 7. The Saro_1862 E16K variant enzyme phosphorylates a variety of S, G, and H aromatic monomers that contain ketone or aldehyde side chains. Activity was detected using HPLC-MS (FIGS. 13-29). AV, acetovanillone; GPO, guaiacylpropanone; 3,4-diHAP, 3,4-dihydroxyacetophenone; Van, vanillin; HAP, p-hydroxyacetophenone; p-HBAld, p-hydroxybenzaldehyde; AS, acetosyringone; Syr, syringaldehyde; m-HAP, m-hydroxyacetophenone; VA, vanillic acid; VAlc, vanillyl alcohol; MG, methylguaiacol; Ph, phenol; Gu, guaiacol; o-HAP, o-hydroxyacetophenone; PG, propylguaiacol; p-HBA, p-hydroxybenzoic acid; p-CA, p-coumaric acid.

Saro_1862 E16K Phosphorylates a Variety of Aromatic Ketones and Aldehydes In Vitro As Saro_1862 represents a previously uncharacterized kinase, we sought to determine if it can phosphorylate other monomers that could be relevant for the metabolism of biomass-derived aromatics by *N. aromaticivorans*. Using the same reaction conditions as for acetovanillone (FIG. 4), we tested for in vitro activity of the Saro_1862 E16K variant enzyme with equal concentrations of a number of chemically-related aromatic compounds, including multiple representatives from the three major syringyl(S), guaiacyl (G), and p-hydroxyphenyl (H) monomers found in lignin (FIG. 7). This analysis showed that the Saro_1862 E16K variant phosphorylates all three types of aromatic monomers, although we observed incomplete substrate conversion for syringyl substrates following the 1 h in vitro incubation used for these studies (FIGS. 13-29). After comparing the results of these assays, it appears that Saro_1862 E16K has a preference for phosphorylation of aromatic substrates with a ketone or aldehyde side chain.

Figure 8:
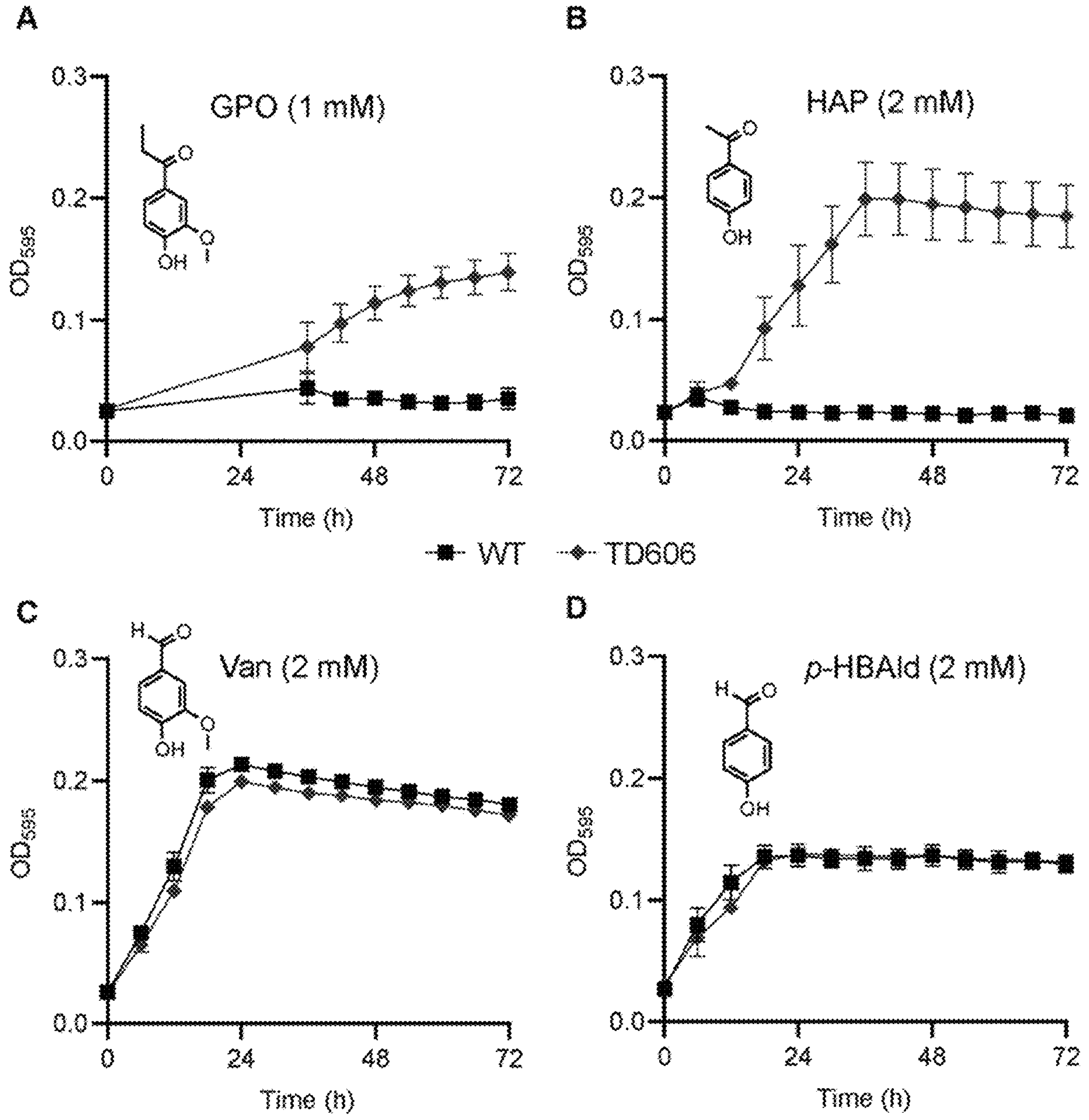
FIG. 8. The Saro_1862 E16K variant is required for GPO and HAP metabolism in vivo. Growth curves show the *N. aromaticivorans* parent strain (WT, black squares) and the parent strain with the Saro_1862 E16K mutation (TD606, red diamonds) growing on different substrates of Saro_1862 E16K from FIG. 5. GPO, guaiacylpropanone; HAP, p-hydroxyacetophenone; Van, vanillin; p-HBAld, p-hydroxybenzaldehyde.
Figure 9:
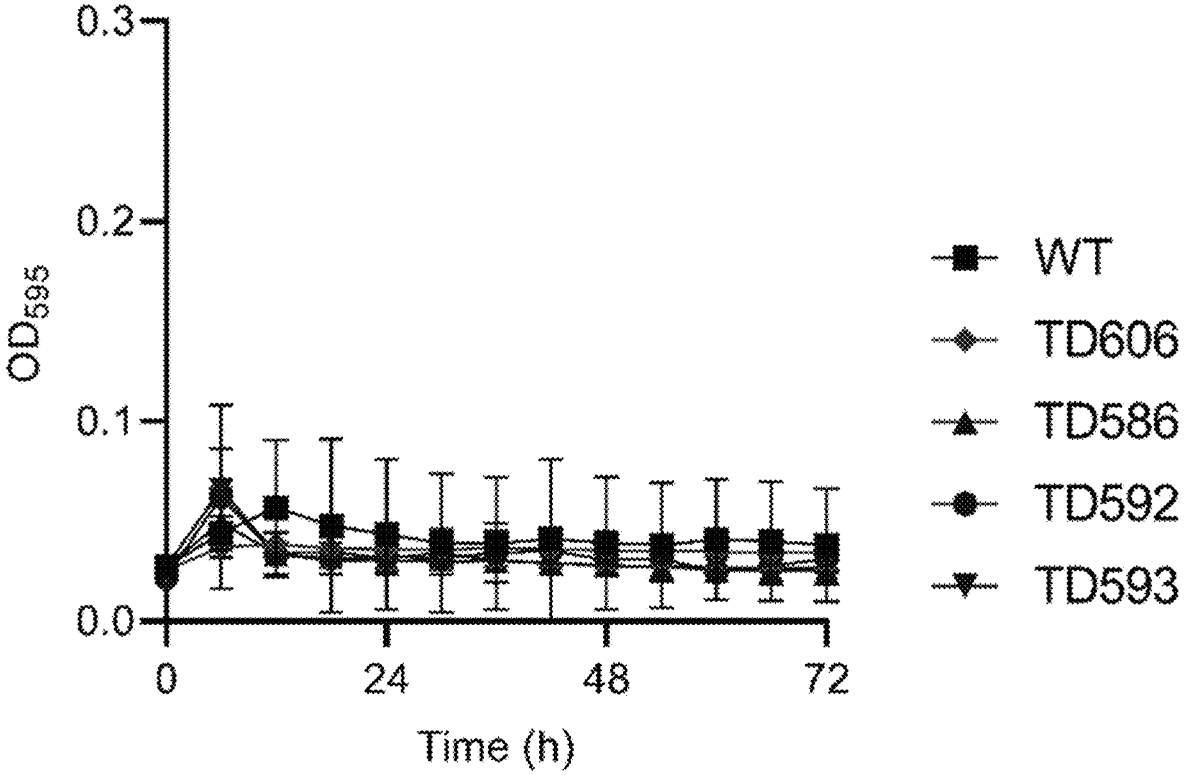
FIG. 9. No growth is detected when the parent strain (WT), the parent strain with an E16K substitution in Saro_1862 (TD606), and three acetovanillone-evolved isolates (TD586, 592, and 593) are grown in SMB-acetosyringone (1 mM). Datapoints represent mean±SD of three biological replicates.

Based on the results of these in vitro assays, we tested the *N. aromaticivorans* DSM12444 parent strain and TD606 for growth on some of the aromatics that were phosphorylated by Saro_1862 E16K. This analysis showed that cells containing the Saro_1862 E16K variant (TD606), but not the *N. aromaticivorans* parent, were able to grow with guaiacylpropanone and p-hydroxyacetophenone as the sole carbon source (FIG. 8 (A-B)). We also found that growth with vanillin and p-hydroxybenzaldehyde as the sole carbon source was similar in both the parent strain and in TD606 (FIG. 8 (C-D)), suggesting that the single amino acid change in Saro_1862 E16K does not have a significant impact on utilization of these two aromatic substrates as sole carbon sources. In addition, although we detected phosphorylation of acetosyringone by Saro_1862 E16K (FIG. 19), we did not detect significant growth of the evolved strains or TD606 in SMB media containing 1 mM acetosyringone as the sole carbon source (FIG. 9). Overall, these results lead us to conclude that the Saro_1862 E16K variant is also involved in or required for metabolism of several of the aromatic substrates in vivo that it was shown to phosphorylate in vitro.

Presence of Saro_1862 Homologs in Bacteria Predicted to Encode Acetovanillone Metabolism Genes The discovery of Saro_1862 as a newly identified aromatic kinase prompted us to ask if homologs of this protein are present in other bacteria that are predicted to encode acetovanillone metabolism genes. To answer this question, we searched for bacterial genomes that contained a Saro_1862 homolog as well as homologs of acvCDEF and vceAB or hpeCBAD and hpeEF that are reported to be required for acetovanillone metabolism in *Sphingobium* sp. SYK-6 and *R. rhodochrous* GD02, respectively (20,21). We also searched for bacterial genomes that contained acvAB or hpeHI homologs as the predicted acetovanillone kinase along with the other known acetovanillone metabolism genes above. After searching 17,510 genomes in the NCBI representative prokaryotic genome database (downloaded Sep. 12, 2023), we found that more predicted acetovanillone-metabolizing species contain genes encoding AcvAB/HpeHI kinase homologs (n=570) (Table 5, which shows species that encode homologs of AcvAB or HpeHI, AcvC or HpeC, AcvD or HpeB, AcvE or HpeA, AcvF or HpeD, VceA or HpeE, and VceB or HpeF) compared to ones that encode a Saro_1862 kinase homolog (n=266) (Table 4, which shows species that encode homologs of Saro_1862, AcvC or HpeC, AcvD or HpeB, AcvE or HpeA, AcvF or HpeD, VceA or HpeE, and VceB or HpeF). In addition, this analysis predicts that 179 of these species encode homologs of both AcvAB/HpeHI and Saro_1862 (Table 6), suggesting that some bacteria contain two enzymes that could potentially phosphorylate acetovanillone or structurally related substrates. Table 7 shows homologs of Saro_1862 regardless of the predicted acetovanillone-metabolizing ability of the organism containing it. Table 8 shows summaries of the numbers of types of organisms presented in Tables 4 and 5.

TABLE 8

Summaries of the numbers of types of organisms presented in Tables 4 and 5.

| From Table 4 | | From Table 5 | |
|---|---|---|---|
| Organism Type | Number | Organism Type | Number |
| Actinomycetota | 105 | Actinomycetota | 292 |
| Alphaproteobacteria | 84 | Alphaproteobacteria | 61 |
| Bacillota | 28 | Aquificae | 2 |
| Bacteroidota/ Chlorobiota group | 5 | Bacillota | 120 |
| Betaproteobacteria | 6 | Bacteroidota/ Chlorobiota group | 8 |
| Chloroflexota | 1 | Betaproteobacteria | 15 |
| Desulfuromonadia | 1 | Desulfuromonadia | 1 |
| Gammaproteobacteria | 4 | Epsilonproteobacteria | 1 |
| Planctomycetota | 30 | Gammaproteobacteria | 42 |
| Thermomicrobiota | 1 | Nitrospiria | 1 |
| Verrucomicrobiota | 1 | Planctomycetota | 25 |
| | | Thermomicrobiota | 2 |

Figure 10:
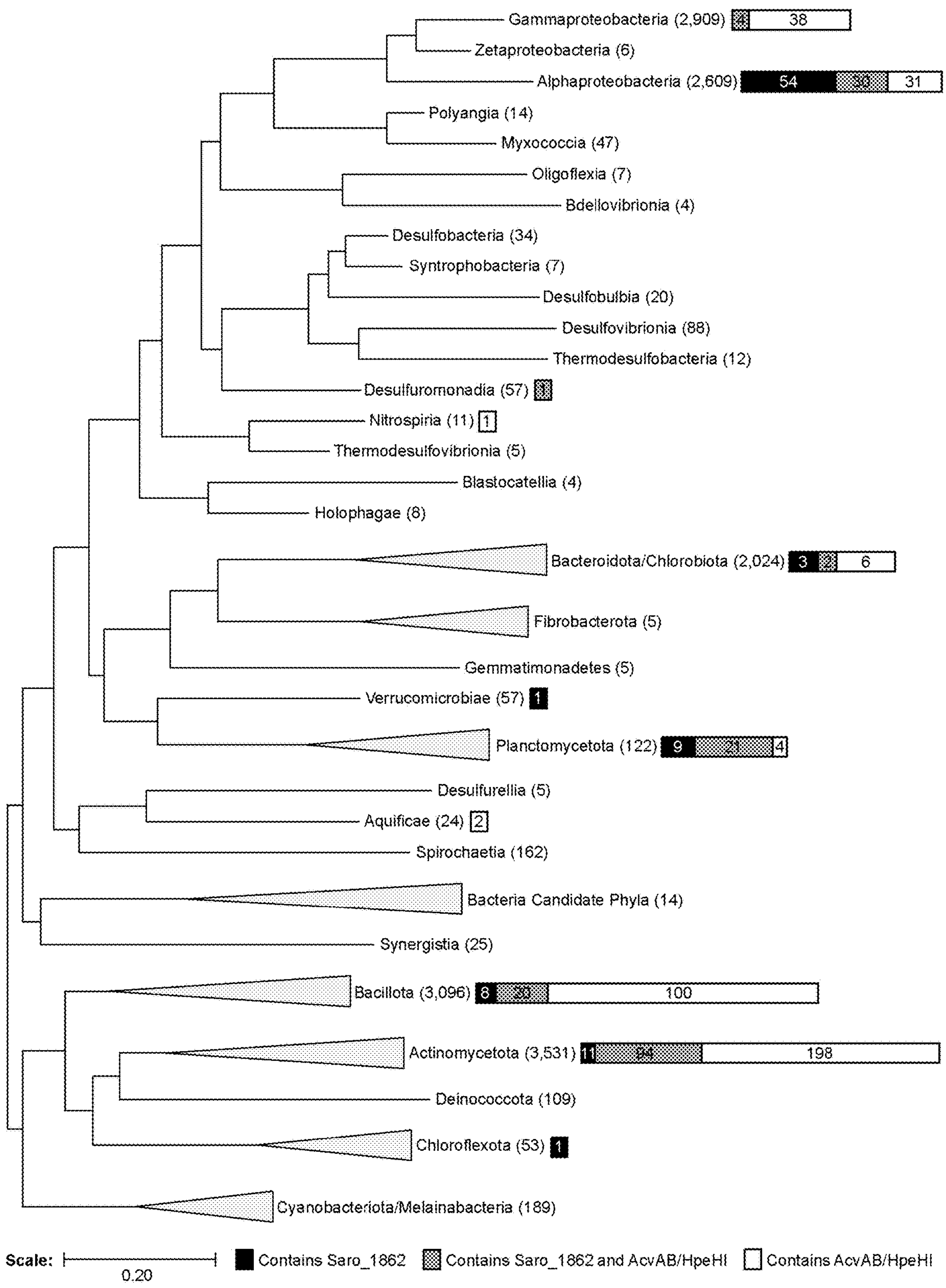
FIG. 10. Predicted prevalence of acetovanillone metabolism genes across bacteria. The bacterial tree of life was obtained from AnnoTree (41) and edited to reflect the subgroups from the NCBI representative prokaryotic genomes database. Some classes are collapsed into phyla and shown as triangles. Numbers next to each clade name denote how many representative species are in that clade in the NCBI database that was searched. Horizontal bars next to clades denote the number of species within that clade that contain a full set of acetovanillone metabolism homologs; black bars denote species that encode a Saro_1862 kinase homolog with all other genes, grey bars denote species that encode both Saro_1862 and AcvAB/HpeHI homologs with all other genes, and white bars denote species that encode AcvAB/HpeHI homologs with all other genes. Full species lists and BLAST hits are included in Tables 3-7 and otherwise as described below.

The results of this analysis also predict that the presence of genes potentially involved in acetovanillone metabolism is not limited to a particular clade of the bacterial phylogeny (FIG. 10). The search found that genes encoding homologs of known acetovanillone metabolism enzymes are more prevalent in the genomes of Gram-positive species, such as Actinomycetota and Bacillota groups, although this may be due to greater numbers of searched genomes in these groups. In addition, while this analysis predicts that AcvAB/HpeHI kinase homologs are more prevalent than Saro_1862 homologs in general, the genomes of Alphaproteobacteria more often contain genes that encode a Saro_1862 homolog than homologs of the heterodimeric AcvAB/HpeHI aromatic kinases (FIG. 10).

DISCUSSION

This work sought to expand our knowledge of the aromatic substrate utilization capabilities of *N. aromaticivorans* DSM12444. Acetovanillone is an aromatic monomer recovered directly or indirectly in significant amounts from several biomass depolymerization methods, but it cannot be used as a sole carbon source by this strain of *N. aromaticivorans* (14). This work used adaptive laboratory evolution of *N. aromaticivorans* DSM12444 to generate strains that can metabolize acetovanillone. Genomic analyses identified a single mutation necessary for growth in the presence of acetovanillone in Saro_1862, which led to the biochemical and genetic characterization of this protein as a previously uncharacterized aromatic kinase.

Saro_1862 Represents a Previously Uncharacterized Class of Kinase

Saro_1862 is annotated in NCBI as a Tm-1-like ATP-binding domain-containing protein. However, biochemical studies of Tm-1 have yet to report kinase activity (23). In addition, the UPF0261 domain within Saro_1862 has no other biochemical characterization other than as a homolog of Tm-1. Saro_1862 is not homologous to either of the subunits of the known heterodimeric acetovanillone kinases AcvAB/HpeHI. In addition, an AlphaFold predicted structure of Saro_1862 (24) does not have significant similarity to other known kinases, according to the DALI Protein Structure Comparison Server (25). Thus, it appears that Saro_1862 represents a previously uncharacterized member of the kinase protein family.

Figure 11:
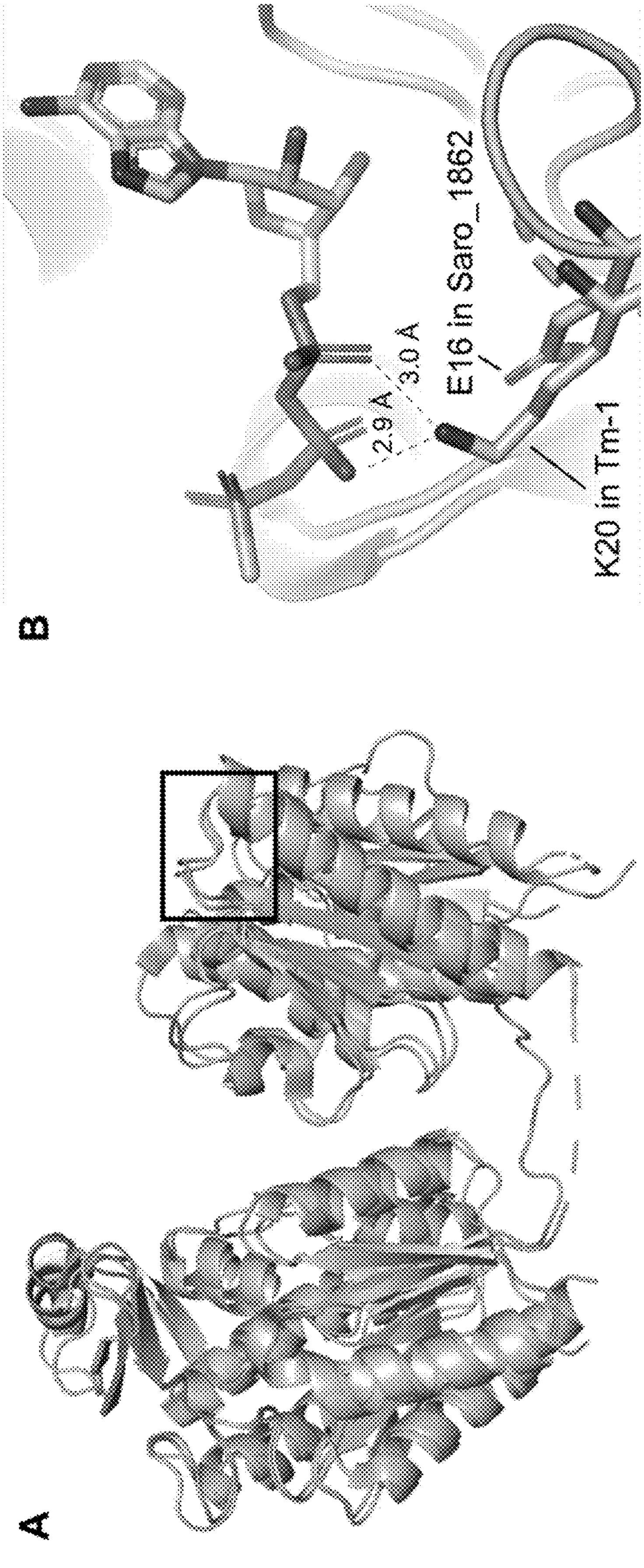
FIG. 11. A, Superposition of the AlphaFold model of Saro_1862 (green) with the known 3-dimensional structure of Tm-1 (gray, PDB: 3WRX; RMSD=1.55 Å). The black box shows the area depicted in the following panel. B, Comparison of the known structure of the Tm-1 ATP binding site with the model of Saro_1862 indicates that the E16 residue in *N. aromaticivorans* Saro_1862 likely interferes with ATP binding. For comparison, Tm-1 residue K20, which corresponds to E16 in Saro_1862, makes side chain contacts with the bound ATPyS.

Predicted Mechanism for how the Saro_1862 E16K Amino Acid Change Allows Aromatic Phosphorylation The ability of the single E16K amino acid change in Saro_1862 to enable kinase activity suggests this residue plays an important role in catalysis. To investigate a possible role for this residue in enzyme function, we superimposed the AlphaFold (24) predicted structure of Saro_1862 onto the ATPγS-bound structure of Tm−1 (PDB: 3WRX). This alignment showed that E16 in Saro_1862 corresponds to K20 in Tm−1, which makes contacts with the phosphate groups of bound ATPγS (FIG. 11). Thus, it is likely that the E16K mutation in Saro_1862 increases kinase activity of the enzyme by promoting protein contacts with ATP in the active site region of this protein. Lysine residues are known to be important for catalysis of many kinase family members (26-29), so it is not surprising that the E to K amino acid change at position 16 of Saro_1862 increases the ability of this protein to phosphorylate acetovanillone.

We also found that the glutamate variant at this position (E16) in *N. aromaticivorans* DSM12444 is rare, which is consistent with this residue's importance in catalysis. Among all of the Saro_1862 homologs in *Novosphingobium* species in the NCBI representative prokaryotic genomes database, Saro_1862 from *N. aromaticivorans* DSM12444 is the only protein that encodes a glutamate (E) at position 16. All other sequenced *Novosphingobium* spp. are predicted to encode a lysine (K) at the corresponding position of their Saro_1862 homolog, so they would be predicted to have the ability to phosphorylate acetovanillone.

Importance of Saro_1862 in Metabolism of Lignin-Derived Aromatics

Our results show that Saro_1862 E16K phosphorylates S-, G-, and H-type aromatics in vitro, and it prefers substrates that contain ketone and aldehyde side chains. Our results further show that Saro_1862 E16K is important for metabolism of some of these compounds in vivo, such as acetovanillone, guaiacylpropanone, and p-hydroxyacetophenone (FIG. 3, FIG. 8). Combined, these results predict that Saro_1862-mediated phosphorylation is important to initiate metabolism of several lignin-derived aromatics that could be derived from oxidative depolymerization methods (3,8-13). In addition, *N. aromaticivorans* has been shown to transform ethyl- and propyl-substituted aromatics resulting from reductive lignin depolymerization into their corresponding ketones, such as acetovanillone, acetosyringone, guaiacylpropanone, and syringylpropanone (14). Thus, the kinase activity of Saro_1862 E16K is likely necessary for utilization of lignin aromatics derived from reductive depolymerization methods as well. In fact, propyl-substituted aromatics have been found to be more than twice as abundant as ethyl-substituted aromatics in reductively depolymerized biomass (14), suggesting that the ability of the Saro_1862 E16K mutant to metabolize guaiacylpropanone is more important for complete utilization of these depolymerized lignin streams than the ability to metabolize acetovanillone.

We did not detect significant growth of the evolved strains or TD606 in SMB media containing 1 mM acetosyringone as the sole carbon source (FIG. 9). Because *N. aromaticivorans* DSM12444 is able to use syringic acid as a sole carbon source (15), a predicted intermediate in acetosyringone metabolism (20), we hypothesized that our evolved strains and TD606 would be able to grow on acetosyringone as a sole carbon source. S-type aromatics such as acetosyringone are often more prevalent than G-type aromatics such as acetovanillone in depolymerized lignin from hardwood biomasses known to have high S: G ratios (10,14). One potential explanation for the inability of TD606 to grow on acetosyringone as a sole carbon source could be the lack of sufficient activity of the enzymes in the *N. aromaticivorans* DSM12444 acetovanillone metabolic pathway with phosphorylated acetosyringone or subsequent intermediates. Thus, additional studies are needed to determine why cells containing Saro_1862 E16K are unable to grow in the presence of acetosyringone.

On the other hand, other aromatics, namely vanillin and p-hydroxybenzaldehyde, were phosphorylated by Saro_1862 E16K in vitro but did not require Saro_1862 E16K for in vivo metabolism (FIG. 8 (C-D)). This result is not surprising, since previous studies did not predict a role for the Saro 1858-1862 transcription unit or the acvABCDEF transcription unit in *Sphingobium* sp. SYK-6 in metabolism of vanillin and p-hydroxybenzaldehyde (19,30). Instead, these aromatics are known to be oxidized to vanillic acid and p-hydroxybenzoic acid, respectively, via other enzymes before entry into central aromatic metabolism (19,30). This suggests that, although aldehyde-containing aromatics are substrates of Saro_1862 E16K, only ketone-containing aromatics require phosphorylation for their complete metabolism. It is possible that this difference reflects a need to phosphorylate ketone-containing aromatics to facilitate their subsequent decarboxylation, as is the case for acetovanillone (20,21).

Phosphorylation of Aromatics by Saro_1862

Although they are not homologous, our data predict that Saro_1862 and AcvAB/HpeHI play a similar role in acetovanillone phosphorylation. Comparisons of published data on aromatic phosphorylation by AcvAB (20) with our data from Saro_1862 E16K (FIG. 7) show that these kinases are active with similar substrates. However, AcvAB appears to phosphorylate acetosyringone more efficiently than acetovanillone, while the opposite is true for Saro_1862 (see Table S3 in (20)). In addition, AcvAB showed detectable phosphorylation of guaiacol (20), which was not detected for Saro_1862, although phosphorylation of guaiacol is not expected to be necessary for metabolism of this aromatic (31,32).

Despite having similar substrate specificities, Saro_1862 E16K phosphorylates acetovanillone at a rate more than an order of magnitude higher than the value reported for the heterodimeric HpeHI protein (21). In addition, the function of Saro_1862 as a single subunit enzyme removes the need to balance levels of multiple gene products for future analyses of aromatic kinase activity. These properties of Saro_1862 predict that heterologous expression of acetovanillone metabolism genes in other bacteria may benefit from using Saro_1862 E16K as the acetovanillone kinase, compared to one of the heterodimeric acetovanillone kinases.

Predicted Acetovanillone Kinases Among Bacteria

After searching for acetovanillone metabolism genes across the bacterial tree of life (FIG. 10), we found that homologs of these genes are found in multiple highly divergent clades. In particular, we found that AcvAB/HpeHI and Saro_1862 homologs were distributed across the bacterial phylogeny. This analysis also revealed that many bacterial genomes contained homologs of both AcvAB/HpeHI and Saro_1862, opening the possibility that these organisms can use different kinases to increase the number and types of aromatic substrates that can be phosphorylated and possibly metabolized.

CONCLUSION

In this work, we used adaptive laboratory evolution to create strains of *N. aromaticivorans* DSM12444 capable of metabolizing acetovanillone, an aromatic monomer that results from oxidative lignin depolymerization methods. Genomic analysis of evolved strains identified an E16K amino acid change in Saro_1862 that is both necessary and sufficient for acetovanillone metabolism in *N. aromaticivorans*. Biochemical and genetic characterization of Saro_1862 reveal it is a previously uncharacterized type of kinase that phosphorylates aromatic monomers, and is required for metabolism of some aromatics with ketone side chains. The single subunit Saro_1862 protein also has some kinetic and biochemical advantages over the unrelated heterodimeric acetovanillone kinases AcvAB/HpeHI, including an order of magnitude greater reaction rate. Homologs of Saro_1862 are found throughout the bacterial phylogeny, highlighting the potential importance of aromatic phosphorylation during metabolism in many organisms.

Materials and Methods

Bacterial Strains and Growth Media

For all experiments, we used the parent strain *N. aromaticivorans* 12444Δ1879 (33), in which the putative sacB gene has been deleted to allow markerless genomic modification by variants of the pK18mobsacB plasmid (34). *N. aromaticivorans* cultures were grown in Standard Mineral Base (SMB) (33) at an initial pH of 7.0, supplemented with indicated carbon sources, and shaken at ~200 rpm at 30° C. For routine growth and manipulation *N. aromaticivorans* strains were grown in SMB+10 mM glucose. Where needed to select for the presence or absence of plasmids, media were supplemented with 50 μg/mL kanamycin or 10% sucrose (w/v).

*Escherichia coli* strains used for cloning and conjugation were grown in lysogeny broth (LB), and shaken at ~200 rpm at 37° C. Strain WM6026 was grown in LB supplemented with 300 μM diaminopimelic acid. Where needed to select for the presence of plasmids, media were supplemented with 50 μg/mL kanamycin.

Adaptive Laboratory Evolution

Figure 12:
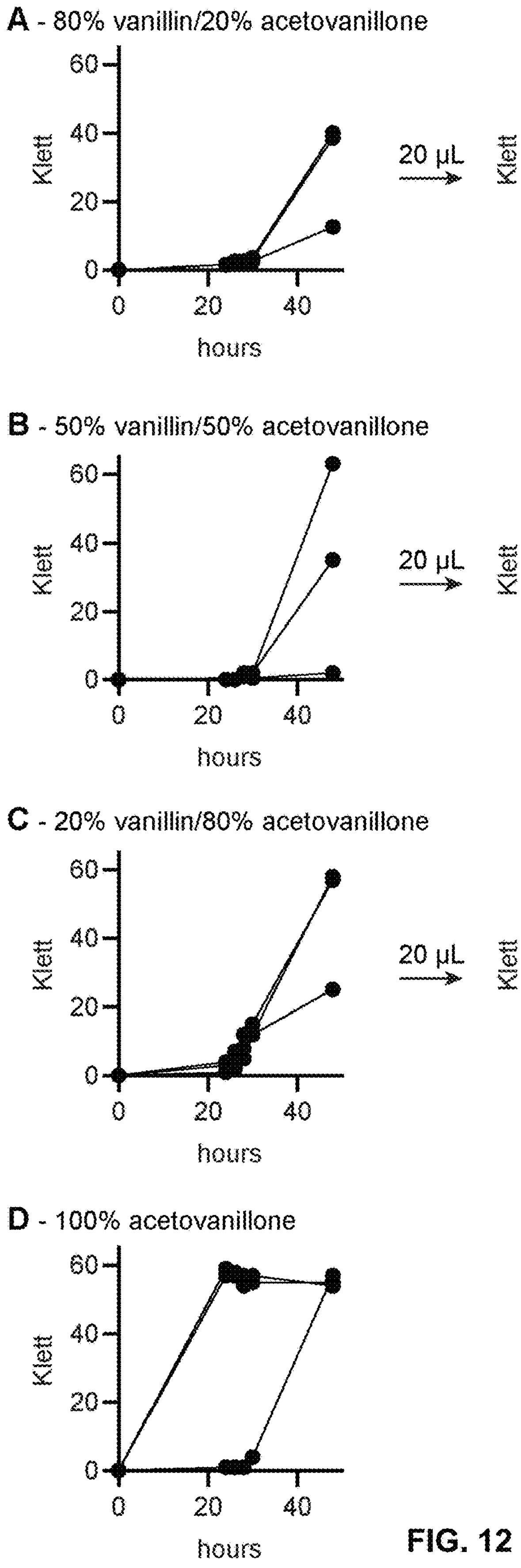
FIG. 12. Growth of *N. aromaticivorans* 1244441879 cultures during adaptive laboratory evolution. Each panel shows the first (left) and second (right) 48 h passage in the designated vanillin/acetovanillone media mixture. An additional 72 h passage was grown at each vanillin/acetovanillone media mixture before increasing the acetovanillone concentration, as described in FIG. 2. Klett measurements were adjusted to initial readings of zero for each new culture. Datapoints show individual replicates connected by lines.
Figure 13:
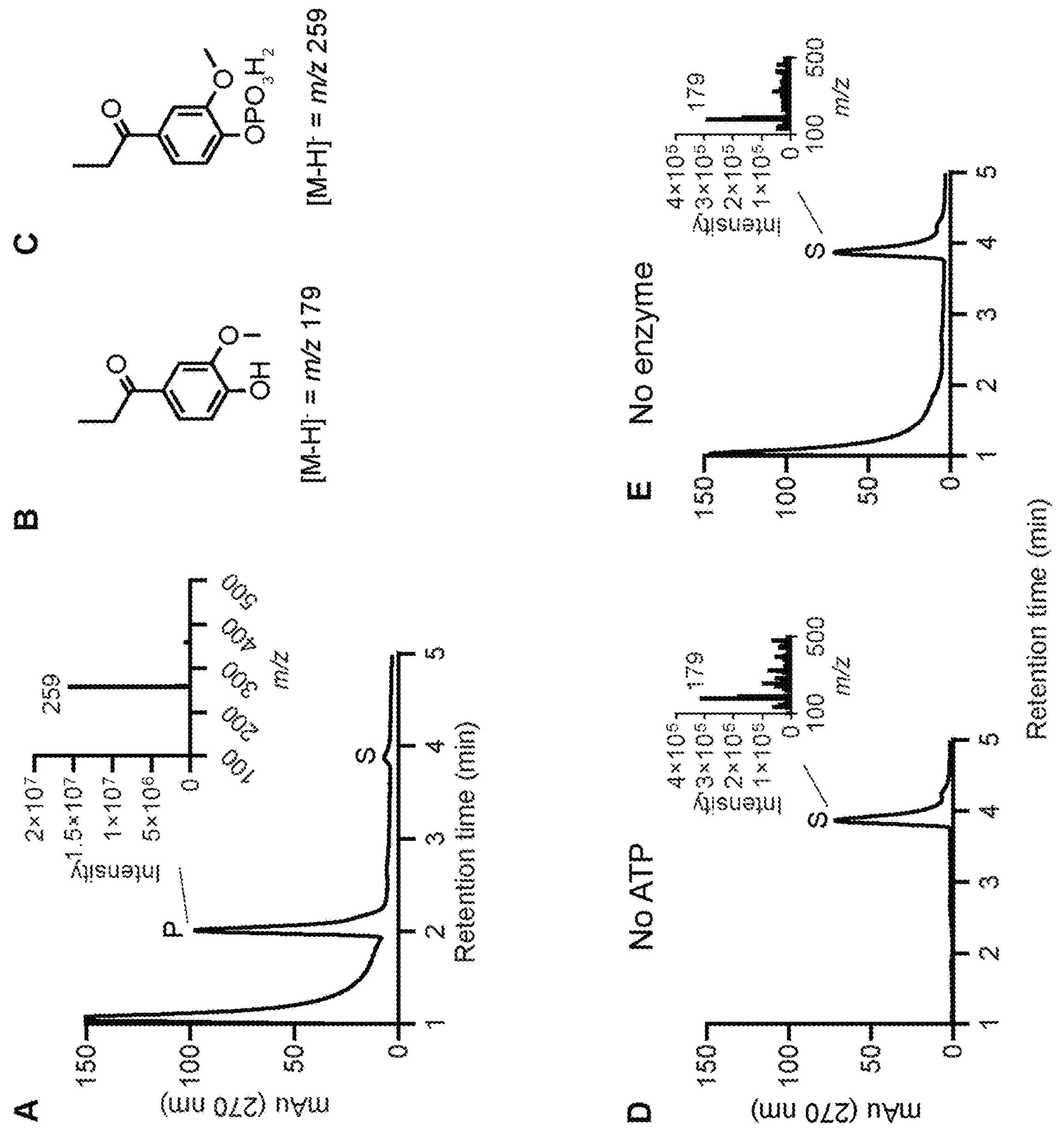
FIG. 13. The Saro_1862 E16K variant phosphorylates guaiacylpropanone in an ATP-dependent manner. A, HPLC-MS analysis of an in vitro reaction mixture containing 200 µM guaiacylpropanone, Saro_1862 E16K, and ATP following a 1 h incubation at 30° C. The inset shows a negative mode mass scan from 100 to 500 m/z of the peak identified by HPLC. P and S denote product and substrate, respectively, identified by retention time, absorbance, and mass scans. B, chemical structure and expected m/z of guaiacylpropanone. C, chemical structure and expected m/z of phosphorylated guaiacylpropanone. D, HPLC-MS analysis of the Saro_1862 E16K in vitro reaction mixture without ATP. E, HPLC-MS analysis of the Saro_1862 E16K in vitro reaction mixture without Saro_1862.
Figure 14:
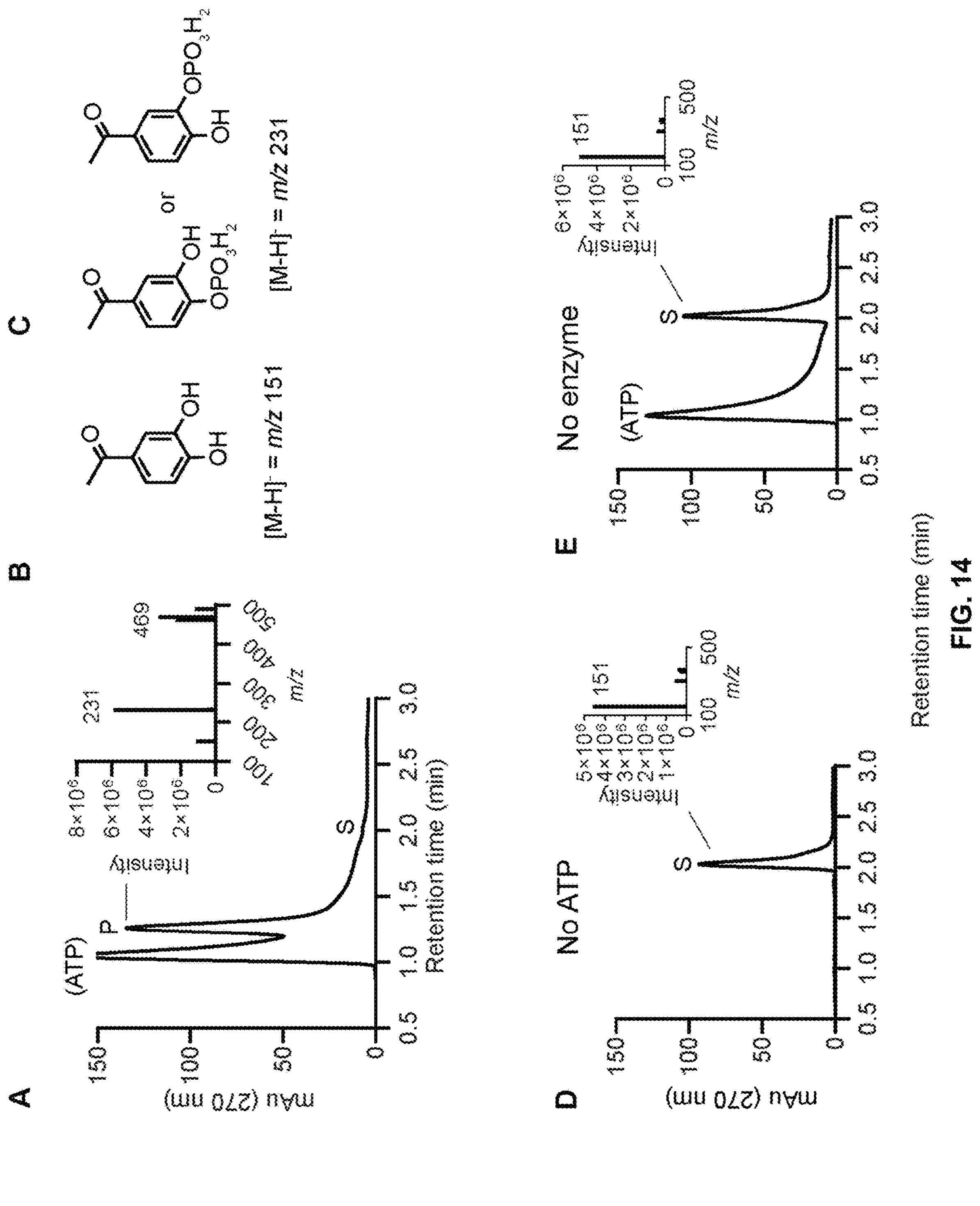
FIG. 14. The Saro_1862 E16K variant phosphorylates 3,4-dihydroxyacetophenone in an ATP-dependent manner. A, HPLC-MS analysis of an in vitro reaction mixture containing 200 µM 3,4-dihydroxyacetophenone, Saro_1862 E16K, and ATP following a 1 h incubation at 30° C. The inset shows a negative mode mass scan from 100 to 500 m/z of the peak identified by HPLC. The ATP peak in the injection spike is also labeled. P and S denote product and substrate, respectively, identified by retention time, absorbance, and mass scans. B, chemical structure and expected m/z of 3,4-dihydroxyacetophenone. C, possible chemical structures and expected m/z of phosphorylated 3,4-dihydroxyacetophenone. D, HPLC-MS analysis of the Saro_1862 E16K in vitro reaction mixture without ATP. E, HPLC-MS analysis of the Saro_1862 E16K in vitro reaction mixture without Saro_1862.
Figure 15:
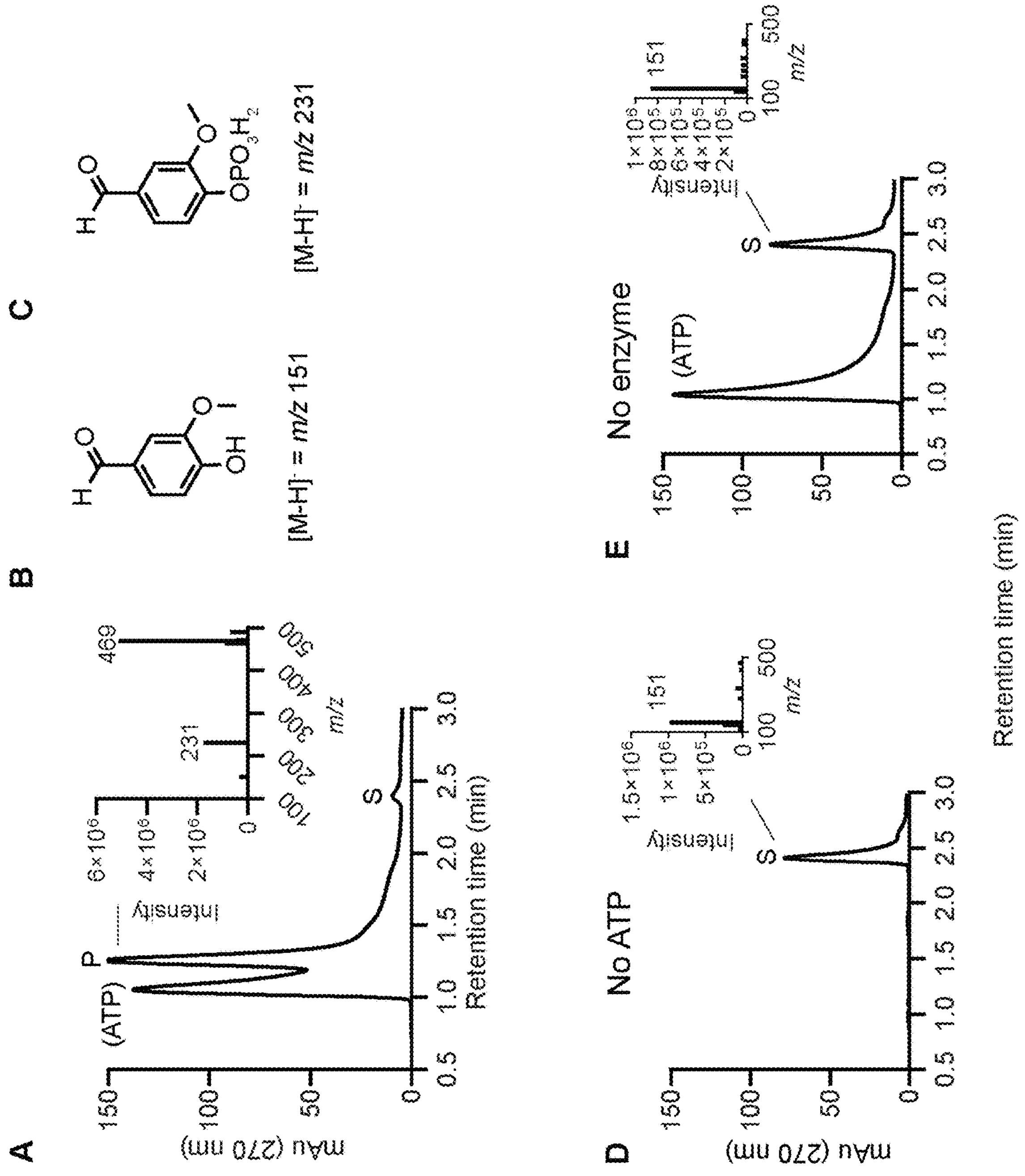
FIG. 15. The Saro_1862 E16K variant phosphorylates vanillin in an ATP-dependent manner. A, HPLC-MS analysis of an in vitro reaction mixture containing 200 µM vanillin, Saro_1862 E16K, and ATP following a 1 h incubation at 30° C. The inset shows a negative mode mass scan from 100 to 500 m/z of the peak identified by HPLC. The ATP peak in the injection spike is also labeled. P and S denote product and substrate, respectively, identified by retention time, absorbance, and mass scans. B, chemical structure and expected m/z of vanillin. C, chemical structure and expected m/z of phosphorylated vanillin. D, HPLC-MS analysis of the Saro_1862 E16K in vitro reaction mixture without ATP. E, HPLC-MS analysis of the Saro_1862 E16K in vitro reaction mixture without Saro_1862.
Figure 16:
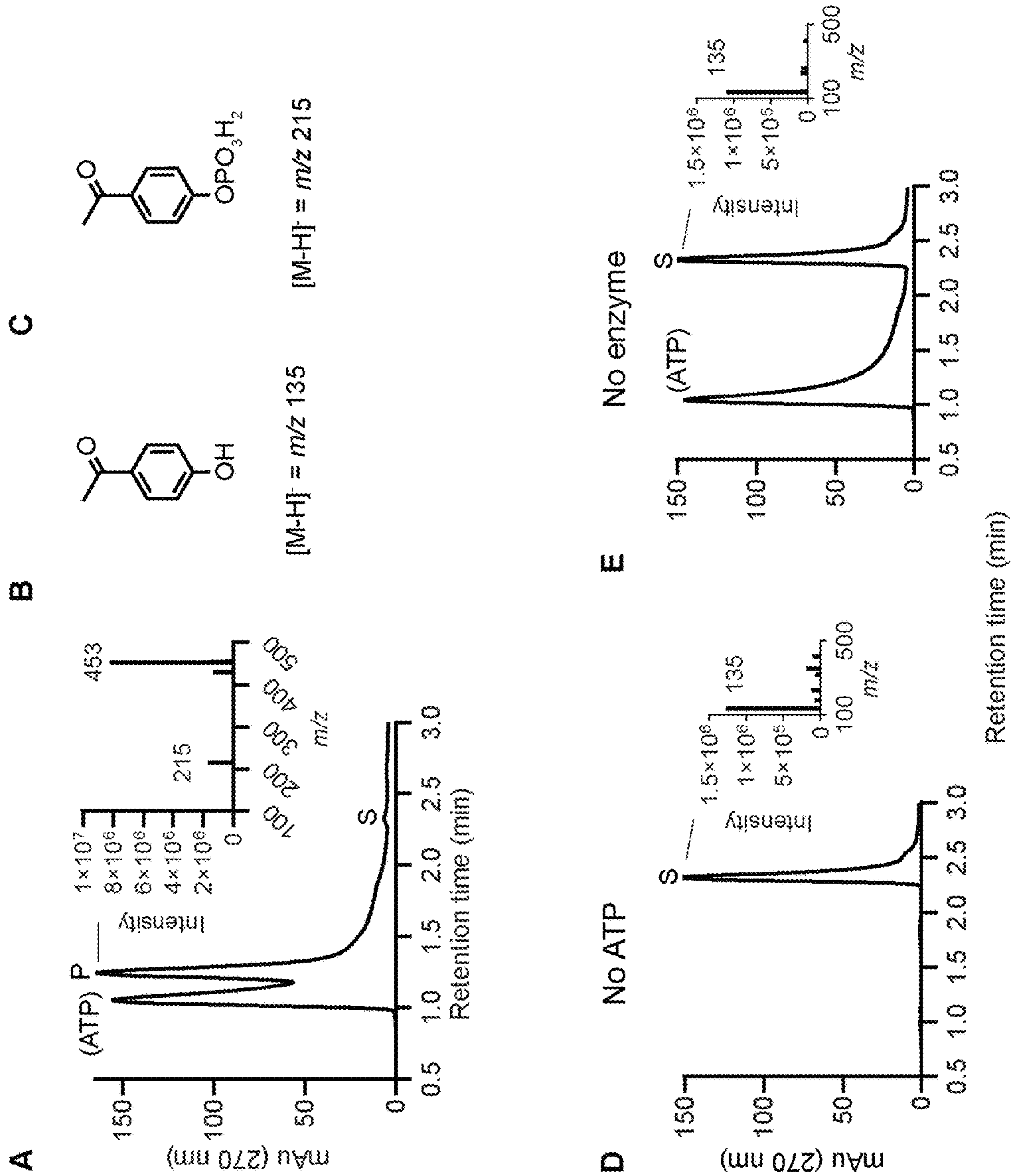
FIG. 16. The Saro_1862 E16K variant phosphorylates p-hydroxyacetophenone in an ATP-dependent manner. A, HPLC-MS analysis of an in vitro reaction mixture containing 200 µM p-hydroxyacetophenone, Saro_1862 E16K, and ATP following a 1 h incubation at 30° C. The inset shows a negative mode mass scan from 100 to 500 m/z of the peak identified by HPLC. The ATP peak in the injection spike is also labeled. P and S denote product and substrate, respectively, identified by retention time, absorbance, and mass scans. B, chemical structure and expected m/z of p-hydroxyacetophenone. C, chemical structure and expected m/z of phosphorylated p-hydroxyacetophenone. D, HPLC-MS analysis of the Saro_1862 E16K in vitro reaction mixture without ATP. E, HPLC-MS analysis of the Saro_1862 E16K in vitro reaction mixture without Saro_1862.
Figure 17:
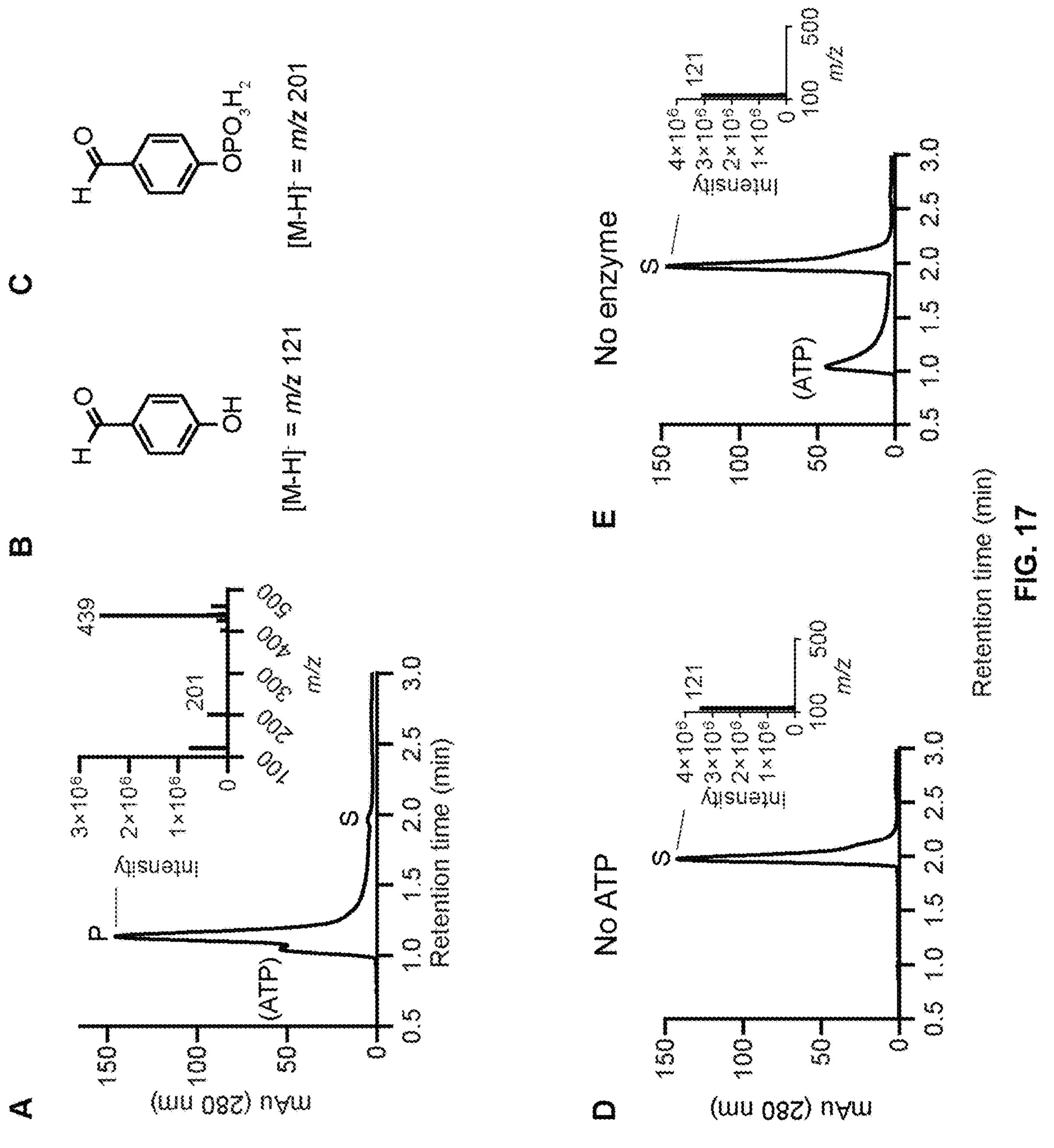
FIG. 17. The Saro_1862 E16K variant phosphorylates p-hydroxybenzaldehyde in an ATP-dependent manner. A, HPLC-MS analysis of an in vitro reaction mixture containing 200 µM p-hydroxybenzaldehyde, Saro_1862 E16K, and ATP following a 1 h incubation at 30° C. The inset shows a negative mode mass scan from 100 to 500 m/z of the peak identified by HPLC. The ATP peak in the injection spike is also labeled. P and S denote product and substrate, respectively, identified by retention time, absorbance, and mass scans. B, chemical structure and expected m/z of p-hydroxybenzaldehyde. C, chemical structure and expected m/z of phosphorylated p-hydroxybenzaldehyde. D, HPLC-MS analysis of the Saro_1862 E16K in vitro reaction mixture without ATP. E, HPLC-MS analysis of the Saro_1862 E16K in vitro reaction mixture without Saro_1862.
Figure 18:
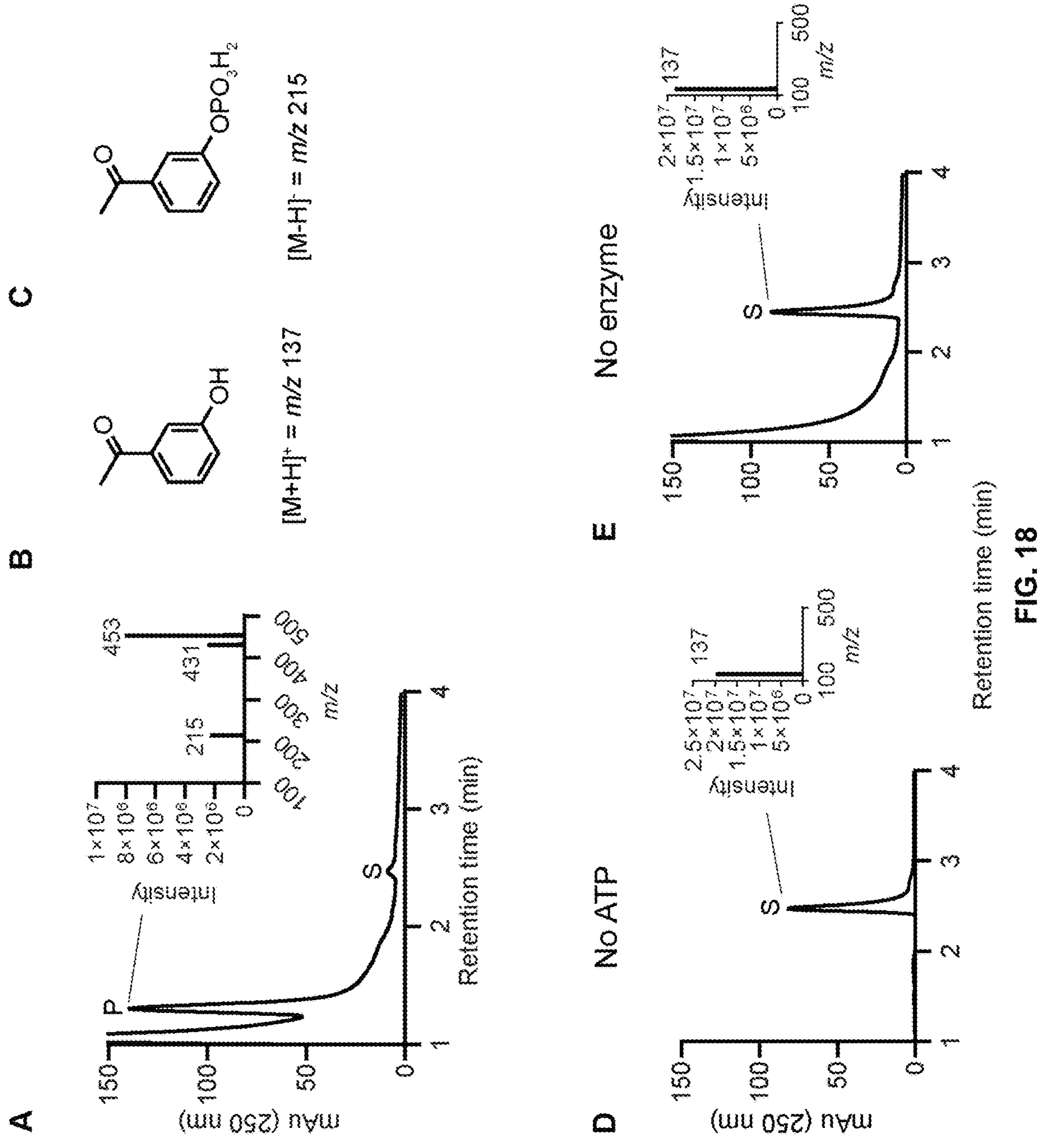
FIG. 18. The Saro_1862 E16K variant phosphorylates m-hydroxyacetophenone in an ATP-dependent manner. A, HPLC-MS analysis of an in vitro reaction mixture containing 200 µM m-hydroxyacetophenone, Saro_1862 E16K, and ATP following a 1 h incubation at 30° C. The inset shows a negative mode mass scan from 100 to 500 m/z of the peak identified by HPLC. P and S denote product and substrate, respectively, identified by retention time, absorbance, and mass scans. B, chemical structure and expected m/z of m-hydroxyacetophenone. C, chemical structure and expected m/z of phosphorylated m-hydroxyacetophenone. D, HPLC-MS analysis of the Saro_1862 E16K in vitro reaction mixture without ATP, with the inset showing a positive mode scan from 100 to 500 m/z because of poor ionization of m-hydroxyacetophenone in the negative mode. E, HPLC-MS analysis of the Saro_1862 E16K in vitro reaction mixture without Saro_1862, with the inset showing a positive mode scan.
Figure 19:
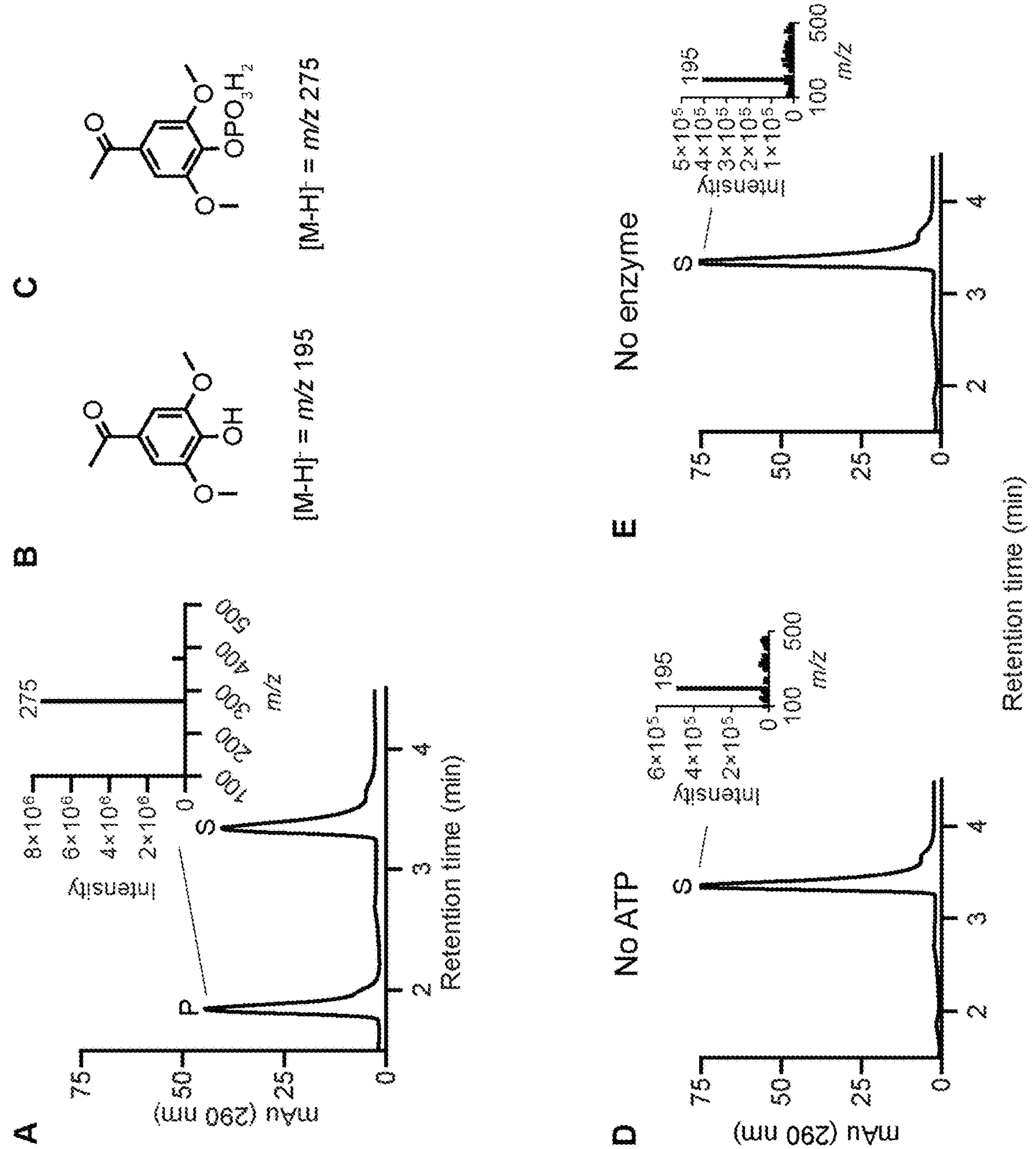
FIG. 19. The Saro_1862 E16K variant phosphorylates acetosyringone in an ATP-dependent manner. A, HPLC-MS analysis of an in vitro reaction mixture containing 200 µM acetosyringone, Saro_1862 E16K, and ATP following a 1 h incubation at 30° C. The inset shows a negative mode mass scan from 100 to 500 m/z of the peak identified by HPLC. P and S denote product and substrate, respectively, identified by retention time, absorbance, and mass scans. B, chemical structure and expected m/z of acetosyringone. C, chemical structure and expected m/z of phosphorylated acetosyringone. D, HPLC-MS analysis of the Saro_1862 E16K in vitro reaction mixture without ATP. E, HPLC-MS analysis of the Saro_1862 E16K in vitro reaction mixture without Saro_1862.
Figure 20:
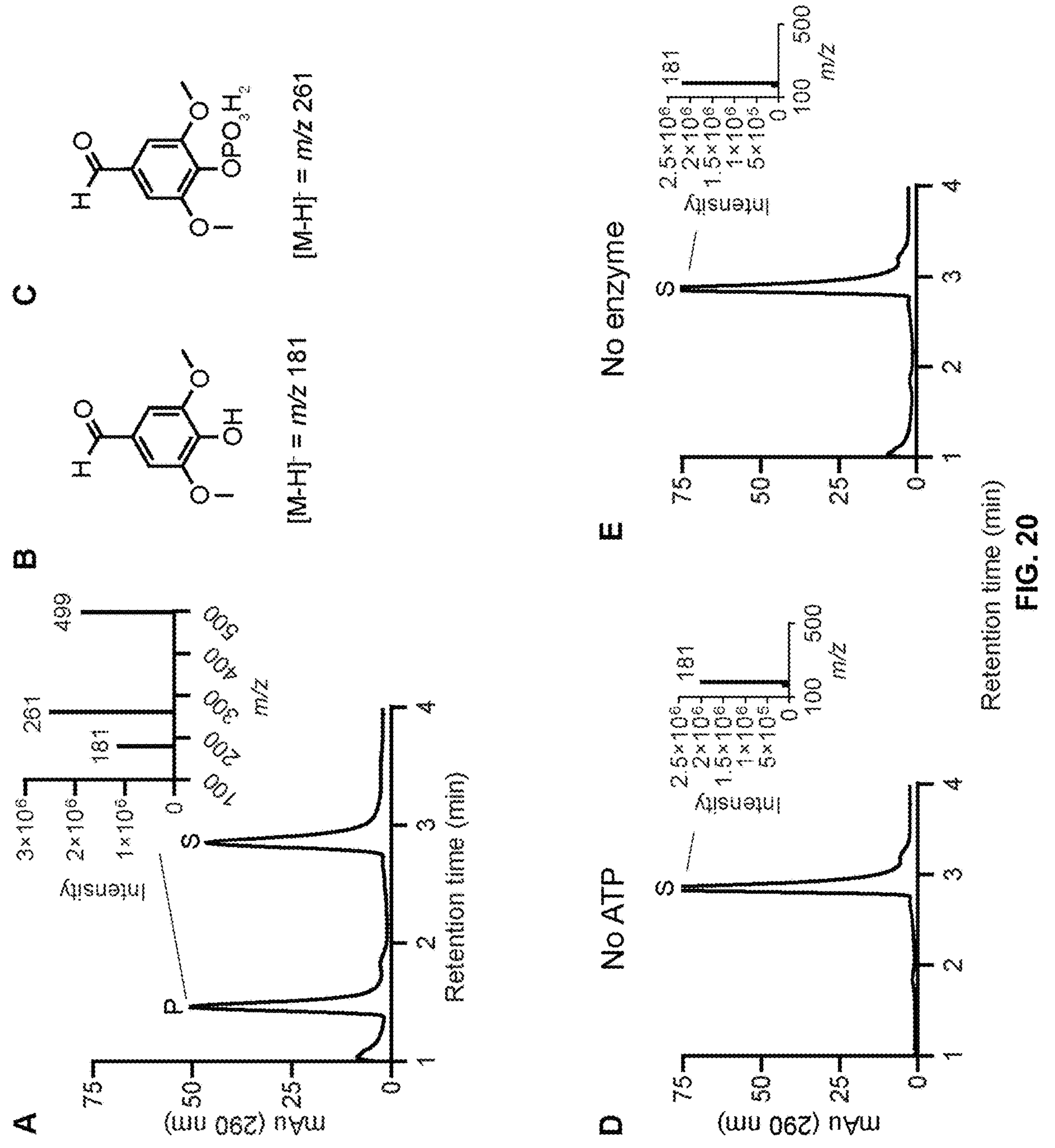
FIG. 20. The Saro_1862 E16K variant phosphorylates syringaldehyde in an ATP-dependent manner. A, HPLC-MS analysis of an in vitro reaction mixture containing 200 µM syringaldehyde, Saro_1862 E16K, and ATP following a 1 h incubation at 30° C. The inset shows a negative mode mass scan from 100 to 500 m/z of the peak identified by HPLC. P and S denote product and substrate, respectively, identified by retention time, absorbance, and mass scans. B, chemical structure and expected m/z of syringaldehyde. C, chemical structure and expected m/z of phosphorylated syringaldehyde. D, HPLC-MS analysis of the Saro_1862 E16K in vitro reaction mixture without ATP. E, HPLC-MS analysis of the Saro_1862 E16K in vitro reaction mixture without Saro_1862.
Figure 21:
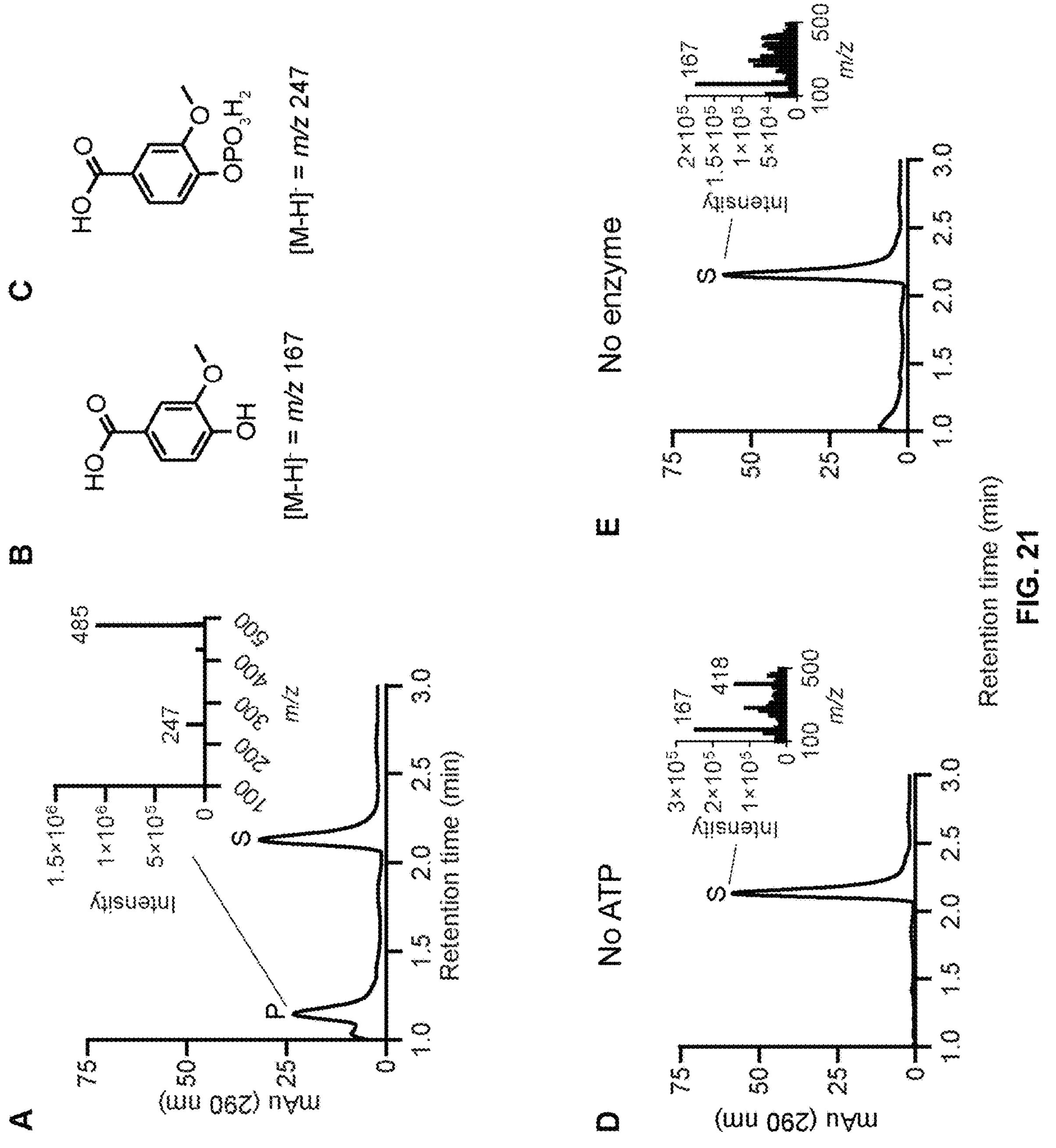
FIG. 21. The Saro_1862 E16K variant phosphorylates vanillic acid in an ATP-dependent manner. A, HPLC-MS analysis of an in vitro reaction mixture containing 200 μM vanillic acid, Saro_1862 E16K, and ATP following a 1 h incubation at 30° C. The inset shows a negative mode mass scan from 100 to 500 m/z of the peak identified by HPLC. P and S denote product and substrate, respectively, identified by retention time, absorbance, and mass scans. B, chemical structure and expected m/z of vanillic acid. C, chemical structure and expected m/z of phosphorylated vanillic acid. D, HPLC-MS analysis of the Saro_1862 E16K in vitro reaction mixture without ATP. E, HPLC-MS analysis of the Saro_1862 E16K in vitro reaction mixture without Saro_1862.
Figure 22:
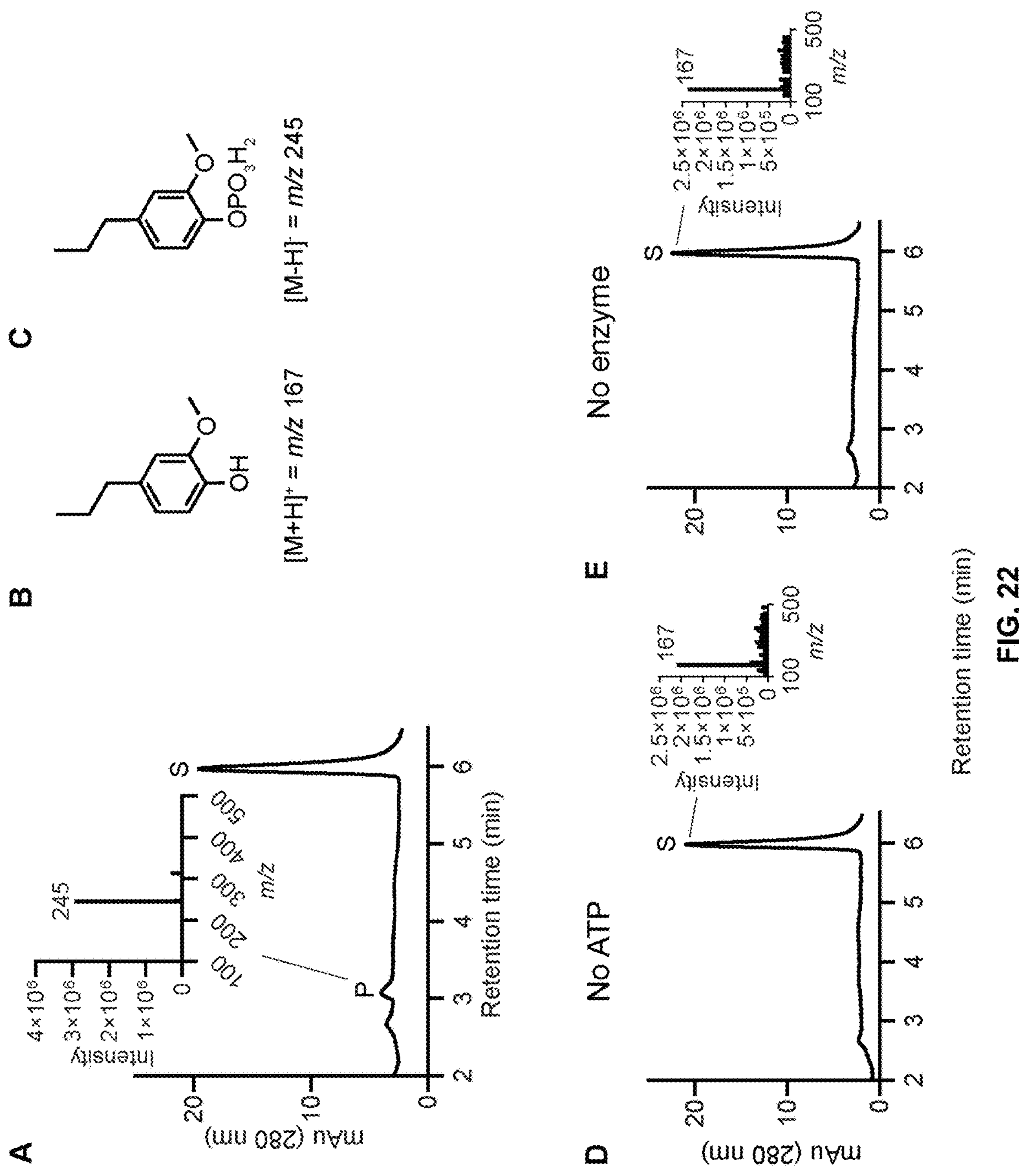
FIG. 22. The Saro_1862 E16K variant phosphorylates propylguaiacol in an ATP-dependent manner. A, HPLC-MS analysis of an in vitro reaction mixture containing 200 μM propylguaiacol, Saro_1862 E16K, and ATP following a 1 h incubation at 30° C. The inset shows a negative mode mass scan from 100 to 500 m/z of the peak identified by HPLC. P and S denote product and substrate, respectively, identified by retention time, absorbance, and mass scans. B, chemical structure and expected m/z of propylguaiacol. C, chemical structure and expected m/z of phosphorylated propylguaiacol. D, HPLC-MS analysis of the Saro_1862 E16K in vitro reaction mixture without ATP, with the inset showing a positive mode scan from 100 to 500 m/z because of poor ionization of propylguaiacol in the negative mode. E, HPLC-MS analysis of the Saro_1862 E16K in vitro reaction mixture without Saro_1862, with the inset showing a positive mode scan.
Figure 23:
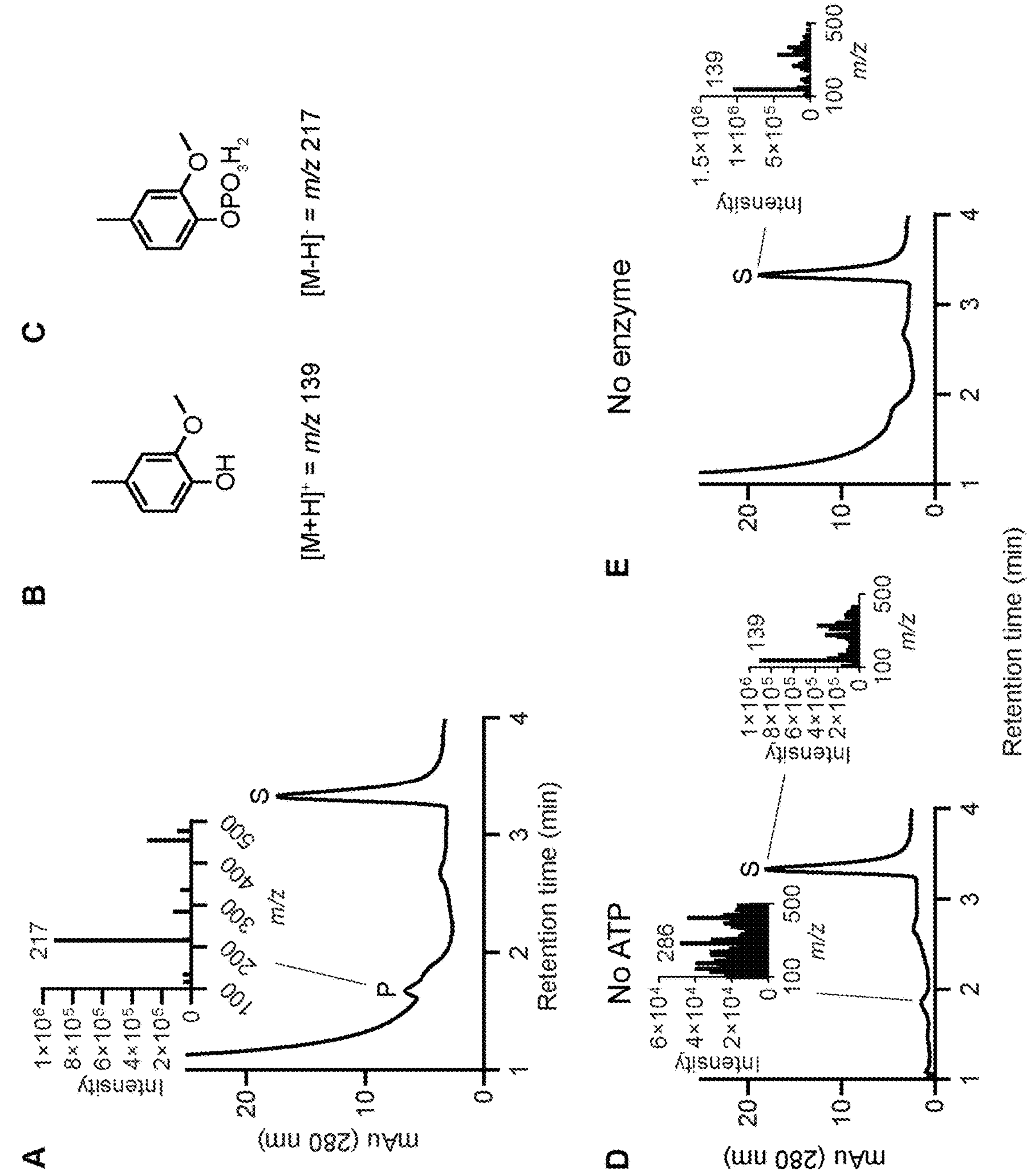
FIG. 23. The Saro_1862 E16K variant phosphorylates methylguaiacol in an ATP-dependent manner. A, HPLC-MS analysis of an in vitro reaction mixture containing 200 μM methylguaiacol, Saro_1862 E16K, and ATP following a 1 h incubation at 30° C. The inset shows a negative mode mass scan from 100 to 500 m/z of the peak identified by HPLC. P and S denote product and substrate, respectively, identified by retention time, absorbance, and mass scans. B, chemical structure and expected m/z of methylguaiacol. C, chemical structure and expected m/z of phosphorylated methylguaiacol. D, HPLC-MS analysis of the Saro_1862 E16K in vitro reaction mixture without ATP, with the insets showing both a negative mode scan of the peak before 2 min and a positive mode scan of the peak at 3.3 min because of poor ionization of methylguaiacol in the negative mode. E, HPLC-MS analysis of the Saro_1862 E16K in vitro reaction mixture without Saro_1862, with the inset showing a positive mode scan.
Figure 24:
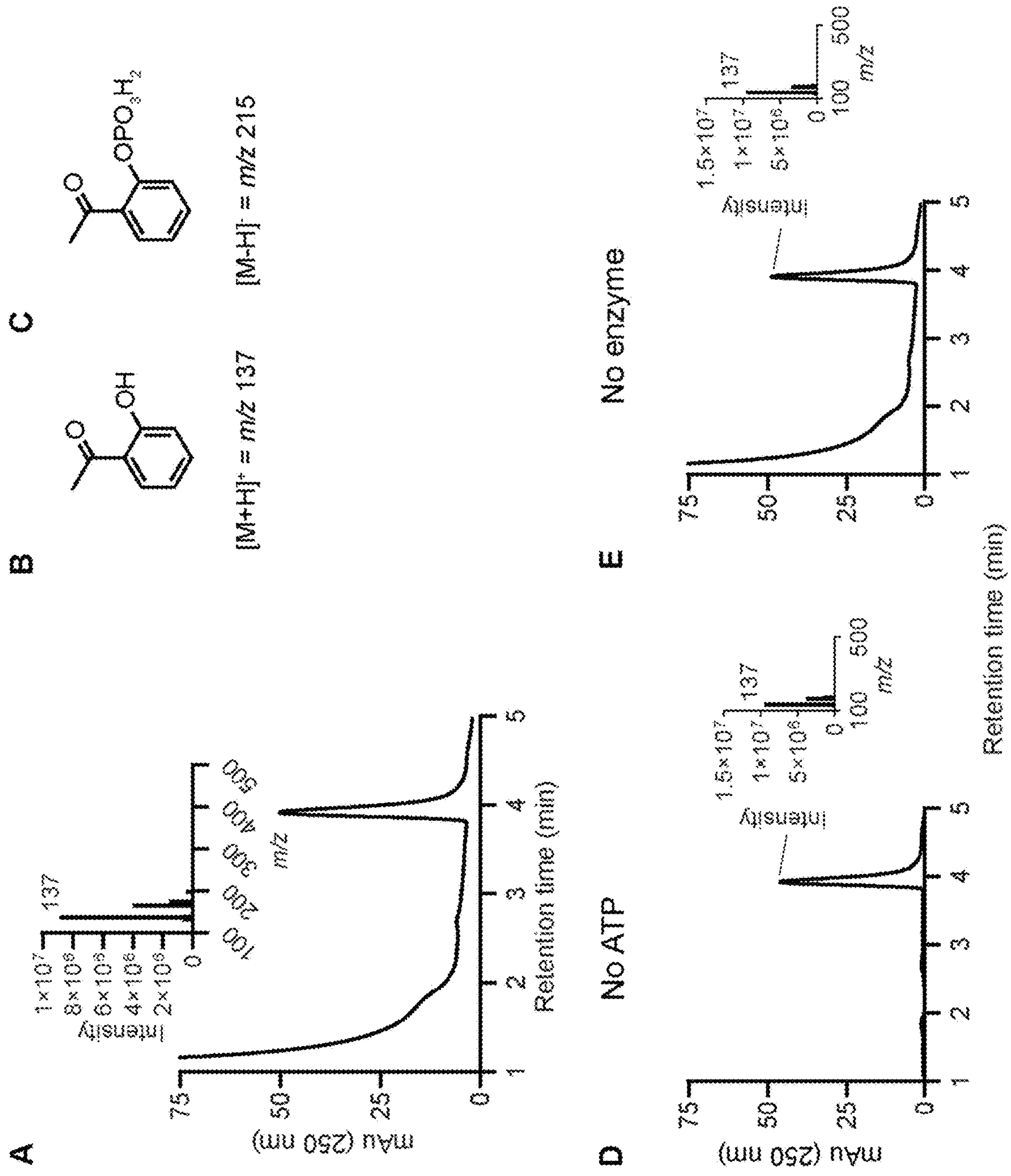
FIG. 24. The Saro_1862 E16K variant shows no detectable phosphorylation of o-hydroxyacetophenone. A, HPLC-MS analysis of an in vitro reaction mixture containing 200 μM o-hydroxyacetophenone, Saro_1862 E16K, and ATP following a 1 h incubation at 30° C. All insets show a positive mode mass scan from 100 to 500 m/z of the peak identified by HPLC. B, chemical structure and expected m/z of o-hydroxyacetophenone. C, chemical structure and expected m/z of phosphorylated o-hydroxyacetophenone. D, HPLC-MS analysis of the Saro_1862 E16K in vitro reaction mixture without ATP. E, HPLC-MS analysis of the Saro_1862 E16K in vitro reaction mixture without Saro_1862.
Figure 25:
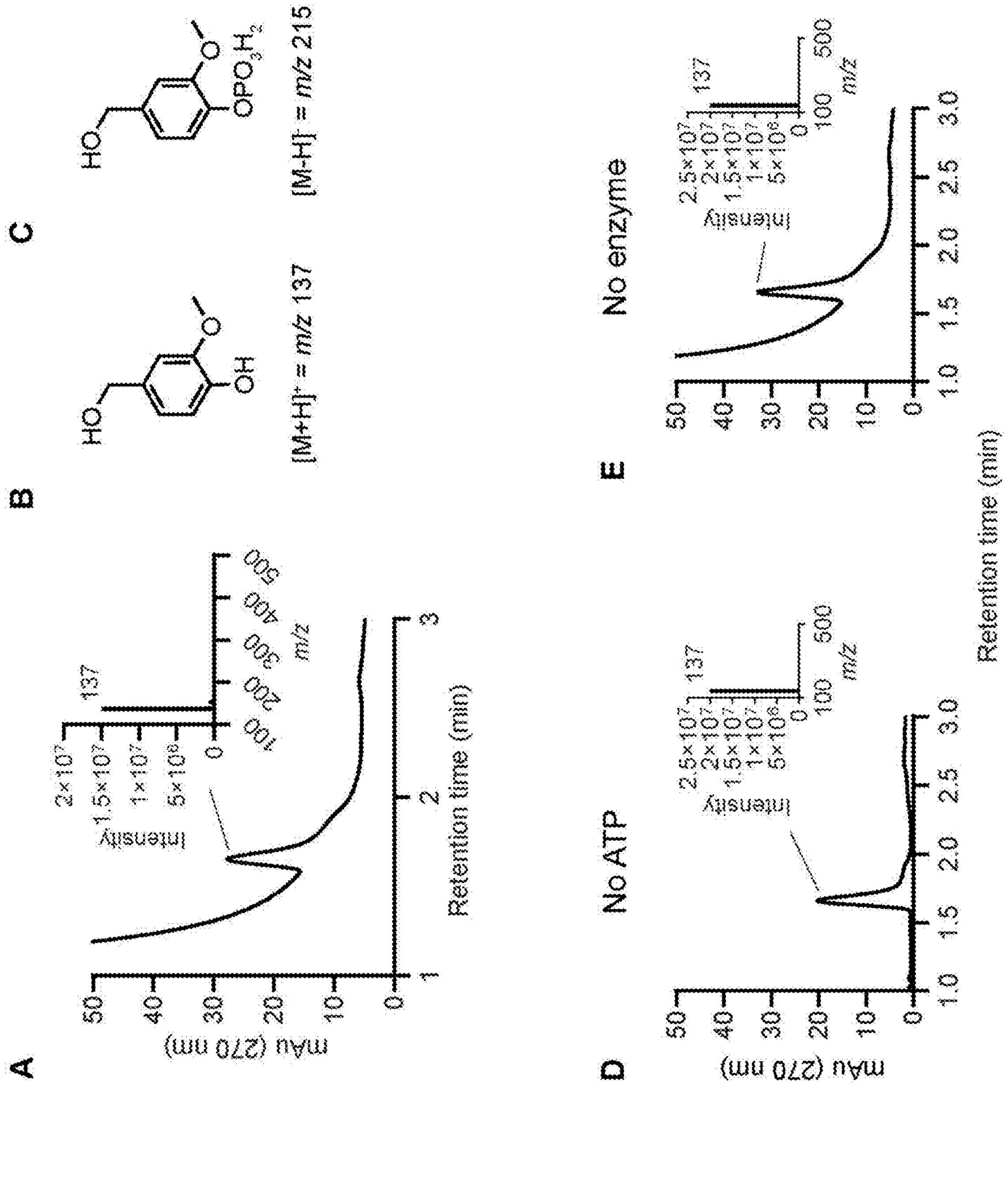
FIG. 25. The Saro_1862 E16K variant shows no detectable phosphorylation of vanillyl alcohol. A, HPLC-MS analysis of an in vitro reaction mixture containing 200 μM vanillyl alcohol, Saro_1862 E16K, and ATP following a 1 h incubation at 30° C. All insets show a positive mode mass scan from 100 to 500 m/z of the peak identified by HPLC. B, chemical structure and expected m/z of vanillyl alcohol. C, chemical structure and expected m/z of phosphorylated vanillyl alcohol. D, HPLC-MS analysis of the Saro_1862 E16K in vitro reaction mixture without ATP. E, HPLC-MS analysis of the Saro_1862 E16K in vitro reaction mixture without Saro_1862.
Figure 26:
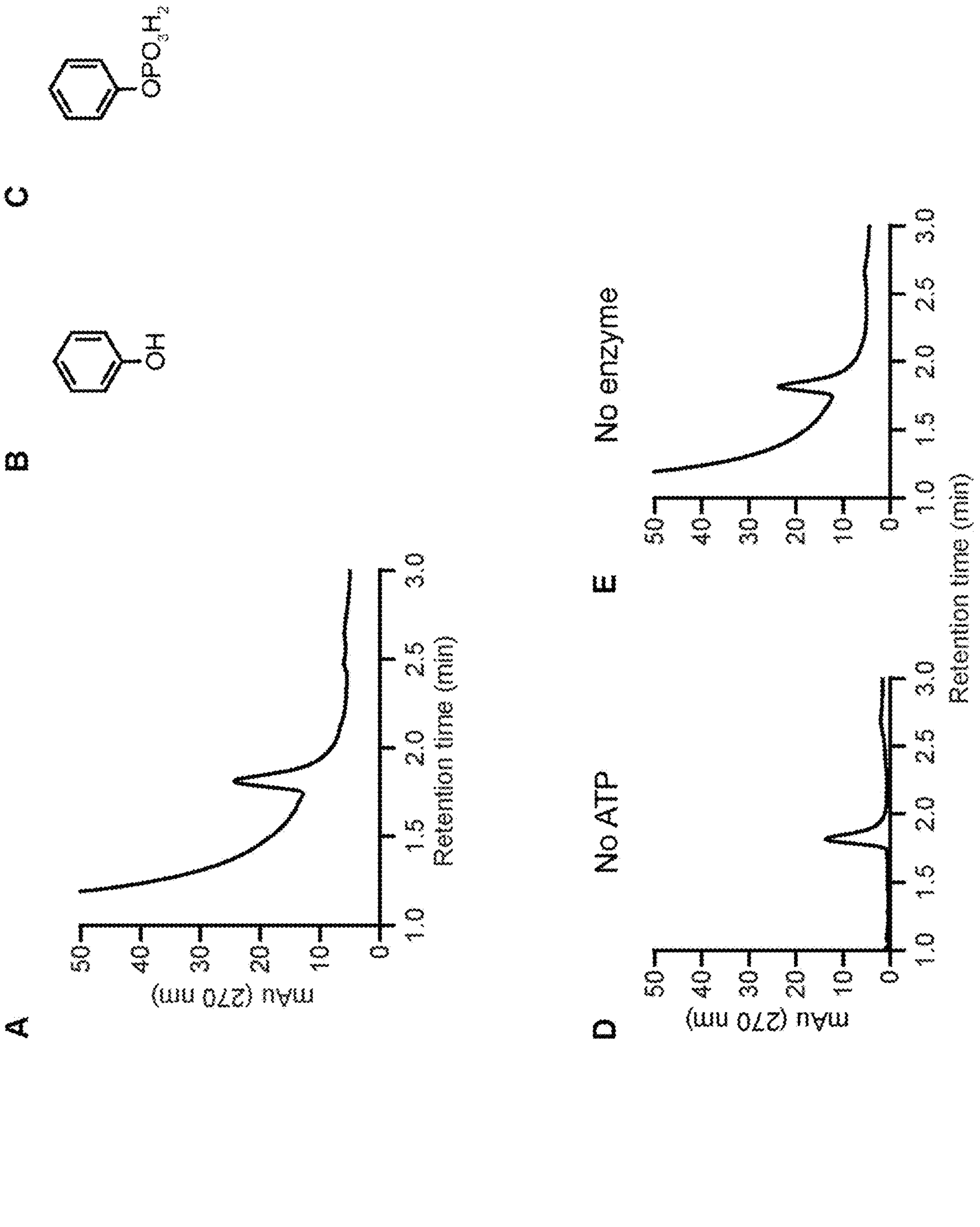
FIG. 26. The Saro_1862 E16K variant shows no detectable phosphorylation of phenol. A, HPLC analysis of an in vitro reaction mixture containing 200 μM phenol, Saro_1862 E16K, and ATP following a 1 h incubation at 30° C. No mass scans are shown as phenol (mass: 96) is too small to be detected by our 100 to 500 m/z scans. B, chemical structure of phenol. C, expected chemical structure of phosphorylated phenol. D, HPLC analysis of the Saro_1862 E16K in vitro reaction mixture without ATP. E, HPLC analysis of the Saro_1862 E16K in vitro reaction mixture without Saro_1862.
Figure 27:
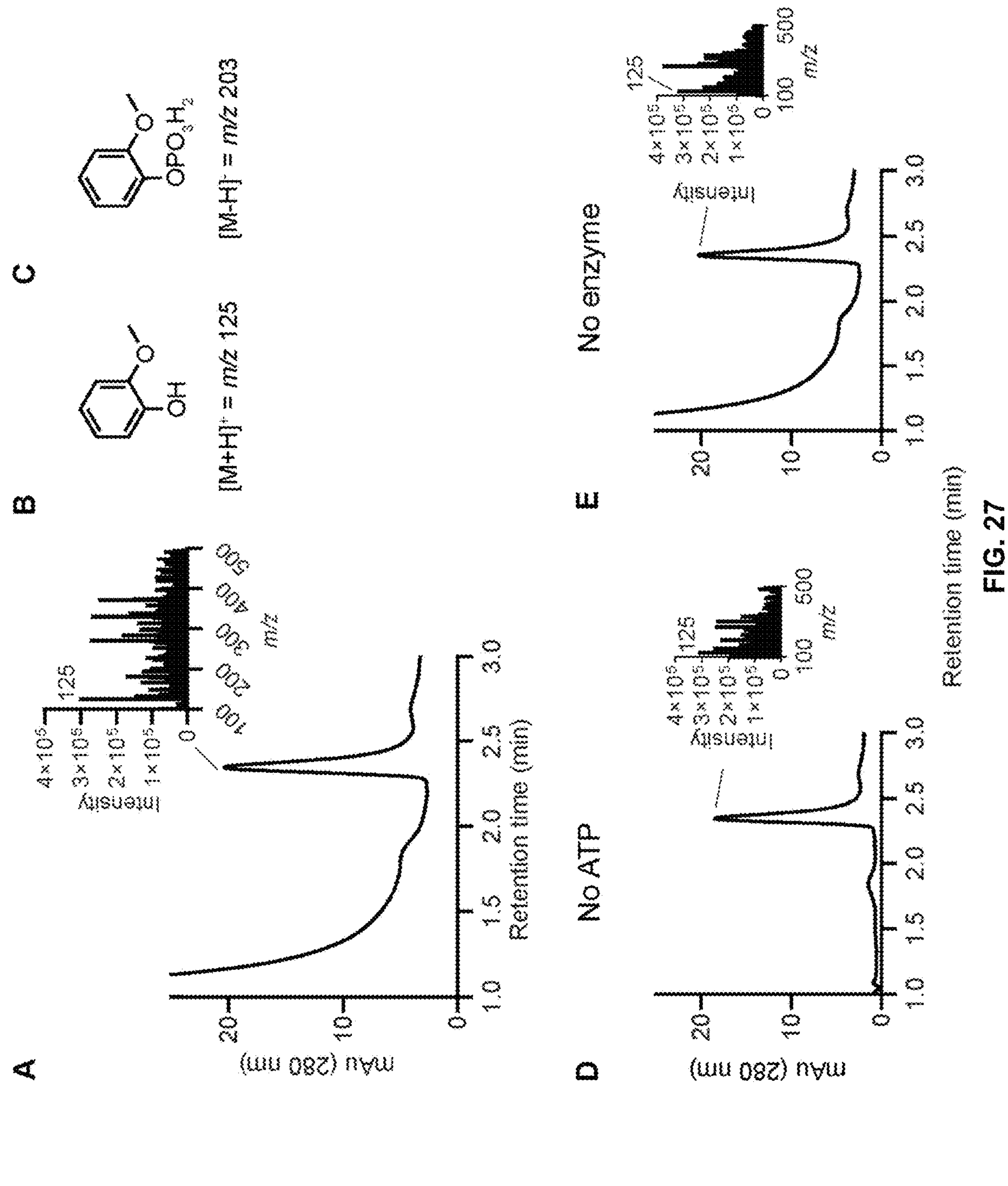
FIG. 27. The Saro_1862 E16K variant shows no detectable phosphorylation of guaiacol. A, HPLC-MS analysis of an in vitro reaction mixture containing 200 μM guaiacol, Saro_1862 E16K, and ATP following a 1 h incubation at 30° C. All insets show a positive mode mass scan from 100 to 500 m/z of the peak identified by HPLC. Guaiacol appeared to not ionize well since the MS signal was barely above background. B, chemical structure and expected m/z of guaiacol. C, chemical structure and expected m/z of phosphorylated guaiacol. D, HPLC-MS analysis of the Saro_1862 E16K in vitro reaction mixture without ATP. E, HPLC-MS analysis of the Saro_1862 E16K in vitro reaction mixture without Saro_1862.
Figure 28:
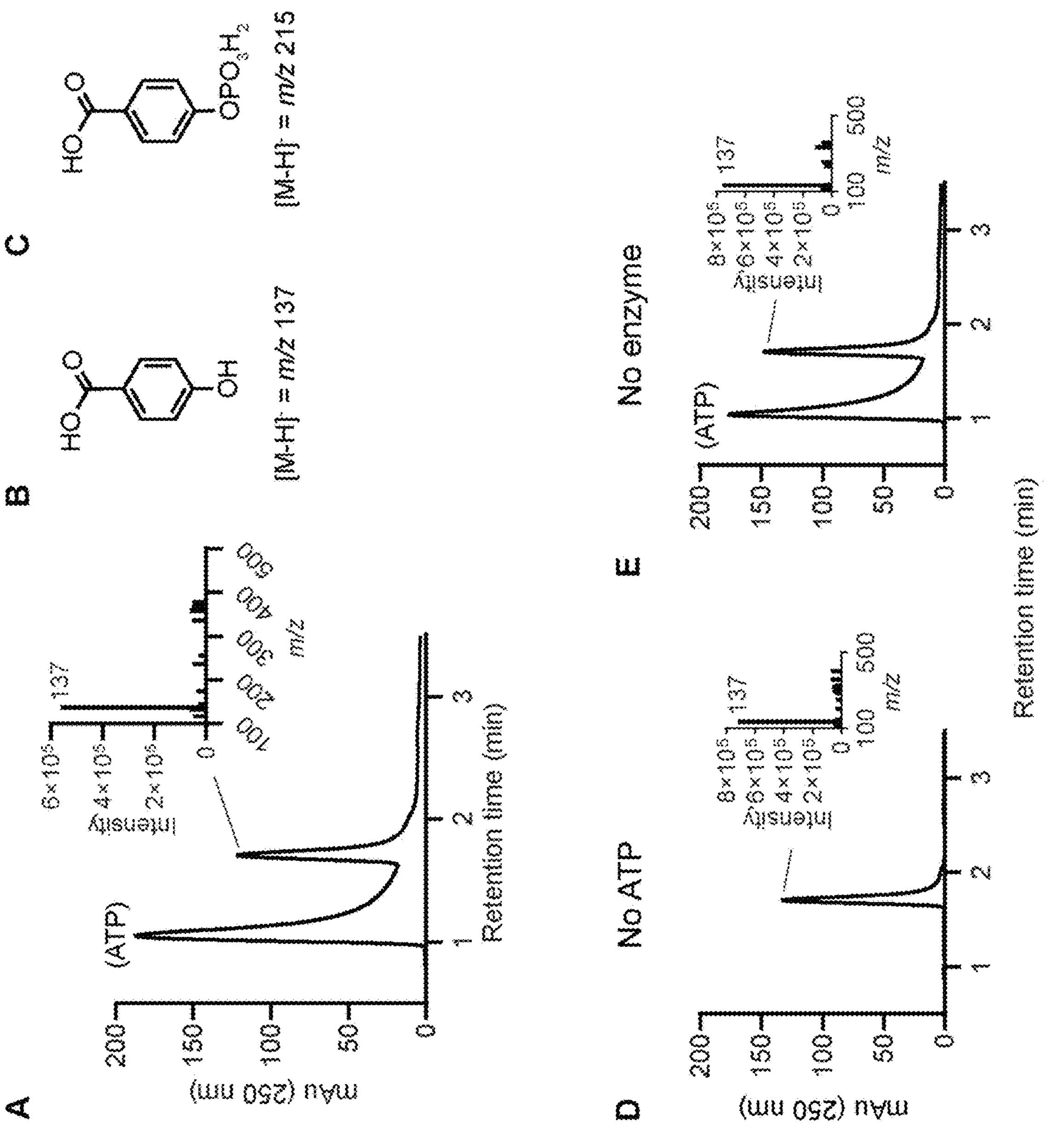
FIG. 28. The Saro_1862 E16K variant shows no detectable phosphorylation of p-hydroxybenzoic acid. A, HPLC-MS analysis of an in vitro reaction mixture containing 200 μM p-hydroxybenzoic acid, Saro_1862 E16K, and ATP following a 1 h incubation at 30° C. All insets show a negative mode mass scan from 100 to 500 m/z of the peak identified by HPLC. B, chemical structure and expected m/z of p-hydroxybenzoic acid. C, chemical structure and expected m/z of phosphorylated p-hydroxybenzoic acid. D, HPLC-MS analysis of the Saro_1862 E16K in vitro reaction mixture without ATP. E, HPLC-MS analysis of the Saro_1862 E16K in vitro reaction mixture without Saro_1862.
Figure 29:
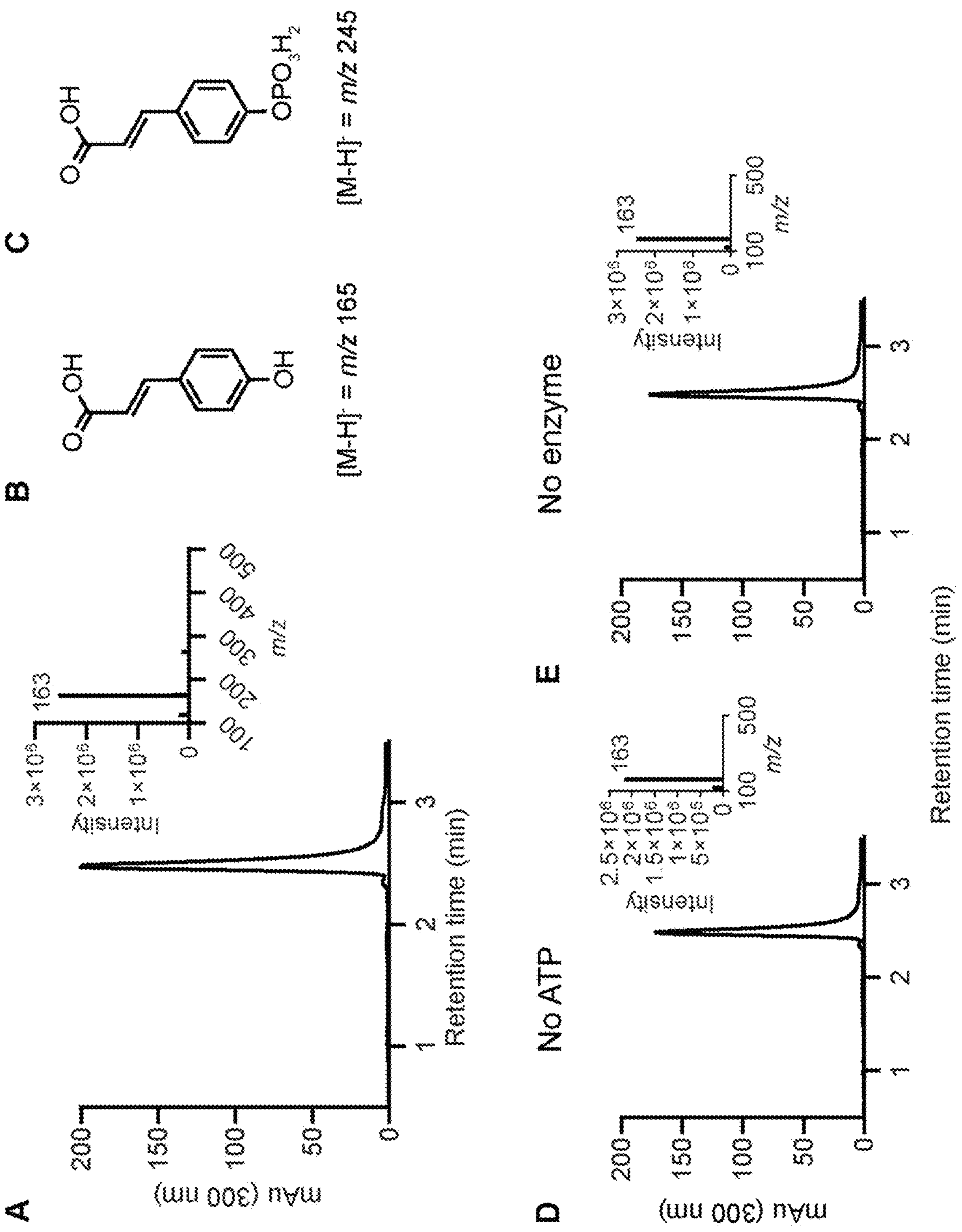
FIG. 29. The Saro_1862 E16K variant shows no detectable phosphorylation of p-coumaric acid. A, HPLC-MS analysis of an in vitro reaction mixture containing 200 μM p-coumaric acid, Saro_1862 E16K, and ATP following a 1 h incubation at 30° C. All insets show a negative mode mass scan from 100 to 500 m/z of the peak identified by HPLC. B, chemical structure and expected m/z of p-coumaric acid. C, chemical structure and expected m/z of phosphorylated p-coumaric acid. D, HPLC-MS analysis of the Saro_1862 E16K in vitro reaction mixture without ATP. E, HPLC-MS analysis of the Saro_1862 E16K in vitro reaction mixture without Saro_1862.
Figure 30:
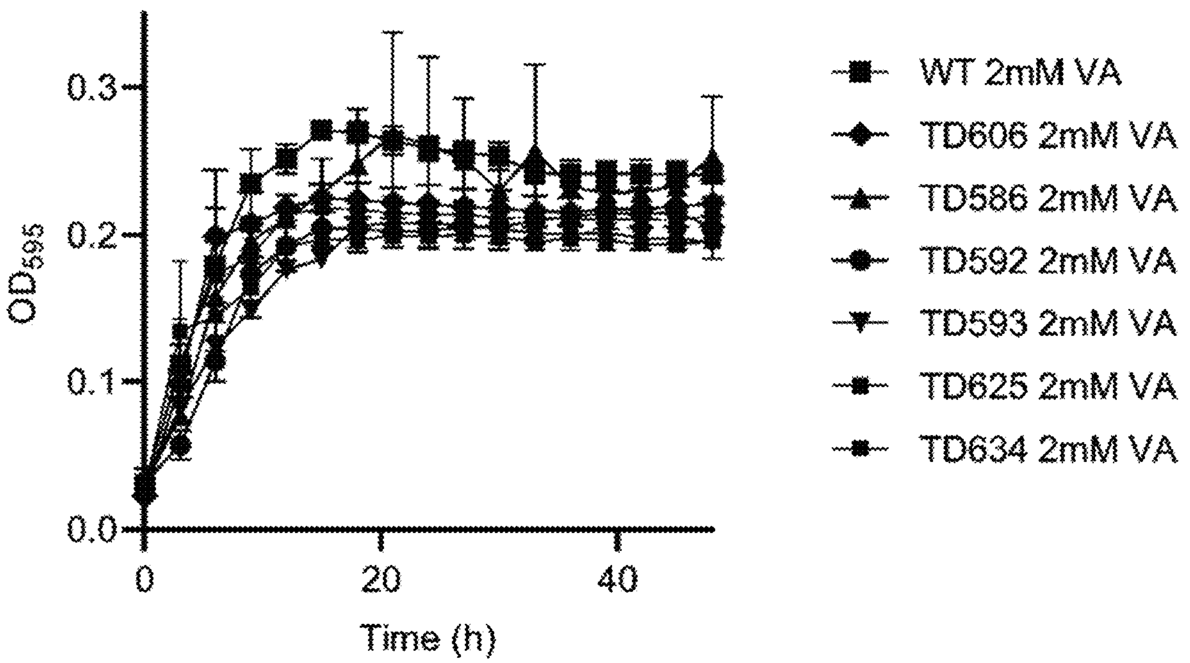
FIG. 30. Growth curves of *N. aromaticivorans* strains in SMB-vanillic acid (2 mM).
Figure 31:
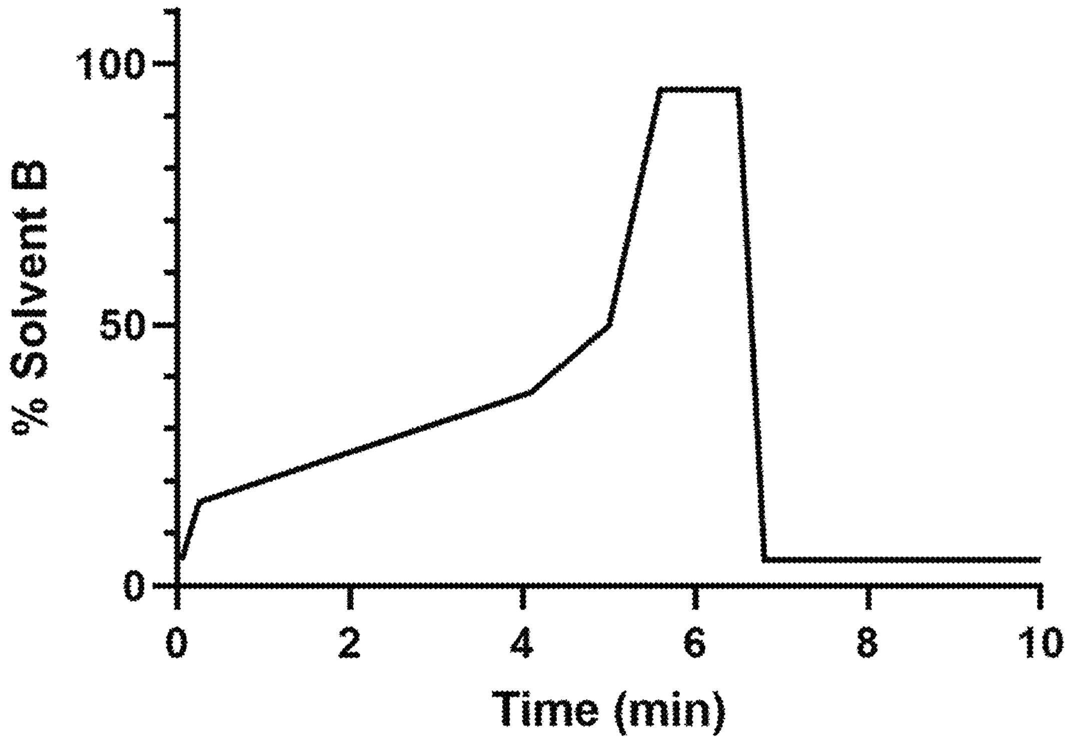
FIG. 31. Mobile phase binary gradient for HPLC-MS analysis of Saro_1862 in vitro reaction products. Solvent A is 0.2% formic acid in water and solvent B is methanol. The method ends at 10 min.

Media for the adaptive laboratory evolution experiment was made by mixing SMB-acetovanillone (1.7 mM) with SMB-vanillin (1.8 mM) in different ratios (schematically described in FIG. 2). Three replicate cultures were started in 20% SMB-acetovanillone/80% SMB-vanillin using parent *N. aromaticivorans* 1244441879 colonies from an SMB-glucose plate. After 72 h, 20 μL of each culture was used to inoculate a new 10 mL 20% SMB-acetovanillone/80% SMB-vanillin culture. These cultures were incubated for 48 h, followed by inoculating new cultures for 48 h, followed by inoculating new cultures for 72 h. Then, these 72 h cultures were used to inoculate 10 mL 50% SMB-acetovanillone/50% SMB-vanillin. We followed the same pattern of 48 h, 48 h, 72 h incubation of these cultures at this aromatic ratio. Next, these 72 h cultures were used to inoculate 10 mL 80% SMB-acetovanillone/20% SMB-vanillin, which again followed the same pattern of 48 h, 48 h, 72 h incubation at this aromatic ratio. Finally, these 72 h cultures were used to inoculate 100% SMB-acetovanillone cultures, which were incubated for 72 h before freezing aliquots from the three cultures, denoted TD561, TD562, and TD563. We plated these stocks on SMB-acetovanillone to isolate single colonies, which were designated strains TD585-596 (FIG. 2, Table 2). All cultures were monitored intermittently for cell density using a Klett-Summerson photoelectric colorimeter with a red filter, and they each showed increases in cell density before each passage (FIG. 12).

TABLE 2

All strains and plasmids used in this study.

| Name | Genotype | Description | Reference |
|---|---|---|---|
| *E. coli* strains | | | |
| NEB 5-alpha | fhuA2Δ(argF-lacZ)U169 phoA glnV44 Φ80Δ(lacZ)M15 gyrA96 recA1 relA1 endA1 thi-1 hsdR17 | Used for creating and maintaining plasmids | New England Biolabs, Inc. |
| S17-1 | recA pro hsdR RP4-2-Tc::Mu-Km::Tn7 | Used for mobilizing plasmids into *N. aromaticivorans* via conjugation | (43) |
| WM6026 | lacI$^q$, rrnB3, ΔlacZ4787, hsdR514, ΔaraBAD567, ΔrhaBAD568, rph-1, attλ::pAE12(ΔoriR6K-cat::Frt5), ΔendA::Frt, uidA(ΔMluI)::pir, attHK::pJK1006Δ(oriR6K-cat::Frt5; trfA::Frt) | Diaminopimelic acid auxotroph; used for mobilizing plasmids into *N. aromaticivorans* via conjugation | (44) |

TABLE 2-continued

All strains and plasmids used in this study.

| Name | Genotype | Description | Reference |
|---|---|---|---|
| B834(DE3) | $F^-$ ompT $hsdS_B(r_B^- m_B^-)$ gal dcm met (DE3) | BL21 parent; methionine auxotroph used for heterologous protein expression | (45) |
| TD604 | NEB 5-alpha pK18msB-Saro1862 E16K | NEB 5-alpha containing pK18msB-Saro1862 E16K | This work |
| TD613 | NEB 5-alpha pK18msB-delSaro1861 | NEB 5-alpha containing pK18msB-delSaro1861 | This work |
| TD618 | WM6026 pK18msB-delSaro1861 | WM6026 containing pK18msB-delSaro1861 for conjugation into *N. aromaticivorans* | This work |
| TD632 | NEB 5-alpha pK18msB-delSaro1858 | NEB 5-alpha containing pK18msB-delSaro1858 | This work |
| TD633 | WM6026 pK18msB-delSaro1858 | WM6026 containing pK18msB-delSaro1858 for conjugation into *N. aromaticivorans* | This work |
| TD617 | B834 pVP68K-Saro1862opt E16K | B834 carrying a plasmid for expressing an N-terminal $His_8$-tagged MBP fused with a codon-optimized version of Saro_1862 encoding the E16K substitution | This work |
| TD620 | NEB 5-alpha pVP68K-Saro1862opt E16 | NEB 5-alpha containing pVP68K-Saro1862opt E16 | This work |
| TD627 | B834 pVP68K-Saro1862opt E16 | B834 carrying a plasmid for expressing an N-terminal $His_8$-tagged MBP fused with a codon-optimized version of Saro_1862 | This work |
| *N. aromaticivorans* strains | | | |
| 12444Δ1879 | DSM 12444 ΔSaro_1879 | Parent strain; putative sacB has been deleted to allow genomic modifications using a sacB-containing plasmid | (33) |
| TD585 | DSM 12444 ΔSaro_1879, additional mutations | Isolate #1 from acetovanillone-evolved culture A | This work |
| TD586 | DSM 12444 ΔSaro_1879, additional mutations | Isolate #2 from acetovanillone-evolved culture A | This work |
| TD587 | DSM 12444 ΔSaro_1879, additional mutations | Isolate #3 from acetovanillone-evolved culture A | This work |
| TD588 | DSM 12444 ΔSaro_1879, additional mutations | Isolate #4 from acetovanillone-evolved culture A | This work |
| TD589 | DSM 12444 ΔSaro_1879, additional mutations | Isolate #1 from acetovanillone-evolved culture B | This work |
| TD590 | DSM 12444 ΔSaro_1879, additional mutations | Isolate #2 from acetovanillone-evolved culture B | This work |
| TD591 | DSM 12444 ΔSaro_1879, additional mutations | Isolate #3 from acetovanillone-evolved culture B | This work |
| TD592 | DSM 12444 ΔSaro_1879, additional mutations | Isolate #4 from acetovanillone-evolved culture B | This work |
| TD593 | DSM 12444 ΔSaro_1879, additional mutations | Isolate #1 from acetovanillone-evolved culture C | This work |
| TD594 | DSM 12444 ΔSaro_1879, additional mutations | Isolate #2 from acetovanillone-evolved culture C | This work |
| TD595 | DSM 12444 ΔSaro_1879, additional mutations | Isolate #3 from acetovanillone-evolved culture C | This work |
| TD596 | DSM 12444 ΔSaro_1879, additional mutations | Isolate #4 from acetovanillone-evolved culture C | This work |
| TD606 | DSM 12444 ΔSaro_1879, Saro_1862 46G > A | Parent with single nucleotide change encoding an E16K substitution in Saro_1862 | This work |

TABLE 2-continued

All strains and plasmids used in this study.

| Name | Genotype | Description | Reference |
|---|---|---|---|
| TD625 | DSM 12444 ΔSaro_1879, Saro_1862 46G > A, ΔSaro_1861 | TD606 with deleted Saro_1861 | This work |
| TD634 | DSM 12444 ΔSaro_1879, Saro_1862 46G > A, ΔSaro_1858 | TD606 with deleted Saro_1858 | This work |
| Plasmids | | | |
| pK18msB-MCS1 | | pK18mobsacB lacking the multiple cloning site, with a new XbaI site introduced | (33, 34) |
| pK18msB-Saro1862 E16K | | | This work |
| pK18msB-delSaro1861 | | pK18msB-MCS1 containing *N. aromaticivorans* genomic regions that flank Saro_1861 | This work |
| pK18msB-delSaro1858 | | pK18msB-MCS1 containing *N. aromaticivorans* genomic regions that flank Saro_1858 | This work |
| pVP68K | | pBR322 origin-containing plasmid for expressing $His_8$-tagged MBP fusion proteins from a T5 promoter. Encodes kanamycin resistance. | (36) |
| pVP68K-Saro1862opt E16K | | pVP68K plasmid containing a codon-optimized version of Saro_1862 with the E16K substitution. The plasmid also encodes an intervening TEV protease site (ENLYFQS) between MBP and Saro_1862 | This work |
| pVP68K-Saro1862opt E16 | | pVP68K plasmid containing a codon-optimized version of wild-type Saro_1862. The plasmid also encodes an intervening TEV protease site (ENLYFQS) between MBP and Saro_1862 | This work |

Whole Genome Sequencing

Evolved strains TD561-563 and TD585-596 were grown in 5 mL SMB-acetovanillone, and the parent strain *N. aromaticivorans* 1244441879 was grown in 5 mL SMB-glucose. Cell pellets were obtained by centrifuging 2.4 mL culture for 2 min at 15,000×g. Genomic DNA was isolated using a DNeasy Blood and Tissue Kit (Qiagen), quality checked using a Nanodrop ND1000, and quantified using the Qubit dsDNA BR assay. Genomic DNA (1000 ng) was sheared using a Covaris S220 Focused-ultrasonicator using the manufacturer's protocol for 300 bp target fragment size. DNA libraries were prepared using the NEBNext Ultra II DNA Library Prep Kit for Illumina. Prepared sequencing libraries were quantified using the Qubit dsDNA BR assay and fragment sizes were measured using a TapeStation D1000. Pooled libraries were sequenced using paired end 2×50 bp reads in an Illumina NextSeq 1000 following the manufacturer's protocol.

Sequence Data Analysis

Paired end Illumina sequencing reads were processed with Breseq (v0.36.1) (35) using default parameters. Reads were analyzed for genomic differences compared to the *N. aromaticivorans* DSM 12444 (Assembly Accession Number GCF_000013325.1). The mutations, primarily SNPs and INDELs, identified by Breseq in greater than 80% of sequencing reads were used for further analysis.

Generation of Defined *N. aromaticivorans* Mutants

*N. aromaticivorans* genomic mutations were created by homologous recombination using variants of the pK18mobsacB plasmid (34), with methods described in Supplementary Information. Briefly, plasmids containing regions of homology near the *N. aromaticivorans* genome modification site were transferred into *N. aromaticivorans* by conjugation using *E. coli* S17-1 or WM6026 cells. Transconjugants that had recombined the plasmid into the genome were selected for on plates containing kanamycin. Kanamycin-resistant colonies were streaked onto SMB+10 mM glucose+10% sucrose (w/v) to select for double cross-overs that result in the plasmid looping out of the genome. Colonies on sucrose-containing plates were patched onto kanamycin and sucrose plates separately to screen for kanamycin sensitivity and sucrose resistance. Such colonies were then screened by colony PCR to check for deletion of the desired gene, which was confirmed by Sanger sequencing.

Bacterial Growth Curves

Starter cultures of *N. aromaticivorans* strains were grown overnight in SMB-vanillate (4 mM). The following morning, these starter cultures were diluted 1:1 in fresh SMB-vanillate (4 mM) and shaken at 30° C. for an additional hour. Then, these cultures were used to inoculate 1.5 mL of SMB media containing a particular aromatic in a 24-well plate at a starting $OD_{600}$ of 0.05, as measured in a 1 cm cuvette. Various SMB media containing different aromatics were prepared fresh by adding a 1:100 dilution of 100× aromatic dissolved in methanol to the SMB media. The plates were grown at 30° C., shaking for 1 min every 15 min. Each condition was tested in biological triplicate.

Saro_1862 Expression and Purification

A gBlock of Saro_1862 was codon optimized for *E. coli* (Integrated DNA Technologies, Coralville, IA) and cloned into pVP68K (36), which adds an N-terminal Hiss-tagged maltose binding protein (MBP) to the protein coding sequence. Primers were designed to introduce a TEV protease cleavage site (ENLYFQS) directly upstream of the gene encoding Saro_1862. This plasmid was then transformed into in *E. coli* B834 cells. Protein expression was induced by growth in autoinduction medium ZMS-80155 (37) supplemented with 50 μg/mL kanamycin. The ZMS-80155 medium contains 1% N-Z Amine AS, 50 mM phosphate, 20 mM succinate, 0.8% glycerol, 0.015% glucose, 0.5% α-lactose, 2 mM $MgSO_4$, a trace metals mix (37), and a vitamin mix (38). Cultures were grown at room temperature for 24 h ($OD_{600}$>10), at which point they were chilled on ice. Cells were pelleted by centrifugation at 6000×g for 10 min at 4° C. The cell pellets were then resuspended in 20 mM HEPES pH 7.5 and 300 mM NaCl. Cell suspensions were sonicated using a Branson Sonifier 450 for 30 min at 25% duty cycle on the max power setting for the microtip attachment. Cell debris was separated from the cell lysate by centrifugation at 20,000×g for 30 min at 4° C.

The cell lysate was run through a Cytiva ÄKTA Pure™ 25 chromatography system with a Cytiva HisTrap™ HP 5 mL column kept at 4° C. for protein purification. The column was pre-equilibrated with 20 mM HEPES pH 7.5, 300 mM NaCl, and 20 mM imidazole, which was also used as the wash buffer following sample injection. Proteins were eluted with a 5 column volume (CV) gradient from 0% to 100% elution buffer, which contained 20 mM HEPES pH 7.5, 300 mM NaCl, and 300 mM imidazole. Elution buffer was held at 100% for 10 CVs until returning to 0%. Eluted protein was concentrated and buffer exchanged using a Amicon® Ultra-15 centrifugal filter unit with 20 mM HEPES pH 7.5, 300 mM NaCl. Protein was treated with approximately 0.015 mg/mL TEV protease for 24 h at room temperature. Next, cleaved protein was again run through the Cytiva ÄKTA Pure™ 25 chromatography system with a Cytiva HisTrap™ HP 5 mL column for separation of cleaved Saro_1862 from the Hiss-MBP. Using the same method, cleaved Saro_1862 eluted at ~40% elution buffer while Hiss-MBP eluted at ~90% elution buffer, as confirmed by enzyme activity assays and SDS-PAGE. Cleaved Saro_1862 was concentrated and buffer exchanged using a Amicon® Ultra-15 centrifugal filter unit with 20 mM HEPES pH 7.5, 300 mM NaCl. Protein concentration was determined using the Bio-Rad Protein Assay, using bovine serum albumin as a standard. Protein purity was assessed by SDS-PAGE.

In Vitro Aromatic Phosphorylation Assays

To test the ability of Saro_1862 protein to phosphorylate acetovanillone or other substrates, purified recombinant enzyme was mixed with substrate and ATP in a reaction buffer. A typical 100 μL reaction contained 20 mM HEPES pH 7.5, 2 mM $MgCl_2$, 200 μM $MnCl_2$, 1 mM ATP, 200 μM aromatic substrate (from a 2 mM stock in water), and 0.01 mg/ml Saro_1862 protein. The reaction was incubated at 30° C. for 1 h before analysis by high pressure liquid chromatography-mass spectrometry (HPLC-MS). Reaction products were separated by reverse-phase HPLC using a Phenomenex Kinetex F5 column (2.6 μm pore size, 2.1 mm ID, 150 mm length) attached to a Shimadzu Nexera XR HPLC system. The mobile phase was a binary gradient of solvent A (0.2% formic acid in water) and solvent B (methanol) flowing at 0.4 mL/min. To detect reaction products, absorbance was measured between 190 and 500 nm using a Shimadzu SPD-M20A photodiode array detector. The eluent from the HPLC was also analyzed via mass spectrometry using a Shimadzu triple quadrupole mass spectrometer LCMS-8045. We used negative mode Q3 scans from 100 m/z to 500 m/z around the retention times of HPLC peaks to obtain mass spectra of compounds eluting at such times.

Measurement of the Rate of Acetovanillone Phosphorylation by Saro_1862

Figure 5:
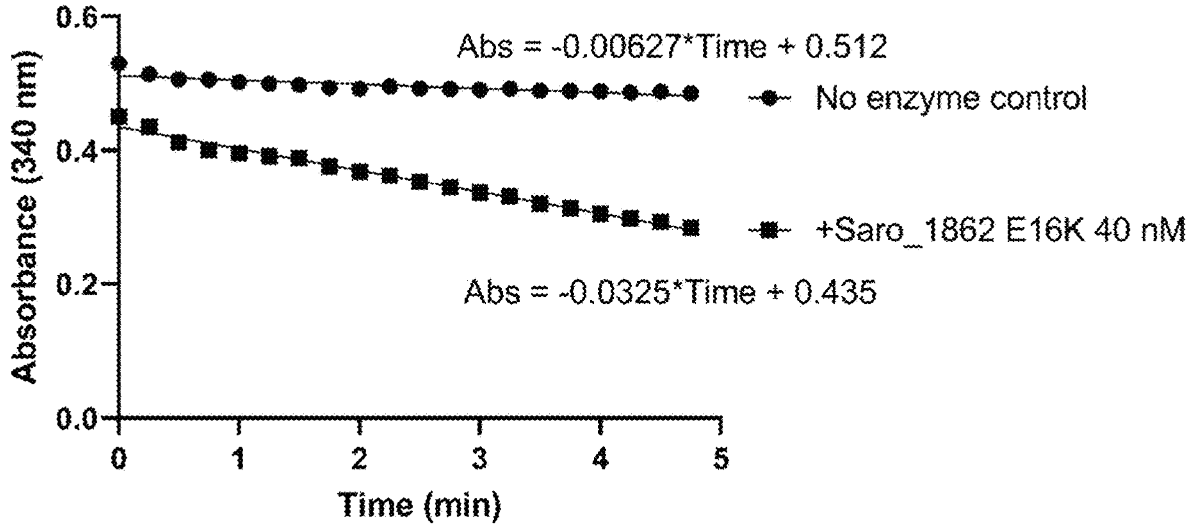
FIG. 5. Representative technical replicate measurement for rate of acetovanillone phosphorylation by recombinant Saro_1862 E16K, monitored by loss of absorbance at 340 nm as described in Materials and Methods. The reaction rate was calculated by taking the difference in slope between the samples containing and lacking enzyme, converting to rate of substrate loss using the difference in extinction coefficients between acetovanillone and phospho-acetovanillone from (21) ($\varepsilon$=12.11 $mM^{-1}$ $cm^{-1}$) and a measured path length of 0.62 cm, and dividing by enzyme concentration (40 nM) to yield a rate with units $min^{-1}$.

The rates of acetovanillone phosphorylation by the Saro_1862 E16K variant enzyme and the Saro_1862 wild type enzyme were measured as described in (21), with two modifications: the reaction buffer used 20 mM Tris pH 8 instead of 20 mM HEPPS pH 8, and the enzyme concentration was approximately 40 nM (Saro_1862 E16K) or 40 μM (Saro_1862 wild type) instead of 1 μM to help ensure measurements were obtained under initial velocity conditions. Otherwise, the buffer similarly contained 50 μM acetovanillone, 2 mM MgCl2, 1 mM MnCl2, 2 mM DTT, and 1 mM ATP. The reaction was monitored by absorbance at 340 nm, and a blank-adjusted reaction rate was calculated based on the difference in extinction coefficients for acetovanillone and phospho-acetovanillone at 340 nm (21) and a measured path length of 0.62 cm based on a 200 μL reaction in a 96-well plate (FIG. 5). The assay was performed in technical triplicates. The rate reported for Saro_1862 E16K represents the average of three separate preparations of Saro_1862 E16K protein.

Size Exclusion Chromatography

Size exclusion chromatography was used to determine the oligomerization state of native Saro_1862 E16K. A Phenomenex bioZen size exclusion column (SEC-2 1.8 μm 150 Å 150×4.6 mm) hooked up to a Shimadzu Nexera XR HPLC system set to 0.7 μL injections and a 0.3 mL/min flow rate was used for sample separation. The mobile phase was 20 mM HEPES, pH 7.5, containing 300 mM NaCl. Protein retention times were determined by absorbance at 280 nm as measured by a Shimadzu SPD-M20A photodiode array detector. A standard curve was created by plotting $\log_{10}$ molecular weight versus retention time for standards in the Supelco Protein Standard Mix 15-600 kDa and for bovine serum albumin. The molecular weight of Saro_1862 E16K was determined from the linear fit of this standard curve.

Searching for Genes Encoding Acetovanillone Kinase and Other Acetovanillone Metabolism Proteins in Bacteria The conversion of acetovanillone to vanillic acid requires an acetovanillone kinase (Saro_1862 or AcvAB/HpeHI), a carboxylase (AcvCDE/HpeCBA), a phosphatase (AcvF/HpeD), a CoA ligase (VceA or HpeE), and a beta-ketoacyl-CoA hydrolase (VceB or HpeF) (20,21). Thus, we searched NCBI for genomes that contained homologs of Saro_1862 (ABD26302.1), AcvA (WP_014074980.1) or HpcH (UZF45677.1), AcvB (WP_014074979.1) or HpeI (UZF45676.1), AcvC (WP_014074978.1) or HpeC (UZF45675.1), AcvD (WP_014074977.1) or HpeB (UZF45674.1), AcvE (WP_014074976.1) or HpcA (UZF45673.1), AcvF (WP_014074975.1) or HpcD (UZF45672.1), VccA (BAK67171.1) or HpcE (UZF45671.1), and VceB (BAK65920.1) or HpeF (UZF45670.1). We used tBLASTn in BLAST+ version 2.14.1 (39) against the ref_prok_rep_genomes database downloaded from NCBI on Sep. 12, 2023. We used the default tBLASTn parameters, and kept all hits that met the E-value cutoff of 0.01. Next, we used the taxonomy ID of each BLAST hit with TaxonKit software (40) to obtain lineage information for each species. The tBLASTn hits for all proteins, including genomic locations of the hits, can be performed by conduct the tBLASTn search outlined above. Finally, we compared the list of tBLASTn hits for each protein to assemble two separate lists of species with acetovanillone metabolism gene homologs: first, those that encode homologs of Saro_1862, AcvC or HpeC, AcvD or HpeB, AcvE or HpeA, AcvF or HpeD, VceA or HpeE, and VceB or HpeF (Table 3); second, those that encode homologs of AcvA or HpeH, AcvB or HpeI, AcvC or HpeC, AcvD or HpcB, AcvE or HpeA, AcvF or HpeD, VceA or HpeE, and VceB or HpeF (Table 4).

To display the findings in a tree representing the diversity of bacteria, we started with the phylogenetic tree of all classes of bacteria in the GTDB available in AnnoTree (41). We pruned all unnamed nodes, collapsed some classes into phyla, and pruned any classes that were not present in the NCBI representative prokaryotic genomes database to yield a tree that best matched the subgroups contained in the NCBI representative prokaryotic genomes database. Finally, we used lineage information obtained for each species that contained BLAST hits to label the distribution of our hits in the bacterial phylogenetic tree. Tree manipulations were performed using Tree Viewer (42).

Construction of Plasmids for Generating in-Frame Deletions of Saro_1858 or Saro_1861

Regions of *Novosphingobium aromaticivorans* genomic DNA containing ~1000 bp upstream and downstream of the genes to be deleted were amplified via PCR. Plasmid pK18msB-MCS1 (a variant of pK18mobsacB (Schäfer et al.[34]) in which the multiple cloning site has been removed, and which contains a gene for kanamycin resistance and sacB for sucrose sensitivity) was linearized via PCR as previously described (Kontur et al.[33]). The upstream and downstream flanking regions for each gene were combined with linearized pK18msB-MCS1 using the NEBuilder HiFi Assembly system (New England Biolabs, Ipswich, MA) to produce a plasmid in which the upstream and downstream DNA sequences are adjacent, with no intervening coding region (Table 1). In the case of Saro_1858, the first codon was retained because these nucleotides contained the stop codon of Saro_1859. In the case of Saro_1861, the plasmid was designed to eliminate the entire gene from the start to the stop codon. The plasmids were transformed into NEB 5-alpha competent *Escherichia coli* cells (New England Biolabs). The transformed *E. coli* cells were cultured in LB media+kanamycin, the plasmids were purified using a Qiagen® Plasmid Maxi Kit (Qiagen, Germany), and DNA sequencing was used to confirm the presence of the desired junction between upstream and downstream fragments.

Construction of Plasmid for Generating the Saro_1862 E16K Mutant in *N. aromaticivorans*

Upstream and downstream flanking regions of ~1000 bp overlapped at the E16 codon and primers were designed to encode the E16K mutation (from GAG to AAG). These regions were amplified via PCR and cloned into pK18msB-MCS1 as described above.

REFERENCES

1. Strassberger, Z., Tanase, S., and Rothenberg, G. (2014) The pros and cons of lignin valorisation in an integrated biorefinery. *RSC Advances* 4, 25310-25318
2. Zakzeski, J., Bruijnincx, P. C. A., Jongerius, A. L., and Weckhuysen, B. M. (2010) The Catalytic Valorization of Lignin for the Production of Renewable Chemicals. *Chemical Reviews* 110, 3552-3599
3. Schutyser, W., Renders, T., Van den Bosch, S., Koelewijn, S. F., Beckham, G. T., and Sels, B. F. (2018) Chemicals from lignin: an interplay of lignocellulose fractionation, depolymerisation, and upgrading. *Chemical Society Reviews* 47, 852-908
4. Sun, Z., Fridrich, B., de Santi, A., Elangovan, S., and Barta, K. (2018) Bright Side of Lignin Depolymerization: Toward New Platform Chemicals. *Chemical Reviews* 118, 614-678
5. Bidlack, J. E., and Dashek, W. V. (2017) Plant cell walls. in *Plant Cells and their Organelles* (Dashek, W. V., and Miglani, G. S. eds.), Wiley-Blackwell. pp 209-238
6. Grotewold, E., Jones Prather, K. L., and Peters, K. (2015) Lignocellulosic Biomass for Advanced Biofuels and Bioproducts: Workshop Report, Washington, DC, Jun. 23-24, 2014.
7. Xu, C., Arancon, R. A. D., Labidi, J., and Luque, R. (2014) Lignin depolymerisation strategies: towards valuable chemicals and fuels. *Chemical Society Reviews* 43, 7485-7500
8. Zhu, Y., Liao, Y., Lv, W., Liu, J., Song, X., Chen, L., Wang, C., Sels, B. F., and Ma, L. (2020) Complementing Vanillin and Cellulose Production by Oxidation of Lignocellulose with Stirring Control. *ACS Sustainable Chemistry & Engineering* 8, 2361-2374
9. Abdelaziz, O. Y., Ravi, K., Mittermeier, F., Meier, S., Riisager, A., Lidén, G., and Hulteberg, C. P. (2019) Oxidative Depolymerization of Kraft Lignin for Microbial Conversion. *ACS Sustainable Chemistry & Engineering* 7, 11640-11652
10. Villar, J. C., Caperos, A., and García-Ochoa, F. (2001) Oxidation of hardwood kraft-lignin to phenolic derivatives with oxygen as oxidant. *Wood Science and Technology* 35, 245-255
11. Navas, L. E., Dexter, G., Liu, J., Levy-Booth, D., Cho, M., Jang, S. K., Mansfield, S. D., Renneckar, S., Mohn, W. W., and Eltis, L. D. (2021) Bacterial Transformation of Aromatic Monomers in Softwood Black Liquor. *Frontiers in microbiology* 12, 735000
12. Abdelaziz, O. Y., Li, K., Tunå, P., and Hulteberg, C. P. (2018) Continuous catalytic depolymerisation and conversion of industrial kraft lignin into low-molecular-weight aromatics. *Biomass Conversion and Biorefinery* 8, 455-470
13. Almqvist, H., Veras, H., Li, K., Garcia Hidalgo, J., Hulteberg, C., Gorwa-Grauslund, M., Skorupa Parachin, N., and Carlquist, M. (2021) Muconic Acid Production Using Engineered *Pseudomonas putida* KT2440 and a Guaiacol-Rich Fraction Derived from Kraft Lignin. *ACS Sustainable Chemistry & Engineering* 9, 8097-8106
14. Perez, J. M., Sener, C., Misra, S., Umana, G. E., Coplien, J., Haak, D., Li, Y., Maravelias, C. T., Karlen, S. D., Ralph, J., Donohue, T. J., and Noguera, D. R. (2022) Integrating lignin depolymerization with microbial funneling processes using agronomically relevant feedstocks. *Green Chemistry* 24, 2795-2811
15. Perez Jose, M., Kontur Wayne, S., Gehl, C., Gille Derek, M., Ma, Y., Niles Alyssa, V., Umana, G., Donohue Timothy, J., and Noguera Daniel, R. (2021) Redundancy in Aromatic O-Demethylation and Ring-Opening Reactions in *Novosphingobium aromaticivorans* and Their Impact in the Metabolism of Plant-Derived Phenolics. *Applied and Environmental Microbiology* 87, c02794-02720
16. Vilbert, A. C., Kontur, W. S., Gille, D., Noguera, D. R., and Donohue, T. J. (2023) Engineering *Novosphingobium aromaticivorans* to produce cis, cis-muconic acid from biomass aromatics. *Applied and Environmental Microbiology* (in revision)
17. Hall, B. W., Kontur, W. S., Neri, J. C., Gille, D. M., Noguera, D. R., and Donohue, T. J. (2023) Production of carotenoids from aromatics and pretreated lignocellulosic biomass by *Novosphingobium aromaticivorans*. *Applied and Environmental Microbiology* (in press)
18. Perez, J. M., Kontur, W. S., Alherech, M., Coplien, J., Karlen, S. D., Stahl, S. S., Donohue, T. J., and Noguera, D. R. (2019) Funneling aromatic products of chemically depolymerized lignin into 2-pyrone-4-6-dicarboxylic acid with *Novosphingobium aromaticivorans. Green Chemistry* 21, 1340-1350

19. Linz, A. M., Ma, Y., Perez, J. M., Myers, K. S., Kontur, W. S., Noguera, D. R., and Donohue, T. J. (2021) Aromatic Dimer Dehydrogenases from *Novosphingobium aromaticivorans* Reduce Monoaromatic Diketones. *Applied and Environmental Microbiology* 87, c01742-01721
20. Higuchi, Y., Kamimura, N., Takenami, H., Kikuiri, Y., Yasuta, C., Tanatani, K., Shobuda, T., Otsuka, Y., Nakamura, M., Sonoki, T., and Masai, E. (2022) The Catabolic System of Acetovanillone and Acetosyringone in *Sphingobium* sp. Strain SYK-6 Useful for Upgrading Aromatic Compounds Obtained through Chemical Lignin Depolymerization. *Applied and Environmental Microbiology* 88, c00724-00722
21. Dexter, G. N., Navas, L. E., Grigg, J. C., Bajwa, H., Levy-Booth, D. J., Liu, J., Louie, N. A., Nasseri, S. A., Jang, S. K., Renneckar, S., Eltis, L. D., and Mohn, W. W. (2022) Bacterial catabolism of acetovanillone, a lignin-derived compound. *Proceedings of the National Academy of Sciences of the United States of America* 119, e2213450119
22. Newman, D. L., Coakley, A., Link, A., Mills, K., and Wright, L. K. (2021) Punnett Squares or Protein Production? The Expert-Novice Divide for Conceptions of Genes and Gene Expression. *CBE life sciences education* 20, ar53
23. Ishibashi, K., Kezuka, Y., Kobayashi, C., Kato, M., Inoue, T., Nonaka, T., Ishikawa, M., Matsumura, H., and Katoh, E. (2014) Structural basis for the recognition-evasion arms race between Tomato mosaic virus and the resistance gene Tm−1. *Proceedings of the National Academy of Sciences* 111, E3486-E3495
24. Jumper, J., Evans, R., Pritzel, A., Green, T., Figurnov, M., Ronneberger, O., Tunyasuvunakool, K., Bates, R., Žídek, A., Potapenko, A., Bridgland, A., Meyer, C., Kohl, S. A. A., Ballard, A. J., Cowie, A., Romera-Paredes, B., Nikolov, S., Jain, R., Adler, J., Back, T., Petersen, S., Reiman, D., Clancy, E., Zielinski, M., Steinegger, M., Pacholska, M., Berghammer, T., Bodenstein, S., Silver, D., Vinyals, O., Senior, A. W., Kavukcuoglu, K., Kohli, P., and Hassabis, D. (2021) Highly accurate protein structure prediction with AlphaFold. *Nature* 596, 583-589
25. Holm, L., Laiho, A., Törönen, P., and Salgado, M. (2023) DALI shines a light on remote homologs: One hundred discoveries. *Protein Science* 32, e4519
26. Kamps, M. P., and Sefton, B. M. (1986) Neither arginine nor histidine can carry out the function of lysine-295 in the ATP-binding site of p60src. *Molecular and cellular biology*
27. Carrera, A. C., Alexandrov, K., and Roberts, T. M. (1993) The conserved lysine of the catalytic domain of protein kinases is actively involved in the phosphotransfer reaction and not required for anchoring ATP. *Proceedings of the National Academy of Sciences* 90, 442-446
28. Potter, D., Wojnar, J. M., Narasimhan, C., and Miziorko, H. M. (1997) Identification and Functional Characterization of an Active-site Lysine in Mevalonate Kinase. *Journal of Biological Chemistry* 272, 5741-5746
29. Fry, D. C., Kuby, S. A., and Mildvan, A. S. (1986) ATP-binding site of adenylate kinase: mechanistic implications of its homology with ras-encoded p21, F1-ATPase, and other nucleotide-binding proteins. *Proceedings of the National Academy of Sciences* 83, 907-911
30. Kamimura, N., Takahashi, K., Mori, K., Araki, T., Fujita, M., Higuchi, Y., and Masai, E. (2017) Bacterial catabolism of lignin-derived aromatics: New findings in a recent decade: Update on bacterial lignin catabolism. *Environmental Microbiology Reports* 9, 679-705
31. García-Hidalgo, J., Ravi, K., Kurć, L.-L., Lidén, G., and Gorwa-Grauslund, M. (2019) Identification of the two-component guaiacol demethylase system from *Rhodococcus rhodochrous* and expression in *Pseudomonas putida* EM42 for guaiacol assimilation. *AMB Express* 9, 34
32. Mallinson, S. J. B., Machovina, M. M., Silveira, R. L., Garcia-Borràs, M., Gallup, N., Johnson, C. W., Allen, M. D., Skaf, M. S., Crowley, M. F., Neidle, E. L., Houk, K. N., Beckham, G. T., DuBois, J. L., and McGechan, J. E. (2018) A promiscuous cytochrome P450 aromatic O-demethylase for lignin bioconversion. *Nature Communications* 9, 2487
33. Kontur, W. S., Bingman, C. A., Olmsted, C. N., Wassarman, D. R., Ulbrich, A., Gall, D. L., Smith, R. W., Yusko, L. M., Fox, B. G., Noguera, D. R., Coon, J. J., and Donohue, T. J. (2018) *Novosphingobium aromaticivorans* uses a Nu-class glutathione S-transferase as a glutathione lyase in breaking the beta-aryl ether bond of lignin. *J Biol Chem* 293, 4955-4968
34. Schäfer, A., Tauch, A., Jäger, W., Kalinowski, J., Thierbach, G., and Pühler, A. (1994) Small mobilizable multi-purpose cloning vectors derived from the *Escherichia coli* plasmids pK18 and pK19: selection of defined deletions in the chromosome of *Corynebacterium glutamicum. Gene* 145, 69-73
35. Deatherage, D. E., and Barrick, J. E. (2014) Identification of mutations in laboratory-evolved microbes from next-generation sequencing data using breseq. *Methods in molecular biology* (Clifton, N.J.) 1151, 165-188
36. Blommel, P. G., Martin, P. A., Seder, K. D., Wrobel, R. L., and Fox, B. G. (2009) Flexi vector cloning. *Methods in molecular biology* (Clifton, N.J.) 498, 55-73
37. Studier, F. W. (2005) Protein production by auto-induction in high-density shaking cultures. *Protein Expression and Purification* 41, 207-234
38. Sreenath, H. K., Bingman, C. A., Buchan, B. W., Seder, K. D., Burns, B. T., Geetha, H. V., Jeon, W. B., Vojtik, F. C., Aceti, D. J., Frederick, R. O., Phillips, G. N., Jr., and Fox, B. G. (2005) Protocols for production of selenomethionine-labeled proteins in 2-L polyethylene terephthalate bottles using auto-induction medium. *Protein Expr Purif* 40, 256-267
39. Camacho, C., Coulouris, G., Avagyan, V., Ma, N., Papadopoulos, J., Bealer, K., and Madden, T. L. (2009) BLAST+: architecture and applications. *BMC Bioinformatics* 10, 421
40. Shen, W., and Ren, H. (2021) TaxonKit: A practical and efficient NCBI taxonomy toolkit. *Journal of Genetics and Genomics* 48, 844-850
41. Mendler, K., Chen, H., Parks, D. H., Lobb, B., Hug, L. A., and Doxey, A. C. (2019) AnnoTree: visualization and exploration of a functionally annotated microbial tree of life. *Nucleic Acids Research* 47, 4442-4448
42. Bianchini, G., and Sánchez-Baracaldo, P. (2023) TreeViewer Version 2.1.0. v2.1.0 Ed., Zenodo
43. Simon, R., Priefer, U., and Pühler, A. (1983) A Broad Host Range Mobilization System for In Vivo Genetic Engineering: Transposon Mutagenesis in Gram Negative Bacteria. *Bio/Technology* 1, 784-791
44. Blodgett, J. A. V., Thomas, P. M., Li, G., Velasquez, J. E., van der Donk, W. A., Kelleher, N. L., and Metcalf, W. W. (2007) Unusual transformations in the biosynthesis of the antibiotic phosphinothricin tripeptide. *Nature chemical biology* 3, 480-485
45. Leahy, D. J., Hendrickson, W. A., Aukhil, I., and Erickson, H. P. (1992) Structure of a fibronectin type III domain from tenascin phased by MAD analysis of the selenomethionyl protein. *Science* 258, 987-991

| SEQUENCES |
|---|

Native Saro_1862 coding sequence (SEQ ID NO: 1)

ATGACCGACAAGCCCAGCGTCCTGTTCATCTGCACGCAGGATACC
GAGGAAGAGGAAGCCCGCTTCACCCGCGCCGCGCTCGAGGCGGCG
GGCGTCGAAGTCGTCCACCTCGATCCCAGTGTCCGCCGCTCGCTC
GGCGGGGCGGAAATCTCGCCGGAAATGGTCGCCCAGGCCGGCGGA
ATGACCATCGAGGAAGTCCGCGCCCTCGGCCACGAAGGCAAGTGC
CAGGACGCGATGATCCGTGGTGCCATCGCCGCCGCGCACGAATGG
GACGCCAGACACCCCGTCTCCGGCATTCTCGCGGTCGGCGGCTCG
ATGGGCTCGGCGCTTGCCGGTGCGCTCATGCAGAGCTTCCCCTAT
GGCCTGCCCAAGCTGATCGTCTCGACCATGGCCTCGGGCTTCACC
AAGCCCTACATGGGCGTGAAGGACATCGCGATGATGAACGCGGTG
ACCGATATCTCGGGCATCAACACGATCAGCCGCGACGTCTTCCGC
AACGCTGCCAACGCCGTTGCCGGAATGGCGAAGGGCTACGACCGC
GACAAGGGCCCCGAAAAGCCTCTCGTCCTCATCACCACGCTCGGC
ACGACGGAAACCAGCGTGAAACGCATCCGCCAGGCACTGGAAAGC
GATGGCTGCGAAGTCATGGTCTTCCATTCCTCCGGCGCGGGCGGC
CCCACGCTCGACGGGCTCGCCGCCGACAAGGACGTGGCGCTGGTC
CTGGACCTTTCCCCGACCGAGATCCTCGACCACCTCTTCGGCGGC
CTGGCTGATGCCGGTCCGGATCGCGGGCGCGCGGCCCTGCGCAAG
GGCATCCCGACGATCCTTGCCCCCGGCAATGCCGATTTCATCATC
GGCGGTCCGATCGACGCCGCGGAAGCGCAGTTTCCAGGCCGGCGC
TACCACCAGCACAACCCGCAGCTCACCGCAGTCCGCACCAACGTC
GCGGACCTTCGGAAGCTGGCCGATCACCTTGCCGCCAACGTGCGC
GAGGCCAAGGGCCCGGTCCGGGTCTTCACCCCGCTCAAGGGCTTT
TCCAGCCACGACAGCGAAACGGGCCACCTGCTCGACCTCTCGGTG
CCGGGACCCTTCGCCGAATATCTCGCCAGCGTCATGCCAGGTCAC
GTGCCGGTGACCGCCGTGGACGCCCATTTCAACGACGAAGCCTTC
TCCAGCGCGGTCATTGCCGCCGCGCGCGAGATGCTTGCCGCAAAG
AACTGA

Native Saro_1862 protein sequence (SEQ ID NO: 2)

MTDKPSVLFICTQDTEEEEARFTRAALEAAGVEVVHLDPSVRRSL
GGAEISPEMVAQAGGMTIEEVRALGHEGKCQDAMIRGAIAAAHEW
DARHPVSGILAVGGSMGSALAGALMQSFPYGLPKLIVSTMASGFT
KPYMGVKDIAMMNAVTDISGINTISRDVFRNAANAVAGMAKGYDR
DKGPEKPLVLITTLGTTETSVKRIRQALESDGCEVMVFHSSGAGG
PTLDGLAADKDVALVLDLSPTEILDHLFGGLADAGPDRGRAALRK
GIPTILAPGNADFIIGGPIDAAEAQFPGRRYHQHNPQLTAVRTNV
ADLRKLADHLAANVREAKGPVRVFTPLKGFSSHDSETGHLLDLSV
PGPFAEYLASVMPGHVPVTAVDAHENDEAFSSAVIAAAREMLAAK
N

-continued

| SEQUENCES |
|---|

Saro_1862-E16K coding sequence (SEQ ID NO: 3)

ATGACTGATAAGCCATCTGTGCTTTTTATTTGCACGCAAGATACT
AAAGAGGAGGAAGCACGTTTTACTCGCGCGGCGCTGGAAGCAGCA
GGGGTGGAGGTGGTACACCTTGATCCATCCGTCCGTCGCAGTCTG
GGGGGTGCCGAGATTTCTCCAGAGATGGTTGCCCAGGCGGGGGGT
ATGACCATTGAGGAAGTTCGCGCATTAGGACATGAAGGGAAATGC
CAAGACGCGATGATTCGTGGAGCCATTGCTGCCGCGCATGAGTGG
GACGCTCGTCATCCTGTTTCCGGAATTCTTGCCGTAGGGGGCTCG
ATGGGATCTGCCTTGGCAGGGGCGTTGATGCAGAGTTTCCCCTAC
GGCCTGCCCAAGTTGATTGTCTCTACAATGGCTTCGGGGTTTACA
AAGCCCTATATGGGTGTAAAAGATATTGCTATGATGAATGCAGTT
ACAGATATCTCAGGAATTAATACAATCTCTCGTGACGTATTCCGT
AACGCGGCGAATGCAGTGGCGGGGATGGCTAAGGGGTACGACCGT
GACAAGGGCCCAGAGAAGCCATTAGTTTTGATTACAACACTGGGA
ACCACGGAAACTTCTGTAAAGCGCATCCGCCAAGCCCTGGAGTCC
GATGGCTGTGAGGTGATGGTCTTTCACTCTTCTGGGGCAGGGGGA
CCTACGTTGGATGGGTTAGCCGCCGATAAGGATGTTGCGTTGGTG
TTGGATTTGAGTCCTACAGAGATCCTGGATCATCTGTTTGGGGGG
CTTGCTGATGCCGGACCTGACCGCGGACGTGCTGCTTTGCGCAAG
GGAATTCCAACAATTTTAGCGCCGGGAAATGCCGATTTTATCATC
GGCGGCCCTATTGACGCCGCTGAGGCTCAATTCCCTGGCCGCCGC
TATCATCAACATAATCCCCAATTAACAGCAGTCCGTACAAATGTG
GCGGATTTGCGCAAGCTTGCCGATCATTTAGCAGCAAATGTTCGC
GAAGCGAAGGGTCCAGTGCGTGTATTCACTCCATTGAAGGGGTTT
TCAAGCCATGACAGTGAAACTGGGCACTTATTGGATTTAAGCGTG
CCTGGGCCGTTCGCCGAATACTTAGCGTCGGTTATGCCCGGTCAC
GTTCCCGTTACCGCTGTCGATGCTCACTTCAACGATGAAGCGTTC
TCCTCGGCTGTCATTGCAGCCGCGCGCGAGATGTTGGCGGCAAAA
AATTAA

Saro_1862-E16K protein (SEQ ID NO: 4)

MTDKPSVLFICTQDTKEEEARFTRAALEAAGVEVVHLDPSVRRSL
GGAEISPEMVAQAGGMTIEEVRALGHEGKCQDAMIRGAIAAAHEW
DARHPVSGILAVGGSMGSALAGALMQSFPYGLPKLIVSTMASGFT
KPYMGVKDIAMMNAVTDISGINTISRDVFRNAANAVAGMAKGYDR
DKGPEKPLVLITTLGTTETSVKRIRQALESDGCEVMVFHSSGAGG
PTLDGLAADKDVALVLDLSPTEILDHLFGGLADAGPDRGRAALRK
GIPTILAPGNADFIIGGPIDAAEAQFPGRRYHQHNPQLTAVRTNV

-continued

SEQUENCES

ADLRKLADHLAANVREAKGPVRVFTPLKGFSSHDSETGHLLDLSV
PGPFAEYLASVMPGHVPVTAVDAHENDEAFSSAVIAAAREMLAAK
N

MBP-Saro_1862-E16K coding sequence
(SEQ ID NO: 5)
ATGGGACATCACCATCATCACCATCACCATGCATCCAAAATCGAA
GAAGGTAAACTGGTAATCTGGATTAACGGCGATAAAGGCTATAAC
GGTCTCGCTGAAGTCGGTAAGAAATTCGAGAAAGATACCGGAATT
AAAGTCACCGTTGAGCATCCGGATAAACTGGAAGAGAAATTCCCA
CAGGTTGCGGCAACTGGCGATGGCCCTGACATTATCTTCTGGGCA
CACGACCGCTTTGGTGGCTACGCTCAATCTGGCCTGTTGGCTGAA
ATCACCCCGGACAAAGCGTTCCAGGACAAGCTGTATCCGTTTACC
TGGGATGCCGTACGTTACAACGGCAAGCTGATTGCTTACCCGATC
GCTGTTGAAGCGTTATCGCTGATTTATAACAAAGATCTGCTGCCG
AACCCGCCAAAAACCTGGGAAGAGATCCCGGCGCTGGATAAAGAA
CTGAAAGCGAAAGGTAAGAGCGCGCTGATGTTCAACCTGCAAGAA
CCGTACTTCACCTGGCCGCTGATTGCTGCTGACGGGGGTTATGCG
TTCAAGTATGAAAACGGCAAGTACGACATTAAAGACGTGGGCGTG
GATAACGCTGGCGCGAAAGCGGGTCTGACCTTCCTGGTTGACCTG
ATTAAAAACAAACACATGAATGCAGACACCGATTACTCCATCGCA
GAAGCTGCCTTTAATAAAGGCGAAACAGCGATGACCATCAACGGC
CCGTGGGCATGGTCCAACATCGACACCAGCAAAGTGAATTATGGT
GTAACGGTACTGCCGACCTTCAAGGGTCAACCATCCAAACCGTTC
GTTGGCGTGCTGAGCGCAGGTATTAACGCCGCCAGTCCGAACAAA
GAGCTGGCAAAAGAGTTCCTCGAAAACTATCTGCTGACTGATGAA
GGTCTGGAAGCGGTTAATAAAGACAAACCGCTGGGTGCCGTAGCG
CTGAAGTCTTACGAGGAAGAGTTGGCGAAAGATCCACGTATTGCC
GCCACTATGGAAAACGCCCAGAAAGGTGAAATCATGCCGAACATC
CCGCAGATGTCCGCTTTCTGGTATGCCGTGCGTACTGCGGTGATC
AACGCCGCCAGCGGTCGTCAGACTGTCGATGAAGCCCTGAAAGAC
GCGCAGACTTTAATTAACGGCGACGGTGCCGGGCTGGAAGTTCTG
TTCCAGGGGCCCGCGATCGCGGAAAACCTGTACTTCCAGTCCACT
GATAAGCCATCTGTGCTTTTTATTTGCACGCAAGATACTAAAGAG
GAGGAAGCACGTTTTACTCGCGCGGCGCTGGAAGCAGCAGGGGTG
GAGGTGGTACACCTTGATCCATCCGTCCGTCGCAGTCTGGGGGGT
GCCGAGATTTCTCCAGAGATGGTTGCCCAGGCGGGGGGTATGACC
ATTGAGGAAGTTCGCGCATTAGGACATGAAGGGAAATGCCAAGAC
GCGATGATTCGTGGAGCCATTGCTGCCGCGCATGAGTGGGACGCT
CGTCATCCTGTTTCCGGAATTCTTGCCGTAGGGGGCTCGATGGGA
TCTGCCTTGGCAGGGGCGTTGATGCAGAGTTTCCCCTACGGCCTG
CCCAAGTTGATTGTCTCTACAATGGCTTCGGGGTTTACAAAGCCC
TATATGGGTGTAAAAGATATTGCTATGATGAATGCAGTTACAGAT
ATCTCAGGAATTAATACAATCTCTCGTGACGTATTCCGTAACGCG
GCGAATGCAGTGGCGGGGATGGCTAAGGGGTACGACCGTGACAAG
GGCCCAGAGAAGCCATTAGTTTTGATTACAACACTGGGAACCACG
GAAACTTCTGTAAAGCGCATCCGCCAAGCCCTGGAGTCCGATGGC
TGTGAGGTGATGGTCTTTCACTCTTCTGGGGCAGGGGGACCTACG
TTGGATGGGTTAGCCGCCGATAAGGATGTTGCGTTGGTGTTGGAT
TTGAGTCCTACAGAGATCCTGGATCATCTGTTTGGGGGGCTTGCT
GATGCCGGACCTGACCGCGGACGTGCTGCTTTGCGCAAGGGAATT
CCAACAATTTTAGCGCCGGGAAATGCCGATTTTATCATCGGCGGC
CCTATTGACGCCGCTGAGGCTCAATTCCCTGGCCGCCGCTATCAT
CAACATAATCCCCAATTAACAGCAGTCCGTACAAATGTGGCGGAT
TTGCGCAAGCTTGCCGATCATTTAGCAGCAAATGTTCGCGAAGCG
AAGGGTCCAGTGCGTGTATTCACTCCATTGAAGGGGTTTTCAAGC
CATGACAGTGAAACTGGGCACTTATTGGATTTAAGCGTGCCTGGG
CCGTTCGCCGAATACTTAGCGTCGGTTATGCCCGGTCACGTTCCC
GTTACCGCTGTCGATGCTCACTTCAACGATGAAGCGTTCTCCTCG
GCTGTCATTGCAGCCGCGCGCGAGATGTTGGCGGCAAAAAATTAA MBP-Saro_1862-E16K protein
(SEQ ID NO: 6)
MGHHHHHHHHASKIEEGKLVIWINGDKGYNGLAEVGKKFEKDTGI
KVTVEHPDKLEEKFPQVAATGDGPDIIFWAHDRFGGYAQSGLLAE
ITPDKAFQDKLYPFTWDAVRYNGKLIAYPIAVEALSLIYNKDLLP
NPPKTWEEIPALDKELKAKGKSALMFNLQEPYFTWPLIAADGGYA
FKYENGKYDIKDVGVDNAGAKAGLTFLVDLIKNKHMNADTDYSIA
EAAFNKGETAMTINGPWAWSNIDTSKVNYGVTVLPTFKGQPSKPF
VGVLSAGINAASPNKELAKEFLENYLLTDEGLEAVNKDKPLGAVA
LKSYEEELAKDPRIAATMENAQKGEIMPNIPQMSAFWYAVRTAVI
NAASGRQTVDEALKDAQTLINGDGAGLEVLFQGPAIAENLYFQST
DKPSVLFICTQDTKEEEARFTRAALEAAGVEVVHLDPSVRRSLGG
AEISPEMVAQAGGMTIEEVRALGHEGKCQDAMIRGAIAAAHEWDA
RHPVSGILAVGGSMGSALAGALMQSFPYGLPKLIVSTMASGFTKP
YMGVKDIAMMNAVTDISGINTISRDVFRNAANAVAGMAKGYDRDK
GPEKPLVLITTLGTTETSVKRIRQALESDGCEVMVFHSSGAGGPT
LDGLAADKDVALVLDLSPTEILDHLFGGLADAGPDRGRAALRKGI
PTILAPGNADFIIGGPIDAAEAQFPGRRYHQHNPQLTAVRTNVAD
LRKLADHLAANVREAKGPVRVFTPLKGFSSHDSETGHLLDLSVPG
PFAEYLASVMPGHVPVTAVDAHENDEAFSSAVIAAAREMLAAKN

What is claimed is:

1. A recombinant microorganism comprising a recombinant aromatic kinase gene, wherein the recombinant aromatic kinase gene encodes an aromatic kinase protein, wherein the aromatic kinase protein is a homolog of Saro_1862 of *Novosphingobium aromaticivorans* DSM12444 comprising amino acid sequence comprising a lysine at a position corresponding to position 16 of SEQ ID NO:4.

2. The recombinant microorganism of claim 1, wherein the amino acid sequence is at least 95% or at least 99% identical to SEQ ID NO:4 or any sequence identified in Table 7.

3. The recombinant microorganism of claim 1, wherein the amino acid sequence is at least 80% identical to SEQ ID NO:4.

4. The recombinant microorganism of claim 1, wherein the amino acid sequence is at least 95% identical to SEQ ID NO:4.

5. The recombinant microorganism of claim 1, wherein the recombinant microorganism is a bacterium.

6. The recombinant microorganism of claim 1, wherein the recombinant microorganism is a member of Actinomycetota, Alphaproteobacteria, Aquificae, Bacillota, Bacteroidota, Betaproteobacteria, Chlorobiota, Chloroflexota, Desulfuromonadia, Epsilonproteobacteria, Gammaproteobacteria, Nitrospiria, Planctomycetota, Thermomicrobiota, or Verrucomicrobiota.

7. The recombinant microorganism of claim 1, wherein the recombinant microorganism is an Alphaproteobacterium.

8. The recombinant microorganism of claim 1, wherein the recombinant microorganism is from an order selected from the group consisting of Sphingomonadales, *Actinomyces*, Gammaproteobacteria, Betaproteobacteria, and Bacilli.

9. The recombinant microorganism of claim 1, wherein the recombinant microorganism is from family Erythrobacteraceae.

10. The recombinant microorganism of claim 1, wherein the recombinant microorganism is from genus *Novosphingobium.*

11. The recombinant microorganism of claim 1, wherein the recombinant microorganism is capable of growing on acetovanillone, guaiacylpropanone, or p-OH acetophenone as a sole carbon source.

12. The recombinant microorganism of claim 1, wherein:
the amino acid sequence is at least 95% identical to SEQ ID NO:4; and
the recombinant microorganism is from genus *Novosphingobium.*

13. The recombinant microorganism of claim 12, wherein the recombinant microorganism is capable of growing on acetovanillone, guaiacylpropanone, or p-OH acetophenone as a sole carbon source.

14. The recombinant microorganism of claim 12, wherein the recombinant microorganism is capable of growing on acetovanillone as a sole carbon source.

15. A method of catabolizing a lignin aromatic, the method comprising culturing the recombinant microorganism of claim 1 in a medium comprising the lignin aromatic to thereby catabolize the lignin aromatic.

16. The method of claim 15, wherein the lignin aromatic comprises one or more of acetovanillone, guaiacylpropanone, and p-OH acetophenone.

17. The method of claim 15, wherein the lignin aromatic comprises acetovanillone.

18. A recombinant aromatic kinase protein comprising an amino acid sequence at least 95% identical to SEQ ID NO:4, wherein the amino acid sequence comprises a lysine at a position corresponding to position 16 of SEQ ID NO:4.

19. The recombinant aromatic kinase protein of claim 18, wherein the amino acid sequence is at least 99% identical to SEQ ID NO:4.

* * * * *

SEQUENCE LISTING

```
Sequence total quantity: 6
SEQ ID NO: 1            moltype = DNA  length = 1221
FEATURE                 Location/Qualifiers
source                  1..1221
                        mol_type = genomic DNA
                        organism = Novosphingobium aromaticivorans
SEQUENCE: 1
atgaccgaca agcccagcgt cctgttcatc tgcacgcagg ataccgagga agaggaagcc  60
cgcttcaccc gcgccgcgct cgaggcggcg ggcgtcgaag tcgtccacct cgatcccagt  120
gtccgccgct cgctcggcgg ggcggaaatc tcgccggaaa tggtcgccca ggccggcgga  180
atgaccatcg aggaagtccg cgccctcggc cacgaaggca agtgccagga cgcgatgatc  240
cgtggtgcca tcgccgccgc gcacgaatgg gacgccagac accccgtctc cggcattctc  300
gcggtcggcg gctcgatggg ctcggcgctt gccggtgcgc tcatgcagag cttcccctat  360
ggcctgccca agctgatcgt ctcgaccatg gcctcgggct tcaccaagcc ctacatgggc  420
gtgaaggaca tcgcgatgat gaacgcggtg accgatatct cgggcatcaa cacgatcagc  480
cgcgacgtct tccgcaacgc tgccaacgcc gttgccggaa tggcgaaggg ctacgaccgc  540
gacaagggcc ccgaaaagcc tctcgtcctc atcaccacgc tcggcacgac ggaaaccagc  600
gtgaaacgca tccgccaggc actggaaagc gatggctgcg aagtcatggt cttccattcc  660
tccggcgcgg gcggccccac gctcgacggg ctcgccgccg acaaggacgt ggcgctggtc  720
ctggaccttt ccccgaccga gatcctcgac cacctcttcg gcggcctggc tgatgccggt  780
ccggatcgcg ggcgcgcggc cctgcgcaag ggcatcccga cgatccttgc cccggcaat   840
gccgatttca tcatcggcgg tccgatcgac gccgcggaag cgcagtttcc aggccggcgc  900
taccaccagc acaacccgca gctcaccgca gtccgcacca acgtcgcgga ccttcggaag  960
ctggccgatc accttgccgc caacgtgcgc gaggccaagg gcccggtccg ggtcttcacc  1020
ccgctcaagg gcttttccag ccacgacagc gaaacgggcc acctgctcga cctctcggtg  1080
ccgggaccct tcgccgaata tctcgccagc gtcatgccag gtcacgtgcc ggtgaccgcc  1140
gtggacgccc atttcaacga cgaagccttc tccagcgcgg tcattgccgc cgcgcgcgag  1200
atgcttgccg caaagaactg a                                            1221

SEQ ID NO: 2            moltype = AA  length = 406
FEATURE                 Location/Qualifiers
source                  1..406
                        mol_type = protein
                        organism = Novosphingobium aromaticivorans
SEQUENCE: 2
MTDKPSVLFI CTQDTEEEEA RFTRAALEAA GVEVVHLDPS VRRSLGGAEI SPEMVAQAGG  60
MTIEEVRALG HEGKCQDAMI RGAIAAAHEW DARHPVSGIL AVGGSMGSAL AGALMQSFPY  120
GLPKLIVSTM ASGFTKPYMG VKDIAMMNAV TDISGINTIS RDVFRNAANA VAGMAKGYDR  180
DKGPEKPLVL ITTLGTTETS VKRIRQALES DGCEVMVFHS SGAGGPTLDG LAADKDVALV  240
LDLSPTEILD HLFGGLADAG PDRGRAALRK GIPTILAPGN ADFIIGGPID AAEAQFPGRR  300
YHQHNPQLTA VRTNVADLRK LADHLAANVR EAKGPVRVFT PLKGFSSHDS ETGHLLDLSV  360
PGPFAEYLAS VMPGHVPVTA VDAHFNDEAF SSAVIAAARE MLAAKN                  406

SEQ ID NO: 3            moltype = DNA  length = 1221
FEATURE                 Location/Qualifiers
source                  1..1221
                        mol_type = other DNA
                        organism = synthetic construct
SEQUENCE: 3
atgactgata agccatctgt gctttttatt tgcacgcaag atactaaaga ggaggaagca  60
cgttttactc gcgcggcgct ggaagcagca ggggtggagg tggtacacct tgatccatcc  120
gtccgtcgca gtctgggggg tgccgagatt tctccagaga tggttgccca ggcggggggt  180
atgaccattg aggaagttcg cgcattagga catgaaggga aatgccaaga cgcgatgatt  240
cgtggagcca ttgctgccgc gcatgagtgg gacgctcgtc atcctgtttc cggaattctt  300
gccgtagggg gctcgatggg atctgccttg gcaggggcgt tgatgcagag tttcccctac  360
ggcctgccca agttgattgt ctctacaatg gcttcggggt ttacaaagcc ctatatgggt  420
gtaaaagata ttgctatgat gaatgcagtt acagatatct caggaattaa tacaatctct  480
cgtgacgtat tccgtaacgc ggcgaatgca gtggcgggga tggctaaggg gtacgaccgt  540
gacaagggcc cagagaagcc attagttttg attacaacac tgggaaccac ggaaacttct  600
gtaaagcgca tccgccaagc cctggagtcc gatggctgtg aggtgatggt ctttcactct  660
tctggggcag ggggacctac gttggatggg ttagccgccg ataaggatgt tgcgttggtg  720
ttggatttga gtcctacaga gatcctggat catctgtttg gggggcttgc tgatgccgga  780
cctgaccgcg gacgtgctgc tttgcgcaag ggaattccaa caattttagc gccgggaaat  840
gccgatttta tcatcggcgg ccctattgac gccgctgagg ctcaattccc tggccgccgc  900
tatcatcaac ataatcccca attaacagca gtccgtacaa atgtggcgga tttgcgcaag  960
cttgccgatc atttagcagc aaatgttcgc gaagcgaagg gtccagtgcg tgtattcact  1020
ccattgaagg ggttttcaag ccatgacagt gaaactgggc acttattgga tttaagcgtg  1080
cctgggccgt tcgccgaata cttagcgtcg gttatgcccg gtcacgttcc cgttaccgct  1140
gtcgatgctc acttcaacga tgaagcgttc tcctcggctg tcattgcagc cgcgcgcgag  1200
atgttggcgg caaaaaatta a                                            1221

SEQ ID NO: 4            moltype = AA  length = 406
FEATURE                 Location/Qualifiers
source                  1..406
                        mol_type = protein
                        organism = synthetic construct
SEQUENCE: 4
MTDKPSVLFI CTQDTKEEEA RFTRAALEAA GVEVVHLDPS VRRSLGGAEI SPEMVAQAGG  60
```

-continued

```
MTIEEVRALG HEGKCQDAMI RGAIAAAHEW DARHPVSGIL AVGGSMGSAL AGALMQSFPY  120
GLPKLIVSTM ASGFTKPYMG VKDIAMMNAV TDISGINTIS RDVFRNAANA VAGMAKGYDR  180
DKGPEKPLVL ITTLGTTETS VKRIRQALES DGCEVMVFHS SGAGGPTLDG LAADKDVALV  240
LDLSPTEILD HLFGGLADAG PDRGRAALRK GIPTILAPGN ADFIIGGPID AAEAQFPGRR  300
YHQHNPQLTA VRTNVADLRK LADHLAANVR EAKGPVRVFT PLKGFSSHDS ETGHLLDLSV  360
PGPFAEYLAS VMPGHVPVTA VDAHFNDEAF SSAVIAAARE MLAAKN                 406

SEQ ID NO: 5           moltype = DNA  length = 2430
FEATURE                Location/Qualifiers
source                 1..2430
                       mol_type = other DNA
                       organism = synthetic construct
SEQUENCE: 5
atgggacatc accatcatca ccatcaccat gcatccaaaa tcgaagaagg taaactggta  60
atctggatta acggcgataa aggctataac ggtctcgctg aagtcggtaa gaaattcgag  120
aaagataccg gaattaaagt caccgttgag catccggata aactggaaga gaaattccca  180
caggttgcgg caactggcga tggccctgac attatcttct gggcacacga ccgctttggt  240
ggctacgctc aatctggcct gttggctgaa atcaccccgg acaaagcgtt ccaggacaag  300
ctgtatccgt ttacctggga tgccgtacgt tacaacggca agctgattgc ttacccgatc  360
gctgttgaag cgttatcgct gatttataac aaagatctgc tgccgaaccc gccaaaaacc  420
tgggaagaga tcccggcgct ggataaagaa ctgaaagcga aaggtaagag cgcgctgatg  480
ttcaacctgc aagaaccgta cttcacctgg ccgctgattg ctgctgacgg gggttatgcg  540
ttcaagtatg aaaacggcaa gtacgacatt aaagacgtgg gcgtggataa cgctggcgcg  600
aaagcgggtc tgaccttcct ggttgacctg attaaaaaca aacacatgaa tgcagacacc  660
gattactcca tcgcagaagc tgcctttaat aaaggcgaaa cagcgatgac catcaacggc  720
ccgtgggcat ggtccaacat cgacaccagc aaagtgaatt atggtgtaac ggtactgccg  780
accttcaagg gtcaaccatc caaaccgttc gttggcgtgc tgagcgcagg tattaacgcc  840
gccagtccga acaaagagct ggcaaaagag ttcctcgaaa actatctgct gactgatgaa  900
ggtctggaag cggttaataa agacaaaccg ctgggtgccg tagcgctgaa gtcttacgag  960
gaagagttgg cgaaagatcc acgtattgcc gccactatgg aaaacgccca gaaaggtgaa  1020
atcatgccga acatcccgca gatgtccgct ttctggtatg ccgtgcgtac tgcggtgatc  1080
aacgccgcca gcggtcgtca gactgtcgat gaagccctga aagacgcgca gactttaatt  1140
aacggcgacg gtgccgggct ggaagttctg ttccaggggc ccgcgatcgc ggaaaacctg  1200
tacttccagt ccactgataa gccatctgtg ctttttattt gcacgcaaga tactaaagag  1260
gaggaagcac gttttactcg cgcggcgctg gaagcagcag gggtggaggt ggtacacctt  1320
gatccatccg tccgtcgcag tctgggggt gccgagattt ctccagagat ggttgcccag  1380
gcgggggggta tgaccattga ggaagttcgc gcattaggac atgaagggaa atgccaagac  1440
gcgatgattc gtggagccat tgctgccgcg catgagtggg acgctcgtca tcctgtttcc  1500
ggaattcttg ccgtaggggg ctcgatggga tctgccttgg caggggcgtt gatgcagagt  1560
ttcccctacg gcctgcccaa gttgattgtc tctacaatgg cttcggggtt tacaaagccc  1620
tatatgggtg taaaagatat tgctatgatg aatgcagtta cagatatctc aggaattaat  1680
acaatctctc gtgacgtatt ccgtaacgcg gcgaatgcag tggcggggat ggctaagggg  1740
tacgaccgtg acaagggccc agagaagcca ttagttttga ttacaacact gggaaccacg  1800
gaaacttctg taaagcgcat ccgccaagcc ctggagtccg atggctgtga ggtgatggtc  1860
tttcactctt ctggggcagg gggacctacg ttggatgggt tagccgccga taaggatgtt  1920
gcgttggtgt tggatttgag tcctacagag atcctggatc atctgtttgg ggggcttgct  1980
gatgccggac ctgaccgcgg acgtgctgct ttgcgcaagg gaattccaac aattttagcg  2040
ccgggaaatg ccgattttat catcggcggc cctattgacg ccgctgaggc tcaattccct  2100
ggccgccgct atcatcaaca taatccccaa ttaacagcag tccgtacaaa tgtggcggat  2160
ttgcgcaagc ttgccgatca tttagcagca aatgttcgcg aagcgaaggg tccagtgcgt  2220
gtattcactc cattgaaggg gttttcaagc catgacagtg aaactgggca cttattggat  2280
ttaagcgtgc ctgggccgtt cgccgaatac ttagcgtcgg ttatgcccgg tcacgttccc  2340
gttaccgctg tcgatgctca cttcaacgat gaagcgttct cctcggctgt cattgcagcc  2400
gcgcgcgaga tgttggcggc aaaaaattaa                                   2430

SEQ ID NO: 6           moltype = AA  length = 809
FEATURE                Location/Qualifiers
source                 1..809
                       mol_type = protein
                       organism = synthetic construct
SEQUENCE: 6
MGHHHHHHHH ASKIEEGKLV IWINGDKGYN GLAEVGKKFE KDTGIKVTVE HPDKLEEKFP  60
QVAATGDGPD IIFWAHDRFG GYAQSGLLAE ITPDKAFQDK LYPFTWDAVR YNGKLIAYPI  120
AVEALSLIYN KDLLPNPPKT WEEIPALDKE LKAKGKSALM FNLQEPYFTW PLIAADGGYA  180
FKYENGKYDI KDVGVDNAGA KAGLTFLVDL IKNKHMNADT DYSIAEAAFN KGETAMTING  240
PWAWSNIDTS KVNYGVTVLP TFKGQPSKPF VGVLSAGINA ASPNKELAKE FLENYLLTDE  300
GLEAVNKDKP LGAVALKSYE EELAKDPRIA ATMENAQKGE IMPNIPQMSA FWYAVRTAVI  360
NAASGRQTVD EALKDAQTLI NGDGAGLEVL FQGPAIAENL YFQSTDKPSV LFICTQDTKE  420
EEARFTRAAL EAAGVEVVHL DPSVRRSLGG AEISPEMVAQ AGGMTIEEVR ALGHEGKCQD  480
AMIRGAIAAA HEWDARHPVS GILAVGGSMG SALAGALMQS FPYGLPKLIV STMASGFTKP  540
YMGVKDIAMM NAVTDISGIN TISRDVFRNA ANAVAGMAKG YDRDKGPEKP LVLITTLGTT  600
ETSVKRIRQA LESDGCEVMV FHSSGAGGPT LDGLAADKDV ALVLDLSPTE ILDHLFGGLA  660
DAGPDRGRAA LRKGIPTILA PGNADFIIGG PIDAAEAQFP GRRYHQHNPQ LTAVRTNVAD  720
LRKLADHLAA NVREAKGPVR VFTPLKGFSS HDSETGHLLD LSVPGPFAEY LASVMPGHVP  780
VTAVDAHFND EAFSSAVIAA AREMLAAKN                                    809
```